United States Patent
Charles et al.

(12) 
(10) Patent No.: US 6,893,650 B1
(45) Date of Patent: May 17, 2005

(54) N²-PHENYLAMIDINE DERIVATIVES

(75) Inventors: Mark David Charles, Brighton (GB);
Wilfried Franke, Somerset West (ZA);
David Eric Green, Essex (GB);
Thomas Lawley Hough, Essex (GB);
Dale Robert Mitchell, Essex (GB);
Donald James Simpson, Essex (GB);
John Frederick Atherall, Essex (GB)

(73) Assignee: Bayer Cropscience GmbH (DE)

( * ) Notice: Subject to any disclaimer, the term of this patent is extended or adjusted under 35 U.S.C. 154(b) by 0 days.

(21) Appl. No.: 09/890,775

(22) PCT Filed: Feb. 4, 2000

(86) PCT No.: PCT/GB00/00345
§ 371 (c)(1),
(2), (4) Date: Sep. 26, 2002

(87) PCT Pub. No.: WO00/46184
PCT Pub. Date: Aug. 10, 2000

(30) Foreign Application Priority Data

Feb. 6, 1999 (GB) .............................. 9902592

(51) Int. Cl.⁷ .................... A61K 31/155; C07D 233/37; C07D 261/20; C07D 237/00; A01N 43/82
(52) U.S. Cl. ...................... 424/405; 546/184; 546/329; 546/187; 546/261; 546/271.4; 546/273.7; 546/272.7; 548/146; 548/151; 548/152; 548/153; 544/242; 544/252; 544/238; 544/224; 564/116; 564/243
(58) Field of Search .......................... 424/405; 546/184, 546/329, 187, 261, 268.1, 268.4, 271.4, 272.7, 273.7; 548/146, 151, 152, 153; 544/242, 252, 238, 224; 564/116, 243

(56) References Cited

U.S. PATENT DOCUMENTS 3,284,289 A 11/1966 Dieter
4,209,319 A 6/1980 Dieter et al.
5,739,153 A 4/1998 Peignier et al. .............. 514/406

FOREIGN PATENT DOCUMENTS

EP 0375414 6/1990
EP 0429281 5/1991
WO 9522532 8/1995

OTHER PUBLICATIONS

Vors et al., AN 2004:347984 HCAPLUS< ABstract of EP 1413301.*

Labourdette et al., AN 2003:204157, HCAPLUS, abstract of FR 2829362.*

* cited by examiner

Primary Examiner—Sabiha Qazi
(74) Attorney, Agent, or Firm—Ostrolenk, Faber, Gerb & Soffen, LLP

(57) ABSTRACT

The invention provides fungicidal compounds of formula (I) and salts thereof wherein: $R^1$ is alkyl, alkenyl, alkynyl, carbocyclyl or heterocyclyl, each of which may be substituted, or hydrogen; $R^2$ and $R^3$, which may be the same or different, are any group defined for $R^1$; cyano; acyl; —$OR^a$ or —$SR^a$, where $R^a$ is alkyl, alkenyl, alkynyl, carbocyclyl or heterocyclyl, each of which may be substituted; or $R^2$ and $R^3$, or $R^2$ and $R^1$, together with their interconnecting atoms may form a ring, which may be substituted; $R^4$ is alkyl, alkenyl, alkynyl, carbocyclyl or heterocyclyl, each of which may be substituted; hydroxy; mercapto; azido; nitro; halogen; cyano; acyl; optionally substituted amino; cyanato; thiocyanato; —$SF_5$; —$OR^a$; —$SR^a$ or —$Si(R^a)_3$; m is 0 to 3; when present $R^5$, which may be the same or different to any other $R^5$, is any group defined for $R^4$; $R^6$ is optionally substituted carbo- or heterocylclyl; and A is a defined linking group, or —A—$R^6$ and $R^5$ together with benzene ring M form an optionally substituted fused ring system.

22 Claims, No Drawings

N²-PHENYLAMIDINE DERIVATIVES

This invention relates to the use of compounds as fungicides.

WO 95/22532 relates to substituted phenyltriazolinones claimed as herbicides and discloses inter alia a compound of formula A for which there is no characterising data therein.

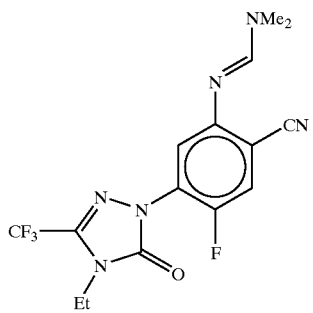

(A)

The abstract, composition claim and use claim refer only to the use of such compounds as herbicides and indeed the description supports the invention only with herbicidal activity data. There is a sentence in the specification that states that certain compounds show fungicidal activity, although no fungicidal activity data are provided. No indication is given as to which compounds are fungicidal and there is no suggestion that compound A could be fungicidal.

We have now found that certain amidines have fungicidal activity. Therefore, the invention provides the use of a compound of general formula I and salts thereof as fungicides

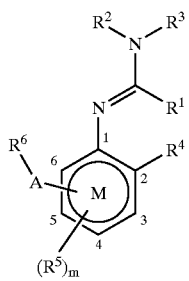

(I)

wherein $R^1$ is alkyl, alkenyl, alkynyl, carbocyclyl or heterocyclyl, each of which may be substituted, or hydrogen;

$R^2$ and $R^3$, which may be the same or different, are any group defined for $R^1$; cyano; acyl; —$OR^a$ or —$SR^a$, where $R^a$ is alkyl, alkenyl, alkynyl, carbocyclyl or heterocyclyl, each of which may be substituted; or $R^2$ and $R^3$, or $R^2$ and $R^1$, together with their interconnecting atoms may form a ring, which may be substituted;

$R^4$ is alkyl, alkenyl, alkynyl, carbocyclyl or heterocyclyl, each of which may be substituted; hydroxy; mercapto; azido; nitro; halogen; cyano; acyl; optionally substituted amino; cyanato; thiocyanato; —$SF_5$; —$OR^a$; —$SR^a$ or —$Si(R^a)_3$;

m is 0 to 3;

when present $R^5$, which may be the same or different to any other $R^5$, is any group defined for $R^4$;

$R^6$ is optionally substituted carbo- or heterocyclyl; and A is a direct bond, —O—, —$S(O)_n$—, —$NR^9$—, —$CR^7$=$CR^7$—, —C≡C—, —$A^1$—, —$A^1$—$A^1$—, —O—$(A^1)_k$—O—, —O—$(A^1)_k$—, —$A^3$—, —$A^4$—, —$A^1$O—, —$A^1S(O)_n$—, —$A^2$—, $OA^2$—, —$NR^9A^2$—, —$OA^2$—, —$OA^2$—$C(R^7)$=C($R^8$)—, —$S(O)_n$ $A^1$—, —$A^1$—$A^4$—, —$A^1$—$A^4$—C($R^8$)=N—N=$CR^8$—, —$A^1$—$A^4$—C($R^8$)=N—$X^2$—$X^3$—, —$A^1$—$A^4$—$A^3$—, —$A^1$—$A^4$—N($R^9$)—, —$A^1$—$A^4$—X—$CH_2$—, —$A^1$—$A^4$—$A^1$—, —$A^1$—$A^4$—$CH_2X$—, —$A^1$—$A^4$—C($R^8$)=N—$X^2$—$X^3$—$X^1$—, —$A^1$—X—C($R^8$)=N—, —$A^1$—X—C($R^8$)=N—N=$CR^8$—, —$A^1$—X—C($R^8$)=N—N($R^9$)—, —$A^1$—X—$A^2$—$X^1$—, —$A^1$—O—$A^3$—, —$A^1$—O—C($R^7$)=C($R^8$)—, —$A^1$—O—N($R^9$)—$A^2$—N($R^9$)—, —$A^1$—O—N($R^9$)—$A^2$—, —$A^1$—N$R^9$)—$A^2$—N ($R^9$)—, —$A^1$—N($R^9$)—$A^2$—, —$A^1$—N($R^9$)—N=C($R^8$)—, —$A^3$—$A^1$—, —$A^4$—$A^3$—, —$A^2$—$NR^9$—, —$A^1$—$A^2$—$X^1$—, —$A^1$—$A^1$—$A^2$—$X^1$—, —O—$A^2$—N($R^9$)—$A^2$—, —$CR^7$=$CR^7$—$A^2$—$X^1$—, —C=C—$A^2$—X —, —N=C($R^8$)—$A^2$—$X^1$—, —C($R^8$)=N—N C($R^8$)—, —C($R^8$)=N—N($R^9$)—, —$(CH_2)_2$—O—N=$CR^8$— or —X—$A^2$—N($R^9$)— where n is 0, 1 or 2, k is 1 to 9, $A^1$ is —$CHR^7$—, $A^2$ is —C(=X)—, $A^3$ is —C($R^8$)=N—O—, $A^4$ is —O—N=C($R^8$)—, X is O or S, $X^1$ is O, S, $NR^9$ or a direct bond, $X^2$ is O, $NR^9$ or a direct bond, $X^3$ is hydrogen, —C(=O)—, —$SO_2$— or a direct bond, $R^7$, which may be the same or different to any other $R^7$, is alkyl, cycloalkyl or phenyl, each of which may be substituted; or is hydrogen, halogen, cyano or acyl;

$R^8$, which may be the same or different to any other $R^8$, is alkyl, alkenyl, alkynyl, alkoxy, alkylthio, carbo- or heterocyclyl, each of which may be substituted; or is hydrogen:

$R^9$, which may be the same or different to any other $R^9$, is optionally substituted alkyl, optionally substituted carbo- or heterocyclyl, hydrogen or acyl; or two $R^9$ groups on A, together with the connecting atoms, form a 5 to 7 membered ring;

where the moiety depicted on the right side of linkage A is attached to $R^6$;

or —A—$R^6$ and $R^5$ together with benzene ring M form an optionally substituted fused ring system.

Preferably $R^1$ is alkyl, alkenyl or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen), or is hydrogen. $R^1$ is especially $C_1$–$C_{10}$ alkyl (e.g. methyl) or hydrogen.

Preferably $R^2$ and $R^3$, which may be the same or different, are alkyl, alkenyl or alkynyl, each of which may be substituted by alkoxy, haloalkoxy, alkylthio, halogen or optionally substituted phenyl (preferably phenyl, optionally substituted by alkyl, haloalkyl, alkoxy, haloalkoxy or alkylthio, each containing 1 to 5 carbon atoms, or by halogen), or is hydrogen, alkoxy, alkoxyalkoxy, benzyloxy, cyano or alkylcarbonyl. $R^2$ and $R^3$, which may be the same or different, are especially $C_1$–$C_{10}$alkyl (e.g. methyl or ethyl) or hydrogen.

Preferably $R^4$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen); or is hydroxy; halogen; cyano; acyl (preferably —C(=O)$R^c$, —C(=S)$R^c$ or —S(O)$_p R^c$, where $R^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio); alkoxy; haloalkoxy; or alkylthio. $R^4$ is especially $C_1$–$C_{10}$ alkyl (e.g. methyl or ethyl) or halogen.

Preferably m is 0 or 1, especially 1.

When present, $R^5$ is preferably a group defined for preferred $R^4$ above. $R^5$ is especially $C_1$–$C_{10}$ alkyl or halogen.

When present, the group $R^5$ is preferably attached at the 5 position of ring M.

Preferably A is a direct bond, —O—, —S(O)$_n A^1$—, —O($A^1$)$_k$, —S(O)$_n$—, —NR$^9 A^2$—, —$A^2$—, —O$A^2$—, —O$A^2$—$A^1$—, —NR$^9$—or —O($A^1$)$_k$O—Particularly A is a direct bond, —O—, —S—, —NR$^9$—, —CHR$^7$—or —O—CHR$^7$—. Especially A is a direct bond or —O—. When present, $R^9$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen); or is hydrogen ($R^9$ is especially $C_1$–$C_{10}$ alkyl or hydrogen). When present, $R^7$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or by halogen); or is hydroxy; halogen; cyano: acyl; alkoxy; haloalkoxy; alkylthio; or hydrogen ($R^7$ is especially $C_1$–$C_{10}$ alkyl or hydrogen).

Preferably A is attached to the 4 position of benzene ring M.

Preferably $R^6$ is optionally substituted phenyl or optionally substituted aromatic heterocyclyl [preferably thiazolyl, isothiazolyl, thiadiazolyl [particularly 1,2,4-thiadiazolyl], pyridyl or pyrimidinyl].

When substituted, $R^6$ may be substituted by one or more substituents, which may be the same or different, and may be selected from the preferred list: alkyl, alkenyl, alkynyl, carbo- or heterocycyl, each of which may be substituted;

hydroxy; mercapto; azido; nitro; halogen; cyano: acyl; optionally substituted amino; cyanato; thiocyanato; —SF$_5$; —OR$^a$; —SR$^a$ and —Si(R$^a$)$_3$, where $R^a$ is alkyl, alkenyl, alkynyl, carbocyclyl or heterocyclyl, each of which may be substituted.

A preferred list of substituents on $R^6$ is: hydroxy; halogen; cyano; acyl (preferably —C(=O)$R^c$, —C(=S)$R^c$ or —S(O)$_p$ $R^c$, where $R^c$ is alkyl, haloalkyl, alkoxy, haloalkoxy, alkylthio, amino, monalkylamino, dialkylamino or phenyl optionally substituted by alkyl, haloalkyl, alkoxy, haloalkoxy or alkylthio); amino: alkylamino; dialkylamino; alkyl; haloalkyl; R$^a$O-alkyl; acyloxyalkyl; cyano-oxyalkyl; alkoxy; haloalkoxy; alkylthio; carbocyclyl (preferably cyclohexyl or cyclopentyl) optionally substituted by alkyl, haloalkyl, alkoxy, haloalkoxy or alkylthio; and benzyl optionally substituted by alkyl, haloalkyl, alkoxy, haloalkoxy or alkylthio.

A particularly preferred list of substituents on $R^6$ is: cyclopentyl, cyclohexyl or benzyl, optionally substituted by alkyl, haloalkyl, alkoxy, haloalkoxy, or alkylthio; or is halogen; alkyl; haloalkyl; alkoxyalkyl; hydroxyalkyl; alkoxy; or alkylthio.

In a preferred embodiment, the invention provides the use of a compound of general formula I and salts thereof as fungicides wherein:

$R^1$ is alkyl, alkenyl or alkynyl, each of which may-be substituted by alkoxy, haloalkoxy, alkylthio, halogen or phenyl optionally substituted by alkyl, haloalkyl, alkoxy, haloalkoxy, alkylthio or halogen; or is hydrogen;

$R^2$ and $R^3$, which may be the same or different, are as defined for $R^1$ in this embodiment, or are alkoxy, alkoxyalkoxy, benzyloxy, cyano or alkylcarbonyl;

$R^4$ is alkyl, alkenyl or alkynyl, each of which may be substituted by alkoxy, haloalkoxy, alkylthio, halogen or phenyl optionally substituted by alkyl, haloalkyl, alkoxy, haloalkoxy, alkylthio or halogen; or is hydroxy; halogen; cyano; acyl (preferably —C(=O)RC, —C(=S)Rc or —S(O)$_p R^c$, where $R^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio);

m is 0 or 1;

when present, $R^5$ is a group defined for $R^4$ in this embodiment;

A is a direct bond, —O—, —S—, —NR$^9$—, —CHR$^7$—or —O—CHR$^7$—, wherein when present, $R^9$ is alkyl, alkenyl, or alkynyl, each of which may be substituted by alkoxy, haloalkoxy, alkylthio, halogen or phenyl optionally substituted by alkyl, haloalkyl, alkoxy, haloalkoxy, alkylthio, or halogen; or is hydrogen; and $R^7$ is a group defined for $R^9$ in this embodiment, or is hydroxy; halogen; cyano; acyl; alkoxy; haloalkoxy or alkylthio;

A is attached to the 4 position of benzene ring M; and $R^6$ is phenyl or aromatic heterocyclyl, optionally substituted by one or more substituents, which may be the same or different, and may be selected from the list: hydroxy; halogen; cyano; acyl (preferably —C(=O)$R^c$, —C(=S)$R^c$ or —S(O)$_p R^c$, where $R^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio): amino; alkylamino; dialkylamino; alkyl; haloalkyl; R$^a$O-alkyl; acyloxyalkyl; cyano-oxyalkyl; alkoxy; haloalkoxy; alkylthio; carbocyclyl (preferably cyclohexyl or cyclopentyl) optionally substituted by alkyl, haloalkyl, alkoxy, haloalkoxy or alkylthio; and benzyl optionally substituted by alkyl, haloalkyl, alkoxy, haloalkoxy or alkylthio.

Most compounds of general formula I are novel. Therefore according to a second aspect, the invention provides compounds of formula I wherein $R^1$ is alkyl, alkenyl, alkynyl, carbocyclyl or heterocyclyl, each of which may be substituted, or is hydrogen;

$R^2$ and $R^3$, which may be the same or different, are any group defined for $R^1$, or together with the nitrogen to which they are attached may form a ring, which may be substituted;

$R^4$ is alkyl, alkenyl, alkynyl, carbocyclyl or heterocyclyl, each of which may be substituted;

m is 1;

$R^5$ is any group defined for $R^4$ attached to the 5-position of the benzene ring M;

R⁶ is optionally substituted carbo- or heterocyclyl; and

A is a direct bond; —O—; —S—; —NR⁹—, where R⁹ is alkyl, alkenyl, or alkynyl, each of which may be substituted by alkoxy, haloalkoxy, alkylthio, halogen or optionally substituted phenyl; —CHR¹⁷— or —O—CHR⁷—, where R⁷ is alkyl, alkenyl, or alkynyl, which may be substituted by alkoxy, haloalkoxy, alkylthio, halogen or phenyl optionally substituted by alkyl, haloalkyl, alkoxy, haloalkoxy or alkylthio; or is hydroxy; halogen; cyano; acyl; alkoxy; haloalkoxy; or alkylthio;

where —A—R⁶ is in the 4-position of the benzene ring M and the moiety depicted on the right side of linkage A is attached to R⁶;

or —A—R⁶ and R⁵ together with benzene ring M form an optionally substituted fused ring system.

Any alkyl group may be straight or branched and is preferably of 1 to 10 carbon atoms, especially 1 to 7 and particularly 1 to 5 carbon atoms.

Any alkenyl or alkynyl group may be straight or branched and is preferably of 2 to 7 carbon atoms and may contain up to 3 double or triple bonds which may be conjugated, for example vinyl, allyl, butadienyl or propargyl.

Any carbocyclyl group may be saturated, unsaturated or aromatic, and contain 3 to 8 ring-atoms. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Any heterocyclyl group may be saturated, unsaturated or aromatic, and contain 5 to 7 ring-atoms up to 4 of which may be hetero-atoms such as nitrogen, oxygen and sulfur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Any alkyl, alkenyl, alkynyl, carbocyclyl or heterocyclyl group, when substituted, may be substituted by one or more substituents, which may be the same or different, and may be selected from the list: hydroxy; mercapto; azido; nitro; halogen; cyano; acyl; optionally substituted amino: optionally substituted carbocyclyl; optionally substituted heterocyclyl; cyanato; thiocyanato; —SF₅; —OR$^a$; —SR$^a$ and —Si(R$^a$)₃, where R$^a$ is alkyl, alkenyl, alkynyl, carbocyclyl or heterocyclyl, each of which may be substituted. In the case of any carbocyclyl or heterocyclyl group the list includes additionally: alkyl, alkenyl and alkynyl, each of which may be substituted. Preferred substituents on any alkyl, alkenyl or alkynyl group are alkoxy, haloalkoxy or alkylthio, each containing 1 to 5 carbon atoms; halogen; or optionally substituted phenyl. Preferred substituents on any carbocyclyl or heterocyclyl group are alkyl, haloalkyl, alkoxy, haloalkoxy or alkylthio, each containing 1 to 5 carbon atoms; halogen; or optionally substituted phenyl.

In the case of any alkyl group or any unsaturated ring-carbon in any carbocyclyl or heterocyclyl group the list includes a divalent group such as oxo or imino, which may be substituted by optionally substituted amino, R$^a$ or —OR$^a$ (where R$^a$ is as defined above). Preferred groups are oxo, imino, alkylimino, oximino, alkyloximino or hydrazono.

Any amino group, when substituted and where appropriate, may be substituted by one or two substituents which may be the same or different, selected from the list: optionally substituted alkyl, optionally substituted amino, —OR$^a$ (where R$^a$ is as defined above) and acyl groups. Alternatively two substituents together with the nitrogen to which they are attached may form a heterocyclyl group, preferably a 5 to 7-membered heterocyclyl group, which may be substituted and may contain other hetero atoms, for example morpholino, thiomorpholino or piperidinyl.

The term acyl includes the residues of sulfur and phosphorus-containing acids as well as carboxylic acids. Typically the residues are covered by the general formulae —C(=X$^a$)R$^b$, —S(O)$_p$R$^b$ and —P(=X$^a$)(OR$^a$)(OR$^a$), where appropriate X$^a$ is O or S, R$^b$ is as defined for R$^a$, —OR$^a$, —SR$^a$, optionally substituted amino or acyl; and p is 1 or 2. Preferred groups are —C(=O)Rc, —C(=S)Rc, and —S(O)$_p$Rc where RC is alkyl, C₁ to C₅ alkoxy, C₁ to C₅ alkylthio, phenyl, heterocyclyl or amino, each of which may be substituted.

Complexes of compounds of the invention are usually formed from a salt of formula MAn₂, in which M is a divalent metal cation, e.g. copper, manganese, cobalt, nickel, iron or zinc and An is an anion, e.g. chloride, nitrate or sulfate.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof.

In cases where the compounds of the invention exist as optical isomers, the invention includes individual isomers as well as mixtures thereof.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), late tomato or potato blight (*Phytophthora infestans*), apple scab (*Venturia inaequalis*), and glume blotch (*Leptosphaeria noaorum*). Other fungi against which the compounds may be active include other powdery mildews, other rusts, and other general pathogens of Deuteromycete, Ascomycete, Phycomycete and Basidomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal, acaricidal, antimicrobial or antibacterial properties. Alternatively the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate: mono- or di-esters of phosphoric acid with fatty alcohol ethoxylates or alkyl phenol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine; the dialkyl sulfosuccinates, e.g. the sodium sulfonate of dioctyl succinate; acid derivatives of alkyl glycosides and alkylpolyglycosides materials and their metal salts, e.g. alkyl polyglycoside citrate or tartrate materials; or mono-, di- and tri-alkyl esters of citric acid and their metal salts.

Nonionic agents include condensation products of fatty acid esters, fatty alcohols, fatty acid amides or fatty-alkyl- or alkenyl-substituted phenols with ethylene and/or propylene oxide; fatty esters of polyhydric alcohol ethers, e.g. sorbitan fatty acid esters; condensation products of such esters with ethylene oxide, e.g. polyoxyethylene sorbitan fatty acid esters; alkyl glycosides, alkyl polyglycoside materials; block copolymers of ethylene oxide and propylene oxide; acetylenic glycols such as 2,4,7,9-tetramethyl-5-decyne-4,7-diol, ethoxylated acetylenic glycols; acrylic based graft copolymers; alkoxylated siloxane surfactants; or imidazoline type surfactants, e.g. 1-hydroxyethyl-2-alkylimidazoline.

Examples of a cationic surface-active agent include, for instance, an aliphatic mono-, di-, or polyamine as an acetate, naphthenate or oleate; an oxygen-containing amine such as an amine oxide, polyoxyethylene alkylamine or polyoxypropylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, an aerosol, a dispersion, an aqueous emulsion, a microemulsion, a dispersible concentrate, a dusting powder, a seed dressing, a fumigant, a smoke, a dispersible powder, an emulsifiable concentrate, granules or an impregnated strip. Moreover it can be in a suitable form for direct application or as a concentrate or primary composition which requires dilution with a suitable quantity of water or other diluent before application.

A dispersible concentrate comprises a compound of the invention dissolved in one or more water miscible or semi-water miscible solvents together with one or more surface active and/or polymeric material. Addition of the formulation to water results in the crystalisation of the active ingredient, the process being controlled by the surfactants and/or polymers resulting in a fine dispersion.

A dusting powder comprises a compound of the invention intimately mixed and ground with a solid pulverulent diluent, for example, kaolin.

An emulsifiable concentrate comprises a compound of the invention dissolved in a water-immiscible solvent which forms an emulsion or microemulsion on addition to water in the presence of an emulsifying agent.

A granular solid comprises a compound of the invention associated with similar diluents to those that may be employed in dusting powders, but the mixture is granulated by known methods. Alternatively it comprises the active ingredient absorbed or coated on a pre-formed granular carrier, for example, Fuller's earth, attapulgite, silica or limestone grit.

Wettable powders, granules or grains usually comprise the active ingredient in admixture with suitable surfactants and an inert powder diluent such as clay or diatomaceous earth.

Another suitable concentrate is a flowable suspension concentrate which is formed by grinding the compound with water or other liquid, surfactants and a suspending agent.

The concentration of the active ingredient in the composition of the present invention, as applied to plants is preferably within the range of 0.0001 to 1.0 percent by weight, especially 0.0001 to 0.01 percent by weight. In a primary composition, the amount of active ingredient can vary widely and can be, for example, from 5 to 95 percent by weight of the composition.

In use a compound of the invention is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth, as this is the time when the plant can be most severely damaged. The spray or dust can conveniently contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to harvested fruits, vegetables or seeds to prevent infection during storage.

In addition, the compounds of the invention can be applied to plants or parts thereof which have been genetically modified to exhibit a trait such as fungal and/or herbicidal resistance.

In addition the compounds of the invention can be used to treat fungal infestations in timber and in public health applications. Also the compounds of the invention can be used to treat fungal infestations in domestic and farm animals.

Compounds of the invention may be prepared, in known manner, in a variety of ways.

Compounds of general formula I may be prepared from compounds of general formula II according to Scheme 1. The following reaction conditions may be used to effect conversion:

a) reaction with $R^2R^3NC(R^1)(OR)_2$, where R is a group such as alkyl;
b) reaction with $ROC(R^1)=NCN$;
c) when $R^1$ is hydrogen, by reaction with $H(C=O)NR^2R^3$ in the presence of $POCl_3$ or $SOCl_2$; or
d) in two steps by reaction with phosgene to form the isocyanate and then treatment with $R^2R^3N(C=O)R^1$.

Scheme 1

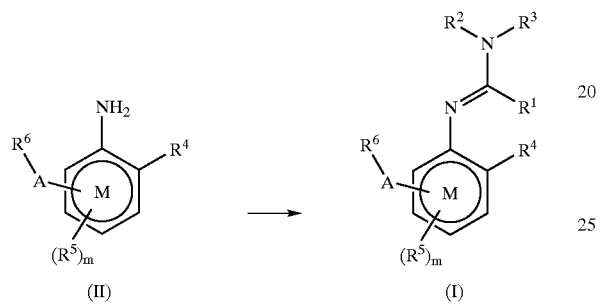

In addition, groups $R^2$ and $R^3$ in compounds of general formula I can be converted to other groups defined for $R^2$ and $R^3$, by treatment with an appropriate amine or by acylation or alkylation when $R^2$ or $R^3$ is hydrogen.

Compounds of general formula II may be prepared by reduction of the nitro group in compounds of formula III according to reaction scheme 2. Preferred reaction conditions comprise reaction with stannous chloride in concentrated hydrochloric acid.

Scheme 2

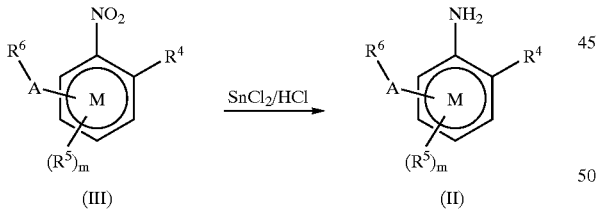

Compounds of formula IIa, i.e. compounds of general formula II where A is a direct bond, may be prepared according to reaction scheme 3, where $X^V$ is a leaving group.

Scheme 3

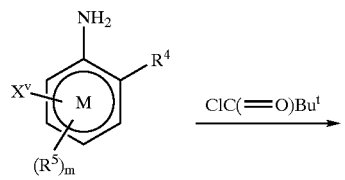

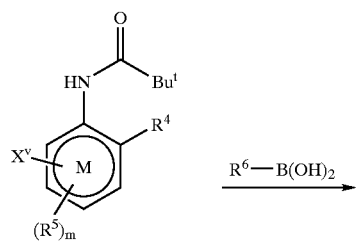

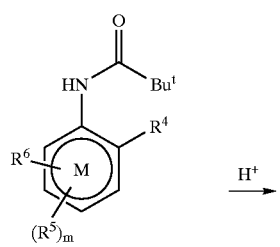

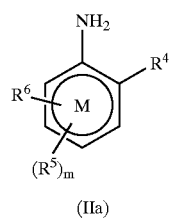

Compounds of formula IIb, i.e. compounds of general formula II where $R^4$ is halogen, may be prepared according to scheme 4 where XT represents halogen. When $R^4$ is bromine preferred reaction conditions comprise stirring with bromine in a suitable solvent.

Scheme 4

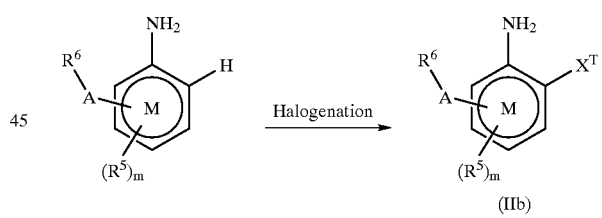

Compounds of formula IIc, i.e. compounds of general formula II where A is $NHC(=O)$—; compounds of formula IId, i.e. compounds of formula II where A is a direct bond and $R^6$ is optionally substituted phthalimido, where the curved line connecting the 3 and 4 positions of the phthalimido group represents the optionally substituted carbocyclic ring; and compounds of formula IIe, i.e. compounds of general formula II where A is a direct bond and $R^6$ is pyrrolyl, optionally substituted at the 2 and 5 positions by one or more groups R which may be the same or different; may be prepared from compounds of formula IV according to methodology shown in reaction scheme 5. For certain compounds of formula IV, protection/deprotection of the amino group ortho to $R^4$ may be required to improve yields.

Scheme 5

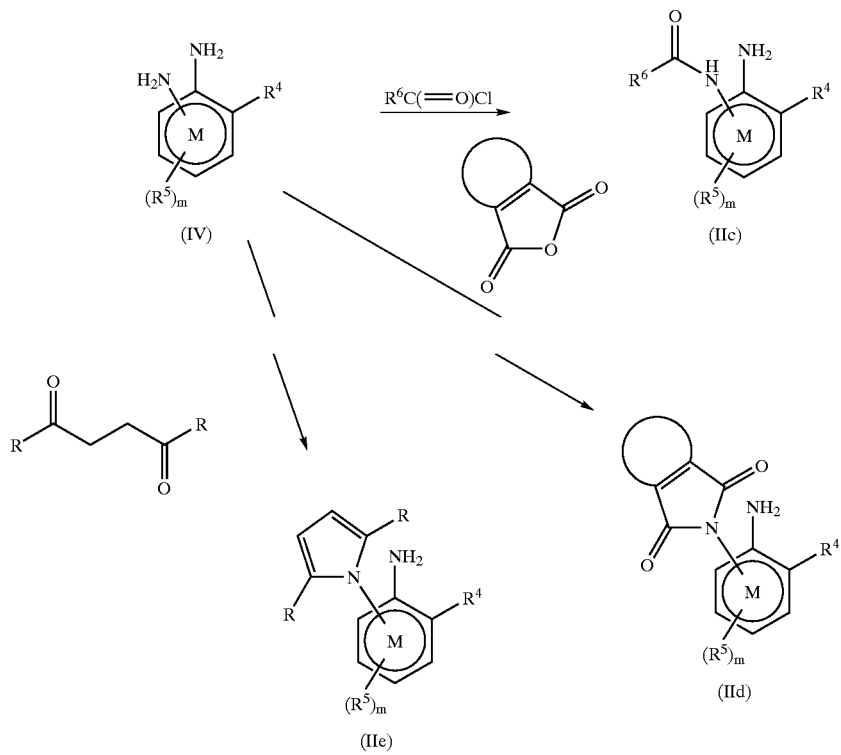

Compounds of formula IIIa, i.e. compounds of general formula III where A is a group $A^Z$, may be prepared by reacting compounds of formula V with compounds of formula VI according to reaction scheme 6. AZ is a group which, in compound V, forms an anion under basic conditions. $A^Z$ is alternatively a basic primary or secondary nitrogen atom. $X^Z$ is a leaving group, preferably halogen. When $A^Z$ is oxygen, preferred reaction conditions comprise treating V with sodium hydride followed by addition of VI. When $A^Z$ is sulfur preferred reaction conditions comprise reacting V with VI in the presence of a tertiary amine base such as ethyldiisopropylamine. When $A^Z$ is —$CHR^7$—, preferred reaction conditions comprise treating V with potassium tert-butoxide in dimethylformamide at low temperature. When $A^Z$ is a basic nitrogen atom, no base is required.

Scheme 6

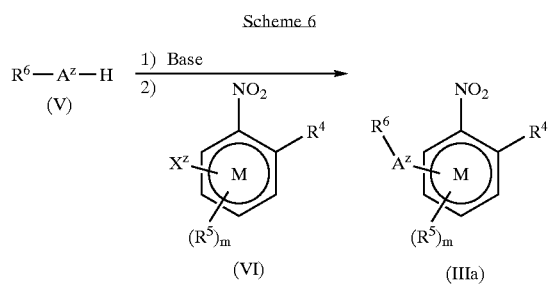

Compounds of formula IIIb, i.e. compounds of general formula III where A is a group $A^W$, may be prepared by reacting compounds of formula VII with compounds of formula VIII according to reaction scheme 7. $A^W$ is a group which, in compound VII, forms an anion under basic conditions. $X^W$ is a leaving group, preferably halogen. Preferred basic conditions comprise reaction of VII with potassium carbonate or sodium hydride followed by addition of VII.

Scheme 7

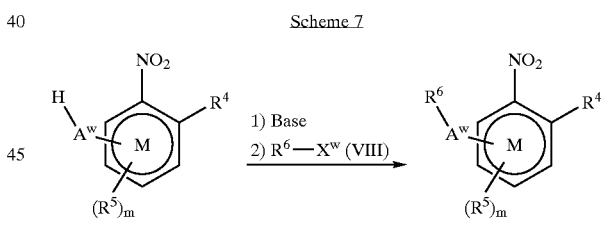

Compounds of formula IIIc, i.e. compounds of general formula III where A is O, may be prepared by reacting compounds of formula IX with boronic acids of formula X according to Scheme 8. Preferred reaction conditions comprise reaction with copper acetate and triethylamine.

Scheme 8

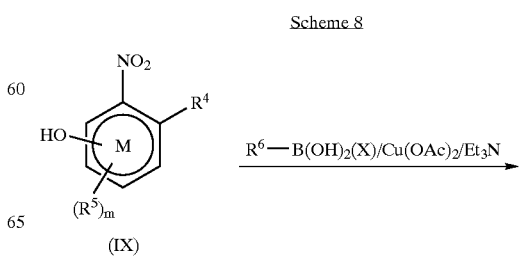

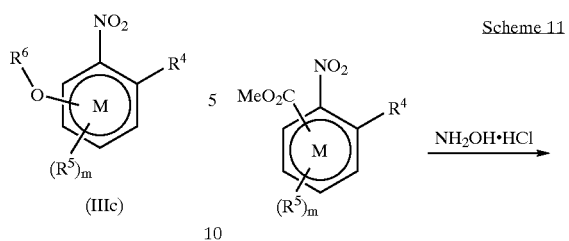

(IIIc)

Compounds of formula IIId, i.e. compounds of formula III where A is a direct bond may be prepared according to reaction scheme 9 from compounds of formula XI where $X^Z$ is a leaving group, preferably halogen.

Scheme 9

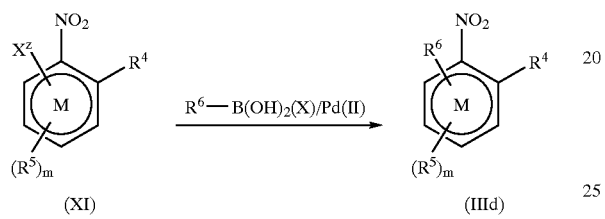

(XI)        (IIId)

Compounds of formula III where A is a direct bond and $R^6$ is a heterocyclyl can be prepared using a variety of methods known to a skilled chemist (for example see "Comprehensive Heterocyclic Chemistry", Vols 1–7, A. R. Katritzky and C. W. Rees). By way of example, routes to compounds of formula III containing a 1,2,4-oxadiazol-3-yl group (compound IIIe) and a 1,3,4-oxadiazol-2-yl group (compound IIIf) are shown in schemes 10 and 11.

Scheme 10

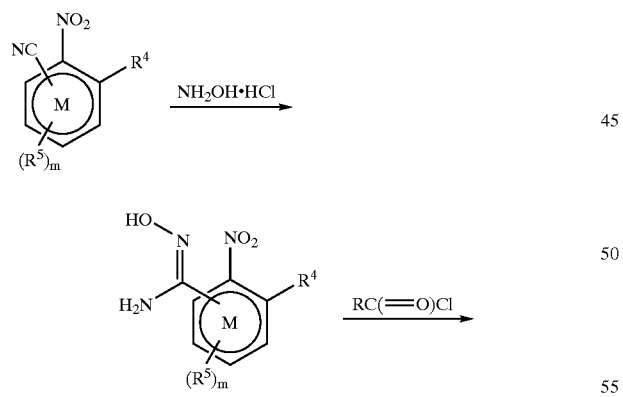

(IIIe)

Scheme 11

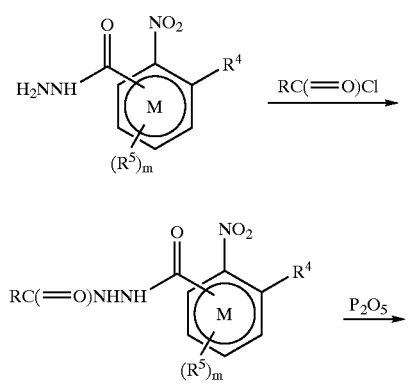

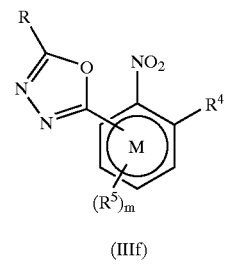

(IIIf)

Alternatively, using similar chemistry to that described above, compounds of formula I can be prepared by introducing $R^6$ after formation of the amidine moiety.

In particular, we have found that treating compounds of formula XII to the reaction conditions of Scheme 7 gives compounds of formula Ia, i.e. compounds of general formula I where A is oxygen, in particularly high yield (see Scheme 12). Compounds of formula XII may be prepared by methods similar to those described in *Tetrahedron Letters*, 38 (31) 5403–5406.

Scheme 12

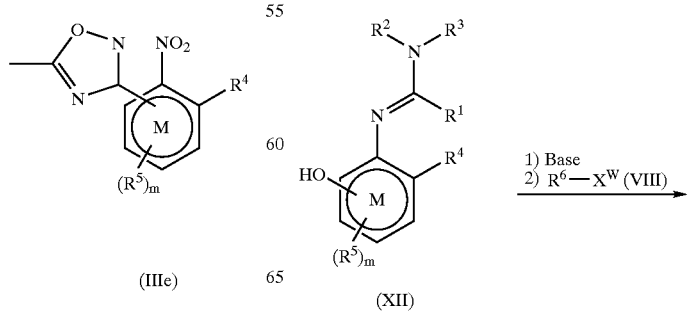

(XII)

-continued

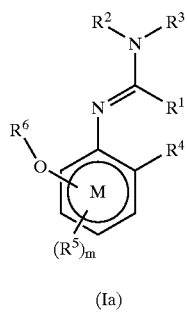

(Ia)

Some compounds of general formula XII are novel, therefore according to a third aspect the invention provides compounds of general formula XIIa,

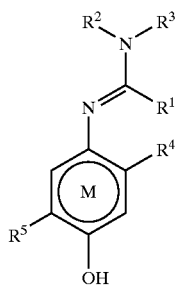

(XIIa)

where
R¹ is alkyl, alkenyl, alkynyl, carbocyclyl or heterocyclyl, each of which may be substituted, or is hydrogen;
R² and R³, which may be the same or different, are any group defined for R¹; cyano; acyl; —OR$^a$ or —SR$^a$, where R$^a$ is alkyl, alkenyl, alkynyl, carbocyclyl or heterocyclyl, each of which may be substituted; or R² and R³, or R² and R¹, together with their interconnecting atoms may form a ring, which may be substituted;
R⁴ is alkyl, alkenyl, alkynyl, carbocyclyl or heterocyclyl, each of which may be substituted; and
R⁵ is any group defined for R⁴;
with the proviso that R⁵ is not tert-butyl.

Other methods will be apparent to the chemist skilled in the art, as will be methods for preparing starting materials and intermediates.

In addition, compounds of the invention may be prepared using combinatorial chemistry methodology.

The invention is illustrated in the following Examples. Structures of isolated, novel compounds were confirmed by N.M.R. and/or other appropriate analyses. Proton N.M.R. spectra (¹H N.M.R.) were determined in deuterochloroform and chemical shifts (δ) are quoted in parts per million downfield of tetramethylsilane.

EXAMPLE 1

N,N-Dimethyl-N'-[4-(3-trifluoromethylbenzylthio)-2,5-xylyl]formamidine (Compound 3)

The product from stage b) (1.0 g) and N,N-dimethylformamide dimethylacetal (1.0 ml) were heated at 100° C. for 4 hours. On cooling the mixture was purified by silica gel chromatography eluting with diethyl ether to give the title compound, ¹H N.M.R. δ(ppm) 2.15 (s, 3H, ArCH₃), 2.20 (s, 3H, ArCH₃), 3.00 (s, 6H, N(CH₃)₂), 3.95 (s, 2H, SCH₂).

Preparation of Starting Materials a) 2-Nitro-5-(3-trifluoromethylbenzylthio)-p-xylene A mixture of 3-trifluoromethylbenzyl mercaptan (3.42 g), diisopropylethylamine (2.3 g) and 3-chloro-6-nitro-p-xylene (3.0 g) in dry N-methylpyrrolidinone (20 ml) was heated at 130° C. for 6 hours. On cooling, the mixture was poured into ice-water and the resulting mixture was filtered to give a solid which was washed with ice-water and then air dried. The solid was purified by silica gel chromatography eluting with light petroleum (60–80° C.)/ethyl acetate (9:1) to give the title product as a solid, m.p. 85–7° C.

b) 4-(3-Trifluoromethylbenzylthio)-2,5-xylidine

To a stirred mixture of stannous chloride (10.8 g) in concentrated hydrochloric acid (24 ml) and ethanol (50 ml) was added the product from stage a) above (2.46 g) and the mixture was heated at 75° C. for 2 hours. On cooling potassium hydroxide solution was added slowly with cooling. The mixture was extracted with diethyl ether (x3) and the combined extracts were washed with brine, dried (MgSO₄), filtered and evaporated to dryness to give a crude residue which was purified by silica gel chromatography eluting with light petroleum (b.p. 60–80° C.)/ethyl acetate (3:1) to give the title product, m.p. 58–60° C.

EXAMPLE 2

N,N-Diethyl-N'-[4-(3-trifluoromethylphenoxy)-2,5-xylyl]formamidine (Compound 37)

Under an atmosphere of nitrogen, phosphorous oxychloride (2.18 g) in dry diethyl ether (3 ml) was added dropwise to a stirred solution of N,N-diethylformamide (1.43 g) in dry diethyl ether (3 ml) and stirring continued for 20 minutes. Stirring was stopped and the mixture allowed to form two layers. The upper ether layer was removed by decanting, and the lower layer was washed with diethyl ether (x3). The product from stage b) (2 g) in dry diethyl ether (4 ml) was then added dropwise. After addition the mixture was stirred vigorously for 1 hour at room temperature. The upper ether layer was removed by decanting and the lower layer was washed with ether (x2). The lower layer was poured into water and the mixture adjusted to pH 9 with sodium carbonate solution. The mixture was extracted with diethyl ether (x3) and the combined extracts were dried (MgSO₄), filtered and evaporated to dryness to give a crude oil which was purified by silica gel chromatography eluting with diethyl ether to give the title compound, 1H N.M.R. δ(ppm) 1.20 (t, 6H, CH₂CH₃), 2.10 (s, 3H, ArCH₃), 2.20 (s, 3H, ArCH₃), 3.30–3.50 (br, 4H, CH₂CH₃).

Preparation of Starting Materials a) 2-Nitro-5-(3-trifluoromethylphenoxy)-p-xylene To a suspension of sodium hydride (0.4 g of 60% in oil) in dry N-methylpyrrolidinone (10 ml) was slowly added 3-trifluoromethylphenol (1.62 g). When effervescence had ceased, 3-chloro-6-nitro-p-xylene (1.85 g) was added and the mixture stirred at 120–40° C. for 5 hours. On cooling, the mixture was poured into water and the mixture extracted with diethyl ether (x3). The combined ether extracts were dried (MgSO₄), filtered and evaporated to give the title compound as a solid, m.p. 68–71° C.

b) 4-(3-Trifluoromethylphenoxy)-2,5-xylidine

This compound was prepared in similar fashion to the product from Example 1, stage b).

EXAMPLE 3

N-Ethyl-N-methyl-N'-[4-(3-trifluoromethylphenoxy)-2,5-xylyl]formamidine (Compound 45)

A mixture of the product from Example 4 (1 g) and methylethylamine (0.885 g) in acetonitrile (20 ml) was stirred at room temperature for 1.5 hours. The solvent was removed in vacuo and water added. The mixture was extracted with diethyl ether (x3) and the combined ether extracts dried (MgSO$_4$), filtered and evaporated to dryness. The crude residue was purified by silica gel chromatography eluting with ethyl acetate/light petroleum (b.p. 40–60° C.) (4:6) to give the title compound, 1H N.M.R. δ(ppm) 1.20 (t, 3H, CH$_2$CH$_3$), 2.10 (s, 3H, ArCH$_3$), 2.20 (s, 3H, ArCH$_3$), 3.00 (s, 3H, NCH$_3$), 3.40 (br, 2H, NCH$_2$).

EXAMPLE 4

N-Cyano-N'-[4-(3-trifluoromethylphenoxy)-2,5-xylyl]formamidine (Compound 44)

To a solution of the product from Example 2 stage b) (2 g) in ethanol (5 ml) was added dropwise ethyl cyanoimidate (0.7 g) at room temperature and stirring continued for 2 hours at room temperature. The ethanol was removed in vacuo to give a crude residue which was purified by trituration with light petroleum (b.p. 40–60° C.) followed by silica gel chromatography eluting with ethyl acetate/light petroleum (b.p. 40–60° C.) (4:6) to give the title product, m.p. 138–40° C.

EXAMPLE 5

N,N-Dimethyl-N'-[4-(3-phenyl-1,2,4-thiadiazol-5-yloxy)-2,5-xylyl]formamidine (Compound 48)

To a suspension of the starting material (see below) (0.57 g) in dimethylformamide (10 ml) was added potassium carbonate (0.62 g) and the solution stirred at room temperature for 40 minutes. 5-Bromo-3-phenyl-1,2,4-thiadiazole (0.72 g) was added and the mixture stirred at 60° C. for 3 hours. On cooling the mixture was poured into water (150 ml) and extracted with diethyl ether (3×70 ml). The combined ether extracts were washed with water (20 ml), dried (MgSO$_4$), filtered and evaporated to dryness to give a crude solid which was purified by silica gel chromatography eluting with diethyl ether to give the title compound as a solid, m.p. 100–5° C.

Preparation of Starting Materials

N,N-Dimethyl-N'-{4-hydroxy-2,5-xylyl}formamidine

This compound was prepared from 4-amino-2,5-dimethylphenol in similar fashion to Examples 1, 2 or 3, m.p. 212° C.

EXAMPLE 6

N,N-Dimethyl-N'-[4-(3-trifluoromethylphenoxy)-2,6-xylyl]formamidine (Compound 20)

This compound was prepared from the product of stage b) below and dimethylformamide dimethylacetal according to the method of Example 1, $^1$H N.M.R. δ(ppm) 2.15 (s, 6H, ArCH$_3$), 3.00 (s, 6H, N(CH$_3$)$_2$).

Preparation of Starting Materials a) 2-Nitro-5-(3-trifluoromethylphenoxy)-m-xylene A mixture of 3,5-dimethyl-4-nitrophenol (1.67 g), 3-trifluoromethylbenzene boronic acid (3.8 g), copper (1 acetate (1.82 g) and triethylamine (2.02 g) in dichloromethane (50 ml) was stirred at room temperature for 48 hours. The mixture was evaporated to dryness and purified by silica gel chromatography eluting with light petroleum (b.p. 60–80° C.)/ethyl acetate (19:1) to give the title product as an oil.

b) 4-(3-Trifluoromethylphenoxy)-2,6-xylidine

This compound was prepared from the product of stage a) above according to the method of Example 1, stage b).

EXAMPLE 7

N,N-Dimethyl-N'-16-bromo-4-(3-trifluoromethylphenoxy)-2.5-xylyl]formamidine (Compound 12)

The title product was prepared from the product of stage c) below and dimethylformamide dimethylacetal according to Example 1, $^1$H N.M.R. δ(ppm) 2.17 (s, 3H, ArCH$_3$), 2.22 (s, 3H, ArCH$_3$), 3.05 (s, 6H, N(CH$_3$)$_2$).

Preparation of Starting Materials a) 2-Nitro-5-(3-trifluoromethylphenoxy)-α-xylene The title product was prepared from 2,5-dimethyl-4-nitrophenol and 3-trifluoromethylbenzene boronic acid according to Example 6, stage a).

b) 4-(3-Trifluoromethylphenoxy)-2,5-xylidine

The title product was prepared from the product of stage a) according to Example 1, stage b).

c) 6-Bromo-4-(3-trifluoromethylphenoxy)-2,5-xylidine

To a stirred solution of the product from stage b) above (1.12 g) in dichloromethane (20 ml) was added dropwise bromine (0.64 g) in dichloromethane (5 ml) at 0° C. The mixture was washed with sodium bicarbonate solution, dried (MgSO$_4$), filtered and evaporated to give a crude oil which was purified by silica gel chromatography eluting with ethyl acetate/light petroleum (b.p. 60–80° C.) (1:4) to give the title product.

EXAMPLE 8

N,N-Dimethyl-N'-[4-(3-trifluoromethylphenyl)-2,5-xylyl]formamidine (Compound 53)

The title product was prepared from the product of stage c) below and dimethylformamide dimethylacetal according to Example 1, $^1$H N.M.R. δ(ppm) 2.00 (s, 3H, ArCH$_3$), 2.20 (s, 3H, ArCH$_3$), 3.00 (s, 6H, (NCH$_3$)$_2$).

Preparation of Starting Materials a) N-(4-Bromo-2,5-xylyl)pivalamide

To a solution of 4-bromo-2,5-xylidine (8 g) in pyridine (60 ml) was added pivaloyl chloride (4.7 ml) at room temperature. After 30 minutes, the mixture was poured into dilute hydrochloric acid/ice solution. The precipitate was filtered and washed with water to give the title product.

b) N-(4-(3-Trifluoromethylphenyl)-2,5-xylyl)pivalamide

To a solution of the product of stage a) (9.1 g) in dimethoxyethane (14 ml) was added triphenylphosphinepalladium (II) chloride (catalytic amount) and stirred for 10 minutes. 3-Trifluoromethyphenylboronic acid (6.03 g), sodium bicarbonate (8.1 g) and water (102 ml) were added and the mixture heated under reflux for 4 hours. On cooling 1 N sodium hydroxide solution (94 ml) was added the mixture extracted with ethyl acetate. The organic extracts were washed with saturated sodium chloride solution, dried (MgSO$_4$) and concentrated to give the title product.

c) 4-(3-Trifluoromethylphenyl)-2,5-xylidine

The product from stage b) (10.4 g) in glacial acetic acid (36 ml) was treated with hydrochloric acid (24.5 ml of 15% solution) at 70° C. The mixture was stirred for 3 days at 100° C. On cooling, water was added and the mixture extracted with ethyl acetate. The organic phase was washed with sodium bicarbonate solution, dried (MgSO$_4$) and concentrated to give the title product.

EXAMPLE 9

N,N-Dimethyl-N'-[4-(3-trifluoromethylbenzyl)-2,5-xylyl]formamidine (Compound 264)

The title compound was prepared from the product of stage d) below in similar fashion to Example 1, m.p. 75–7° C.

Preparation of Starting Materials a) 2-Nitro-5-(α-cyano-3-trifluoromethyl benzyl)-p-xylene The title product was prepared from 2-chloro-5-nitro-p-xylene and 3-trifuoromethylbenzyl cyanide according to the methodology in J. Med. Chem., 40, 3942 (1997).

b) 2-Nitro-(5-(3-trifluoromethylbenzoyl)-p-xylene

Potassium tert-butoxide (1.12 g) was added to a solution of the product from stage a) (3.3 g) in dry dimethylformamide (30 ml) at 0° C. and stirred at 0° C. for 5 minutes. Hydrogen peroxide (3.5 ml, 30%) was added dropwise and stirring continued for 6 hours at approximately 3° C. The reaction mixture was allowed to stand at room temperature for 2 days. The reaction mixture was poured into dilute hydrochloric acid (500 ml), and sodium metabisulfite was added. The mixture was extracted with diethyl ether (2×200 ml), washed with water (2×20 ml), dried (MgSO$_4$) and concentrated to give a crude product. Trituration from light petroleum (b.p. 40–60° C.) gave a solid which was recrystallised from diisopropyl ether to give the title product.

c) 2-Nitro-5-(3-trifluoromethylbenzyl)-p-xylene

To a solution of the product of stage b) (1 g) in dichloromethane (20 ml) at 0° C. was added a solution of trifluoromethane sulfonic acid (0.6 ml) in dichloromethane (10 ml). Triethylsilane (0.8 ml) in dichloromethane (10 ml) was added and stirred at 0° C. for 10 minutes. A further portion of trifluoromethane sulfonic acid (0.6 ml) was added followed by a further portion of triethylsilane (0.8 ml). The mixture was allowed to warm to room temperature and stirred for 1 hour. The mixture was poured into saturated sodium bicarbonate solution (100 ml) and the inorganic solid filtered. The layers were separated and the aqueous layer extracted with dichloromethane (2×50 ml). The combined organic layers were evaporated and recrystallised to give a solid, m.p. 75–7° C.

d) 4-(3-Trifluoromethylbenzyl)-2,5-xylidine

The title compound was prepared from the product of stage c) according to Example 1 stage b).

EXAMPLE 10

N,N-Dimethyl-N'-[4-(4-fluorobenzamido)-2,5-xylyl]formamidine (Compound 98)

The title compound was prepared from the starting material in similar fashion to Example 1, m.p. 166–8— C.

Preparation of Starting Materials

N-(4-Amino-2,5-xylyl)-4-fluorobenzamide

To a solution of p-xylylenediamine (3.0 g) and ethyldiisopropylamine (3.8 ml) in dichloromethane (300 ml) at 0° C., was added dropwise 4-fluorobenzoyl chloride (3.5 g). The mixture was warmed to room temperature and stirring continued for 4 hours. Water (200 ml) was added and the mixture was stirred for 30 minutes. The mixture was filtered, washing through with water and dichloromethane. The organic phase was washed with water, dried (MgSO$_4$) and evaporated to give a solid, m.p. 174–6° C.

EXAMPLE 11

N,N-Dimethyl-N'-(4-phthalimido-2,5-xylyl)formamidine (Compound 80)

The title compound was prepared from the starting material in similar fashion to Example 1, m.p. 170–3° C.

Preparation of Starting Materials

N-{4-Amino-2,5-xylyl}phthalimide

To a solution of p-xylylenediamine (1.0 g) in N-methylpyrrolidinone was added phthalic anhydride (1.1 g) in N-methylpyrrolidinone (10 ml). The mixture was heated at 150° C. for 4 hours. On cooling, the mixture was poured into water and then filtered. The cake was washed with water and dried, m.p. 167–9° C.

EXAMPLE 12

N,N-Dimethyl-N'-[4-(2,5-dimethyl-1-pyrrolyl)-2,5-xylyl]formamidine (Compound 79)

The title compound was prepared from stage c) below in similar fashion to Example 1, m.p. 90–1° C.

Preparation of Starting Materials a) N-(4-Amino-2,5-xylyl)acetamide

To a solution of p-xylenediamine (2.0 g) in dichloromethane (200 ml) maintained below 10° C. was added N,N-diisopropylamine (2.52 ml) followed by the dropwise addition of acetylchloride (1.15 g). The mixture was allowed to attain room temperature and stirred overnight. Water (120 ml) was added and the suspension filtered. The filtered solid was washed with dichloromethane (2×100 ml) and water (100 ml). All filtrates were combined and the organic layer separated. The organic layer was washed with water, dried (MgSO$_4$) and evaporated to give the title product as a solid, m.p. 133–5° C.

b) N-[4-(2,5-Dimethyl-1-pyrrolyl)-2,5-xylyl]acetamide

The product from stage a) 1.0 g) was added to acetonylacetone (0.7 ml) and the mixture heated at 140° C. for 4 hours. On cooling, the mixture was dissolved in dichloromethane and the solution filtered through (MgSO$_4$). Concentration gave a crude product which was purified by silica gel chromatography eluting with diethyl ether, to give the title product.

c) 2,5-Dimethyl-4-(2,5-dimethyl-1-pyrrolyl)aniline

A mixture of the product from stage b) (0.6 g), aqueous sodium hydroxide solution (10 ml, 10%) and ethanol (30 ml) was heated under reflux for 24 hours. On cooling, the mixture was extracted with diethyl ether (x2). The combined diethyl ether extracts were water washed, dried (MgSO$_4$) and concentrated to give a crude product. Filtration through silica gave the title product.

EXAMPLE 13

N,N-Dimethyl-N'-[4-(2-benzo[b]thiophenyl)-2,5-xylyl)formamidine (Compound 187)

The title compound was prepared from stage b) below in similar fashion to Example 1, m.p. 67–8° C.

Preparation of Starting Materials a) 2-(4-Nitro-2,5-xylyl)benzo[b]thiophene

A mixture of 2-bromo-5-nitro-p-xylene (200 g), 2-benzo[b]thiopheneboronic acid (200 g), (Ph$_3$P)$_4$Pd (0.36 g) in toluene (60 ml) and ethanol (22 ml) was heated to reflux overnight. Ethyl acetate and water were added and the organic phase was separated. The organic phase was washed with water, dried (MgSO$_4$) and filtered through a pad of silica to give the title product.

b) 2,5-Dimethyl-4-(2-benzo[b]thiophenyl)aniline

The title compound was prepared from the product of stage a) above according to Example 1 stage b).

EXAMPLE 14

N,N-Dimethyl-N'-{4-[5-(4-chlorophenyl)-1,2,4-oxadiazol-3-yl]-2-tolyl}formamidine (Compound 179)

The title compound was prepared from the product of stage c) below according to Example 1, m.p. 136–7° C.

Preparation of Starting Materials a) 3-Methyl-4-nitrobenzamide Oxime

To a solution of 3-methyl-4-nitrobenzonitrile (5 g) in ethanol (100 ml) at room temperature was added hydroxylamine hydrochloride (2.25 g) followed by triethylamine (4.5 ml). The mixture was heated under reflux for 2.5 hours. On cooling the mixture was evaporated to a third of its original volume and poured on to water (200 ml). The mixture was filtered to give the title product as a solid, m.p. 127–9° C.

b) 5-(4-Chlorophenyl)-3-(3-methyl-4-nitrophenyl)-1,2,4-oxadiazole

To a solution of the product from stage a) (1.9 g) and triethylamine (1.62 ml) in dichloromethane 150 ml) at room temperature was added 4-chlorobenzoyl chloride (2.05 g). The mixture was stirred at room temperature for 2 hours and then washed with water. Toluene (100 ml) was added and the mixture was heated under Dean and Stark conditions for 5 hours. On cooling the mixture was filtered and concentrated. Trituration with diisopropylamine and light petroleum (b.p. 40–60° C.) gave the title product, m.p. 145–7° C.

c) 4-[5-(4-Chlorophenyl)-1,2,4-oxadiazol-3-yl]-2-methylaniline

The title compound was prepared from the product of stage b) according to Example 1 stage b).

EXAMPLE 15

N,N-Dimethyl-N'-[4-(5-tert-butyl-1,3,4-oxadiazol-2-yl)-2-methylphenyl]formamidine (Compound 211)

The title compound was prepared from the product of stage c) below according to Example 1, m.p. 79–80° C.

Preparation of Starting Materials a) N-(3-Methyl-4-nitrobenzoyl)-N'-pivalolyhydrazine

To a solution of 3-methyl-4-nitrobenzoylhydrazine (3.9 g) in dichloromethane (100 ml) was added triethylamine (3.06 ml) followed by pivaloyl chloride (2.6 ml). The mixture was stirred at room temperature for 2 hours. The mixture was washed with water, dried (MgSO$_4$) and concentrated. Trituration with light petroleum (b.p. 60–80° C.) gave the title product, m.p. 125–7° C.

b) 5-tert-Butyl-2-(3-methyl-4-nitrophenyl)-1,3,4-oxadiazole

The product prepared in stage a) (5.0 g) was stirred in toluene (200 ml) and treated with phosphorous pentoxide (10 g). The mixture was heated under reflux for 2 hours and then poured onto ice-water. The mixture was extracted with diethyl ether, the extract dried (MgSO$_4$) and concentrated. The residue was purified by silica gel chromatography eluting with diethyl ether/light petroleum (b.p. 60–80° C.) to give the title product, m.p. 123–5° C.

c) 2-(4-Amino-3-methyl)-5-tert-butyl-1,3,4-oxadiazole

The title compound was prepared from the product of stage b) according to Example 1 stage b).

EXAMPLE 16

N—Cyano-N-methyl-N'-[4-(4-chloro-3-trifluoromethylphenoxy)-2-xylyl]formamidine (Compound 373)

The product from stage c) (0.4 g) in tetrahydrofuran (10 ml) was treated with sodium hydride (0.05 g). Iodomethane (0.075 ml) was added and the mixture was stirred. The mixture was quenched with water and extracted with dichloromethane. The extracts were dried (MgSO$_4$) and evaporated. The residue product was purified by silica gel chromatography to give the title product, $^1$H N.M.R. δ(ppm) 2.10 (s, 3H, ArCH$_3$), 2.20 (s, 3H, ArCH$_3$) and 3.35 (s, 3H, NCH$_3$).

EXAMPLE 17
N-Cyano-N'-[4-(4-chloro-3-trifluoromethylphenoxy)-2,5-xylyl]formamidine (Compound 397)

The title compound was prepared according to Example 4 from the product of stage b) above, m.p. 111–4° C.

Preparation of Starting Materials a) 2-Nitro-5-(4-chloro-3-trifluoromethylphenoxy)-p-xylene The title compound was prepared according to Example 2 stage a).

b) 4-(4-Chloro-3-trifluoromethylphenoxy)-2,5-xylidine

The title compound was prepared according to Example 1 stage b) from the product of stage a) above.

The following compounds of formula Ia (see Table 1), i.e. compounds of general formula I where —A—$R^6$ is para to the amidine moiety, may be prepared by methods analogous to those of Examples 1 to 17. Where the moiety depicted on the right side of linkage A is attached to $R^6$;

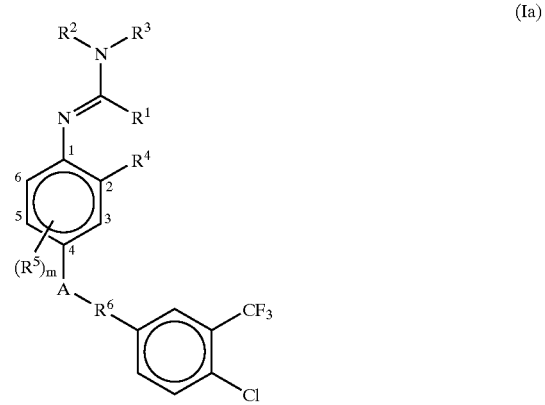

(Ia)

TABLE 1

| Cmp | $R^1$ | $R^2$ | $R^3$ | $R^4$ | $(R^5)_m$ | A | $R^6$ | m.p./° C. |
|---|---|---|---|---|---|---|---|---|
| 1 | H | Me | Me | Me | 5-Me | O | 3-$CF_3$—phenyl | 49–50 |
| 2 | Me | Me | Me | Me | 5-Me | O | 3-$CF_3$—phenyl | oil |
| 3 | H | Me | Me | Me | 5-Me | —$SCH_2$— | 3-$CF_3$—phenyl | oil |
| 4 | H | Me | Me | Me | 5-Me | S | 3-$CF_3$—phenyl | oil |
| 5 | Me | Me | Me | Me | 5-Me | —$SCH_2$— | 3-$CF_3$—phenyl | oil |
| 6 | Me | Me | Me | Me | 5-Me | S | 3-$CF_3$—phenyl | oil |
| 7 | H | Me | Me | Me | 5-Me | O | 3-Cl—phenyl | oil |
| 8 | H | Me | Me | Me | 5-Me | O | 3-$Bu^t$—phenyl | 69–71 |
| 9 | H | Me | Me | Me | 5-Me | O | 4-tolyl | oil |
| 10 | Me | Me | Me | Me | 5-Me | —$OCH_2$— | 3-$CF_3$—phenyl | oil |
| 11 | H | Me | Me | Me | 5-Me | —$OCH_2$— | 3-$CF_3$—phenyl | 50–4 |
| 12 | H | Me | Me | Me | 5-Me, 6-Br | O | 3-$CF_3$—phenyl | oil |
| 13 | H | Me | Me | Me | — | O | 3-$CF_3$—phenyl | oil |
| 14 | H | Me | Me | $CF_3$ | — | O | 3-$CF_3$—phenyl | oil |
| 15 | H | Me | Me | Br | 5-OMe | O | 3-$CF_3$—phenyl | 68–70 |
| 16 | H | Me | Me | Me | 5-Me | —OCH(Me)— | 3-$CF_3$—phenyl | 97–9 |
| 17 | H | Me | Me | Me | 5-Me | —$OCH_2$— | 3-PhO—phenyl | oil |
| 18 | H | Me | Me | Br | 3-Me, 6-Br | O | 3-$CF_3$—phenyl | oil |
| 19 | H | Me | Me | Br | 5-Me | O | 3-$CF_3$—phenyl | oil |
| 20 | H | Me | Me | Me | 6-Me | O | 3-$CF_3$—phenyl | oil |
| 21 | H | Me | Me | Me | 5-$Pr^i$ | O | 3-$CF_3$—phenyl | oil |
| 22 | H | Me | Me | Me | 5-Me | O | 2-biphenylyl | oil |
| 23 | H | Me | Me | Me | 5-Me | O | 3-F—phenyl | oil |
| 24 | H | Me | Me | Me | 5-Me | O | 4-$CF_3$—phenyl | oil |
| 25 | H | Me | Me | Me | 5-Me | O | 2-$CF_3$—phenyl | oil |
| 26 | H | Me | Me | Me | 5-Me | O | 3,4-diMeO—phenyl | oil |
| 27 | H | Me | Me | Me | 5-Me | O | 2-MeO—phenyl | oil |
| 28 | H | Me | Me | Me | 5-Me | O | 3-PhO—phenyl | oil |
| 29 | H | Me | Me | Me | 5-Me | O | 3-CN—phenyl | oil |
| 30 | H | Me | Me | Me | 5-Me | O | benzoxazol-2-yl | 107–9 |
| 31 | H | Me | Me | Me | 5-Me | O | 2,6-xylyl | oil |
| 32 | H | Me | Me | Me | 5-Me | O | 3,4-diCl—phenyl | oil |
| 33 | H | Me | Me | Me | 5-Me | O | 3-EtOC(=O)—phenyl | oil |
| 34 | H | Me | Me | Me | 5-Me | O | 4-tolyl | oil |
| 35 | H | —$(CH_2)_2O(CH_2)_2$— | | Me | 5-Me | O | 3-$CF_3$—phenyl | oil |
| 36 | H | H | Me | Me | 5-Me | O | 3-$CF_3$—phenyl | 122–3 |
| 37 | H | Et | Et | Me | 5-Me | O | 3-$CF_3$—phenyl | oil |
| 38 | H | Pr | Pr | Me | 5-Me | O | 3-$CF_3$—phenyl | oil |
| 39 | H | Bu | Bu | Me | 5-Me | O | 3-$CF_3$—phenyl | oil |
| 40 | H | $Pr^i$ | $Pr^i$ | Me | 5-Me | O | 3-$CF_3$—phenyl | oil |
| 41 | H | —$(CH_2)_4$— | | Me | 5-Me | O | 3-$CF_3$—phenyl | 71–3 |
| 42 | H | Ph | Me | Me | 5-Me | O | 3-$CF_3$—phenyl | oil |
| 43 | H | —$(CH_2)_5$— | | Me | 5-Me | O | 3-$CF_3$—phenyl | oil |
| 44 | H | H | CN | Me | 5-Me | O | 3-$CF_3$—phenyl | 138–40 |
| 45 | H | Et | Me | Me | 5-Me | O | 3-$CF_3$—phenyl | oil |
| 46 | H | Pr | H | Me | 5-Me | O | 3-$CF_3$—phenyl | 44–6 |
| 47 | H | benzyl | H | Me | 5-Me | O | 3-$CF_3$—phenyl | 121–3 |
| 48 | H | Me | Me | Me | 5-Me | O | 3-Ph-1,2,4-thiadiazol-5-yl | 100–5 |

TABLE 1-continued

| Cmp | R¹ | R² | R³ | R⁴ | (R⁵)ₘ | A | R⁶ | m.p./° C. |
|---|---|---|---|---|---|---|---|---|
| 49 | H | Me | Me | Me | 5-Me | —OCH(Me)— | 3-CF₃—phenyl | 97–9 |
| 50 | H | Me | Me | Me | 5-Me | O | 4-CF₃—phenyl | oil |
| 51 | H | Me | Me | Me | 5-Me | O | 2-CF₃—phenyl | oil |
| 52 | H | Me | Me | Me | 5-Me | O | 3-Cl-5-CF₃-2-pyridyl | oil |
| 53 | H | Me | Me | Me | 5-Me | direct bond | 3-CF₃—phenyl | oil |
| 54 | H | Me | Me | Me | 5-Me | O | 4,6-diMe—pyrimidin-2-yl | 95–9 |
| 55 | H | Me | Me | Me | 5-Me | O | 3,5-diCl—phenyl | 67–9 |
| 56 | H | Me | Me | Me | 5-Me | O | 3-MeO—phenyl | oil |
| 57 | H | cyHex | H | Me | 5-Me | O | 3-CF₃—phenyl | 93–4 |
| 58 | H | Prⁱ | H | Me | 5-Me | O | 3-CF₃—phenyl | 62.5–4.5 |
| 59 | H | Et | H | Me | 5-Me | O | 3-CF₃—phenyl | 100–2 |
| 60 | H | Me | Me | Me | 5-Me | —NH—C(=O)— | 3,5-diMe-4-oxazolyl | 215–8 |
| 61 | H | Me | Me | Me | 5-Me | O | 4-Buᵗ—phenyl | 95–6 |
| 62 | H | HO | H | Me | 5-Me | O | 3-CF₃—phenyl | 130–1 |
| 63 | H | MeO | H | Me | 5-Me | O | 3-CF₃—phenyl | 59–61 |
| 64 | H | EtO | H | Me | 5-Me | O | 3-CF₃—phenyl | 68–9 |
| 65 | H | Me | Me | Me | 5-Me | O | phenyl | oil |
| 66 | H | Me | Me | Me | 5-Me | O | 3-Cl-1,2,4-thiadiazol-5-yl | 120–2 |
| 67 | H | Me | Me | Prⁱ | 5-Me | O | 3-CF₃—phenyl | oil |
| 68 | H | Me | Me | Me | 5-Cl | O | 3-Ph-1,2,4-thiadiazol-5-yl | 99–101 |
| 69 | H | Me | Me | Me | 5-Me | SO₂ | 3-CF₃—phenyl | 122–3 |
| 70 | H | Me | Me | Me | 5-Me | —N(Me)—Cl(=O)— | 3,5-diMe—isoxazol-4-yl | oil |
| 71 | H | Me | Me | Me | 3-Me | O | 3-CF₃—phenyl | oil |
| 72 | H | Me | Me | Me | 5-Me | O | 3-Br-1,2,4-thiadiazol-5-yl | 129–31 |
| 73 | H | Me | Me | Me | 5-Me | —NHC(=O)— | phenyl | 180–1 |
| 74 | H | Me | Me | Me | 5-Me | —N(Me)C(=O)— | phenyl | oil |
| 75 | H | Me | Me | Me | 5-Me | direct bond | piperidinyl | 93–4 |
| 76 | H | Me | Me | Me | 5-Me | O | 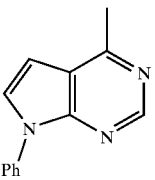 | 124–6 |
| 77 | H | Me | Me | Me | 5-Me | O | 7-Cl-4-quinazolinyl | 160–2 |
| 78 | H | Me | Me | Me | 5-Me | O | 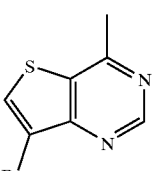 | 170–2 |
| 79 | H | Me | Me | Me | 5-Me | direct bond | 2,5-diMe-1-pyrrolyl | 90–1 |
| 80 | H | Me | Me | Me | 5-Me | direct bond | phthalimido | 170–3 |
| 81 | H | Me | Me | Me | 5-Me | O | 5-CF₃-1,3,4-thiadiazol-2-yl | oil |
| 82 | H | Me | Me | Me | 5-Me | O | 5-Buᵗ-1,3,4-thiadiazol-2-yl | 104–6 |
| 83 | H | Me | Me | Me | 5-Me | O | 5-Ph-1,3,4-thiadiazol-2-yl | oil |
| 84 | H | Me | Me | Me | 5-Me | O | 6-Cl—benzthiazol-2-yl | 109–11 |
| 85 | H | Me | Me | Me | 5-Me | O | 5-NO₂-2-thiazolyl | oil |
| 85 | H | Me | Me | Me | 5-Me | O | 5-Ph-2-thiazolyl | 111–14 |
| 87 | H | Me | Me | Me | 5-Me | direct bond | morpholino | 93–4 |
| 88 | H | Me | Me | Me | 5-Me | O | 8-F-4-quinazolinyl | 98–100 |
| 89 | H | Me | Me | Me | 5-Me | O | 3,6-diNO₂-4-coumarinyl | 178–81 |
| 90 | H | Me | Me | Me | 5-Me | O | 2-F—phenyl | oil |
| 91 | H | Me | Me | Me | 5-Me | O | 4,6-diMeO-1,3,5-triazin-2-yl | 82–4 |
| 92 | H | Me | Me | Me | 5-Me | direct bond | 3-Et₂NC(=O)-1-piperidinyl | oil |
| 93 | H | Me | Me | Me | 5-Me | S | 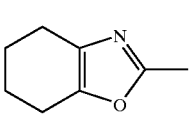 | oil |

TABLE 1-continued

| Cmp | R¹ | R² | R³ | R⁴ | (R⁵)ₘ | A | R⁶ | m.p./° C. |
|---|---|---|---|---|---|---|---|---|
| 94 | H | Me | Me | Me | 5-Me | S | 4-(4-Cl—phenyl)-2-oxazolyl | oil |
| 95 | H | Me | Me | Me | 5-Me | O | 4-(4-Cl—phenyl)-2-oxazolyl | oil |
| 96 | H | Me | Me | Me | 5-Me | O | 2-CF₃-4-quinazolinyl | 119–21 |
| 97 | H | Me | Me | Me | 5-Me | direct bond | 4,5-diCl—phthalimido | 196–8 |
| 98 | H | Me | Me | Me | 5-Me | —NHC(=O)— | 4-F—phenyl | 166–8 |
| 99 | H | CN | H | Me | 5-Me | O | 3-Buᵗ—phenyl | oil |
| 100 | H | Et | Me | Me | 5-Me | O | 3-Buᵗ—phenyl | oil |
| 101 | H | Me | Me | Me | 5-Me | O | 4-CF₃—pyrimidin-2-yl | 123–5 |
| 102 | H | Me | Me | Me | 5-Me | direct bond | 2,6-diMe—morpholin-4-yl | 102–3 |
| 103 | H | Me | Me | Me | 5-Me | O | 2-CF₃-4-quinolinyl | 126–8 |
| 104 | H | Me | Me | Me | 5-Me | O | 2-tolyl | oil |
| 105 | H | Me | Me | Me | 5-Me | O | 2-Prⁱ—phenyl | oil |
| 106 | H | Et | H | Me | 5-Me | O | 3-Buᵗ—phenyl | 74–6 |
| 107 | Et | Me | Me | H | 5-Me | O | 3-Buᵗ—phenyl | 89–91 |
| 108 | Me | Me | Me | H | 5-Me | O | 3-Buᵗ—phenyl | oil |
| 109 | H | Me | Me | H | 5-Me | O | 3-Buᵗ—phenyl | oil |
| 110 | Et | Me | Me | Me | 5-Me | O | 3-Buᵗ—phenyl | 113–6 |
| 111 | H | Me | Me | Me | 5-Me | direct bond | 4-Me-1-piperazinyl | 67–8 |
| 112 | H | Me | Me | Me | 5-Me | O | 4-(2-thiazolyl)-2-thiazolyl | 110–12 |
| 113 | H | Me | Me | Me | 5-Me | O | 4-Buᵗ-2-thiazolyl | oil |
| 114 | H | Me | Me | Me | 5-Me | O | 3-(4-Cl—phenyl)-1,2,4-oxadiazol-5-yl | 106–8 |
| 115 | H | Me | Me | Me | 5-Me | direct bond | 2-Me-5-(3-CF—phenyl)-1-pyrrolyl | oil |
| 116 | H | Me | Me | Me | 5-Me | O | 3-MeO-1,2,4-thiadiazol-5-yl | 99–101 |
| 117 | H | Me | Me | Me | 5-Me | O | 3-Me-1,2,4-thiadiazol-5-yl | 92–4 |
| 118 | H | Me | Me | Me | 5-Me | O | 6-Ph-3-pyridazinyl | 86–9 |
| 119 | H | Me | Me | Me | 5-Me | O | 3-MeS-1,2,4-thiadiazol-6-yl | oil |
| 120 | H | Me | Me | Me | 5-Me | O | 4-(3-CF₃—phenyl)-2-thiazolyl | 93–5 |
| 121 | H | Me | Me | Me | 5-Me | S | 4-Me-1,2,4-triazol-3-yl | oil |
| 122 | H | Me | Me | Me | 5-Me | O | 3-CN-2-pyrazinyl | 128–30 |
| 123 | H | Me | Me | Me | 5-Me | O | 3-Buᵗ-1,2,4-thiadiazol-5-yl | oil |
| 124 | H | Me | Me | Me | 5-Me | O | 2-secButyl—phenyl | oil |
| 125 | H | Me | Me | Me | 5-Me | O | 2-biphenylyl | oil |
| 126 | H | Me | Me | Me | 5-Me | O | 5-isopropenyl-1,3,4-thiadiazol-2-yl | oil |
| 127 | H | Me | Me | Me | 5-Me | O | 5-Ph-1,3,4-oxadiazol-2-yl | 120–2 |
| 128 | H | Me | Me | Me | 5-Me | direct bond | 1,2,3,4-tetrahydro-2-isoquinolinyl | oil |
| 129 | H | Me | Me | Me | 5-Me | O | 3-NEt₂—phenyl | oil |
| 130 | H | Me | Me | Me | 5-Me | O | 4-secButyl—phenyl | oil |
| 131 | H | Me | Me | Me | 5-Me | O | 5-Cl-6-Et—pyrimidin-4-yl | 100–1 |
| 132 | H | Me | Me | Me | 5-Me | O | 2-CF₃—pyrimidin-4-yl | 62–3 |
| 133 | H | Me | Me | Me | 5-Me | O | 1-Me-5-Cl-6-oxo-pyridazin-4-yl | 142–5 |
| 134 | H | Me | Me | Me | 5-Me | O | 3-Ph-5-isoxazolyl | oil |
| 135 | H | Me | Me | Me | 5-Me | O | 3-Br—phenyl | oil |
| 136 | H | Me | Me | Me | 5-Me | O | 3-(dimethyl-amino-methylene-amino)phenyl | oil |
| 137 | H | Me | Me | Me | 5-Me | O | 4-Cl-1,2,5-thiadiazol-3-yl | oil |
| 138 | H | Me | Me | Me | 5-Me | O | 3-CF₃-1,2,4-thiadiazol-5-yl | oil |
| 139 | H | Me | Me | Me | 5-Me | O | 2-Cl—phenyl | oil |
| 140 | H | Me | Me | Me | 5-Me | O | 2-MeS-5-EtOC(=O)-pyrimidin-4-yl | oil |
| 141 | H | Me | Me | Me | 5-Me | O | 1-naphthyl | oil |
| 142 | H | Me | Me | Me | 5-Me | O | 2-naphthyl | oil |
| 143 | Me | Me | Me | Me | 5-Me | O | 1-naphthyl | oil |
| 144 | Me | Me | Me | Me | 5-Me | O | 2-naphthyl | 110–12 |
| 145 | H | Me | Me | Me | 5-Me | O | 1-Ph—tetrazol-5-yl | 123–6 |
| 146 | H | Me | Me | Me | 5-Me | O | 1,1-dioxo-benzothiazol-3-yl | 177–8 |
| 147 | H | Me | Me | Me | 5-Me | direct bond | 2-benzo[b]-furanyl | 90–1 |
| 148 | H | Me | Me | Me | 5-Me | O | 6-Ph—pyrimidin-4-yl | oil |

TABLE 1-continued

| Cmp | R¹ | R² | R³ | R⁴ | (R⁵)ₘ | A | R⁶ | m.p./° C. |
|---|---|---|---|---|---|---|---|---|
| 149 | H | Me | Me | Me | 5-Me | O | 4-Prⁱ—phenyl | oil |
| 150 | H | Me | Me | Me | 5-Me | O | 3-acetylphenyl | oil |
| 151 | H | Me | Me | Me | 5-Me | O | 4-(1,1,3,3-tetramethyl-butyl)phenyl | |
| 152 | H | Me | Me | Me | 5-Me | O | 3-Prⁱ—phenyl | oil |
| 153 | H | Me | Me | Me | 5-Me | —OC(=O)— | 3,4-diCl—phenyl | oil |
| 154 | H | Me | Me | Me | 5-Me | —OC(=O)— | 4-hexylphenyl | oil |
| 155 | H | Me | Me | Me | 5-Me | —OC(=O)— | 2,6-xylyl | oil |
| 156 | H | Me | Me | Me | 5-Me | —OC(=O)CH₂— | 4-Cl—phenyl | oil |
| 157 | H | Me | Me | Me | 5-Me | —OC(=O)CH₂— | phenyl | oil |
| 158 | H | Me | Me | Me | 5-Me | —OC(=O)CH₂— | 3-MeO—phenyl | oil |
| 159 | H | Me | Me | Me | 5-Me | —OC(=O)— | 2,6-diCl—phenyl | oil |
| 160 | H | Me | Me | Me | 5-Me | —OC(=O)— | 3-Cl-2-benzo[b]-thiophenyl | oil |
| 161 | H | Me | Me | Me | 5-Me | —OC(=O)— | cyclohexyl | oil |
| 162 | H | Me | Me | Me | 5-Me | —OC(=O)— | 2,4-diCl—phenyl | oil |
| 163 | H | Me | Me | Me | 5-Me | —OC(=O)— | 2-CF₃—phenyl | oil |
| 164 | H | Me | Me | Me | 5-Me | —OC(=O)— | 2,3-diCl—phenyl | oil |
| 165 | H | Me | Me | Me | 5-Me | —OC(=O)— | 3,5-diMe—isoxazol-4-yl | oil |
| 166 | H | Me | Me | Me | 5-Me | —OC(=O)— | 4-Me-1,2,3-thiadiazol-5-yl | oil |
| 167 | H | Me | Me | Me | 5-Me | —OC(=O)— | 2-F-3-CF₃—phenyl | oil |
| 168 | H | Me | Me | Me | 5-Me | —OC(=O)— | 3-Cl-2-MeO-5-pyridyl | oil |
| 169 | H | Me | Me | Me | 5-Me | —OC(=O)— | 2-Cl-3-pyridyl | oil |
| 170 | H | Me | Me | Me | 5-Me | O | 4-(tert-pentyl)phenyl | oil |
| 171 | H | Me | Me | Me | 5-Me | O | 3-Et—phenyl | oil |
| 172 | Me | Me | Me | Me | 5-Me | O | 4-(tert-pentyl)phenyl | oil |
| 173 | H | Me | Me | Me | 5-Me | O | 4-Cl-3-Me—phenyl | oil |
| 174 | H | Me | Me | Me | 5-Me | O | 3,4-xylyl | oil |
| 175 | H | Me | Me | Me | 5-Me | O | 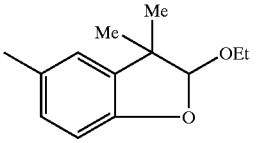 | 94–6 |
| 176 | H | Me | Me | Me | 5-Me | direct bond | 2-thienyl | oil |
| 177 | H | Me | Me | Me | 5-Me | direct bond | 5-Cl-2-thienyl | oil |
| 178 | H | Me | Me | Me | 5-Me | direct bond | 3-Cl-2-benzo[b]furanyl | 114–5 |
| 179 | H | Me | Me | Me | H | direct bond | 5-(4-Cl—phenyl)-1,2,4-oxadiezol-3-yl | 136–7 |
| 180 | H | Me | Me | Me | 5-Me | O | 4-nonylphenyl | oil |
| 181 | H | Me | Me | Me | 5-Me | O | 4-Et—phenyl | oil |
| 182 | H | Me | Me | Me | 5-Me | O | 4-biphenylyl | oil |
| 183 | H | Me | Me | Me | 5-Me | O | 4-Cl—phenyl | oil |
| 184 | H | Me | Me | Me | 5-Me | O | 4-MeS—phenyl | oil |
| 185 | H | Me | Me | Me | 5-Me | O | 4-Br—phenyl | oil |
| 186 | H | Me | Me | Me | 5-Me | —OCH₂— | 2-(4-Cl—phenyl)-4-thiazolyl | 86–9 |
| 187 | H | Me | Me | Me | 5-Me | direct bond | 2-benzo[b]thiophenyl | 67–8 |
| 188 | H | Me | Me | Me | 5-Me | O | 2-(5,6,7,8-tetrahydro)naphthyl | 84–6 |
| 189 | H | Me | Me | Me | 5-Me | O | 4-(α,α-diMe—benzyl)phenyl | oil |
| 190 | H | Me | Me | Me | 5-Me | O | 3-CF₃O—phenyl | oil |
| 191 | Me | Me | Me | Me | 5-Me | direct bond | 3-Et₂NC(=O)-1-piperidinyl | oil |
| 192 | H | Me | Me | Me | 5-Me | S | phenyl | 72–3 |
| 193 | H | Me | Me | Me | 5-Me | O | 4-MeO—phenyl | 57–8 |
| 194 | H | Me | Me | Me | 5-Me | O | 5-CF₃-2-benzthiazolyl | 106–7 |
| 195 | H | Me | Me | Me | 5-Me | O | 4-Cl-2-benzthiazolyl | 109–11 |
| 196 | H | Me | Me | Me | 5-Me | O | 5-Cl-2-benzthiazolyl | oil |
| 197 | H | Me | Me | Me | 5-Me | O | 2-benzthiazolyl | oil |
| 198 | H | Me | Me | Me | 5-Me | O | 2-Prⁱ-5-Me—phenyl | oil |
| 199 | Me | Me | Me | Me | 5-Me | O | 2-Prⁱ-5-Me—phenyl | oil |
| 200 | H | Me | Me | Me | 5-Me | O | 4-Cl-3-Et—phenyl | oil |
| 201 | Me | Me | Me | Me | 5-Me | O | 4-Cl-3-Et—phenyl | oil |
| 202 | H | Me | Me | Me | 5-Me | O | 3-Me-4-MeS—phenyl | oil |
| 203 | H | Me | Me | Me | 5-Me | O | 4-benzoylphenyl | oil |
| 204 | H | Me | Me | Me | 5-Me | O | 4-propionylphenyl | oil |
| 205 | H | Me | Me | Me | 5-Me | O | 4-(3-Me-1,2,4-thiadiazol-5-yl)phenyl | 109.5–11 |
| 206 | Me | Me | Me | Me | 5-Me | O | 3-Ph-1,2,4-thiadiazol-5-yl | 113–4 |

TABLE 1-continued

| Cmp | R¹ | R² | R³ | R⁴ | (R⁵)ₘ | A | R⁶ | m.p./° C. |
|---|---|---|---|---|---|---|---|---|
| 207 | H | Me | Me | Me | H | O | 3-Ph-1,2,4-thiadiazol-5-yl | oil |
| 208 | H | Me | Me | Me | 5-Prⁱ | O | 3-Ph-1,2,4-thiadiazol-5-yl | oil |
| 209 | Me | Me | Me | Me | H | O | 3-Ph-1,2,4-thiadiazol-5-yl | oil |
| 210 | H | Me | Me | Me | H | direct bond | 5-Buᵗ-1,2,4-oxadiazol-3-yl | oil |
| 211 | H | Me | Me | Me | H | direct bond | 5-Buᵗ1,3,4-oxadiazol-2-yl | 79–80 |
| 212 | H | Me | Me | Me | 5-Me | O | 4-acetylphenyl | 80–1 |
| 213 | H | Me | Me | Me | 5-Me | O | 3-(3-CF₃—phenoxy)—phenyl | oil |
| 214 | H | Me | Me | Me | 5-Me | —CH(CN)— | 3-CF₃—phenyl | oil |
| 215 | H | Me | Me | Me | 5-Me | O | 4-(4-Cl—phenyl)-2-thiazolyl | oil |
| 216 | H | Me | Me | Me | 5-Me | O | 4-(4-tolyl)-2-thiazolyl | oil |
| 217 | H | Me | Me | Me | 5-Me | O | 4-(4-MeO—phenyl)-2-thiazolyl | oil |
| 218 | H | Me | Me | Me | 5-Me | O | 6-Cl—pyrimidin-4-yl | 205–7 |
| 219 | H | Me | Me | Me | 5-Me | O | 4-oxo-2-Ph-4H-1-benzopyran-6-yl | oil |
| 220 | H | Me | Me | Me | 5-Me | O | 2-(benzyloxy)phenyl | oil |
| 221 | H | Me | Me | Me | 5-Me | O | 3,4-methylenedioxy—phenyl | oil |
| 222 | H | Me | Me | Me | 5-Me | O | 3,5-xylyl | oil |
| 223 | H | Me | Me | Me | 5-Me | O | 3,5-diMeO—phenyl | oil |
| 224 | H | Me | Me | Me | 5-Me | O | 6-PhO—pyrimidin-4-yl | oil |
| 225 | H | Et | Me | Me | 5-Me | O | 3-Ph-1,2,4-thiadiazol-5-yl | oil |
| 226 | H | Me | Me | Me | 5-Me | direct bond | 3-Cl-2-benzo[b]thiophenyl | 84–6 |
| 227 | H | CN | H | Me | 5-Me | O | 3-Ph-1,2,4-thiadiazol-5-yl | oil |
| 228 | H | Me | Me | Me | H | direct bond | 5-(4-Cl—phenyl)-1,3,4-oxadiazol-2-yl | 168–9 |
| 229 | Me | Me | Me | Me | H | direct bond | 5-(4-Cl—phenyl)-1,3,4-oxadiazol-2-yl | 133–5 |
| 230 | Me | Me | Me | Me | 5-Me | O | 3-Prⁱ—phenyl | oil |
| 231 | H | Me | Me | Me | 5-Me | —CH(CO₂Me)— | 3-CF₃—phenyl | oil |
| 232 | H | Et | H | Me | 5-Me | O | 3-Ph-1,2,4-thiadiazol-5-yl | oil |
| 233 | Me | Me | Me | Me | H | direct bond | 5-Buᵗ-1,3,4-oxadiazol-2-yl | oil |
| 234 | H | Me | Me | Me | 5-Me | O | 3-(4-tolyl)-1,2,4-thiadiazol-5-yl | 121–4 |
| 235 | H | Me | Me | Me | 5-Me | O | 4-propargyloxyphenyl | oil |
| 236 | H | Me | Me | Me | 5-Me | O | 6-Br-2-pyridyl | oil |
| 237 | Me | Me | Me | H | 5-Me | O | 3-Ph-1,2,4-thiadiazol-5-yl | oil |
| 238 | Me | Me | Me | Me | 5-Me | O | 3-Br—phenyl | oil |
| 239 | Me | Me | Me | Me | 5-Me | O | 4-Et—phenyl | oil |
| 240 | Me | Me | Me | Me | 5-Me | O | 4-biphenylyl | oil |
| 241 | Me | Me | Me | Me | 5-Me | O | 4-Cl—phenyl | oil |
| 242 | Me | Me | Me | Me | 5-Me | O | 4-MeS—phenyl | oil |
| 243 | Me | Me | Me | Me | 5-Me | O | 4-Br—phenyl | oil |
| 244 | Me | Me | Me | Me | 5-Me | O | 4-benzoylphenyl | oil |
| 245 | Me | Me | Me | Me | 5-Me | O | 4-propionylphenyl | oil |
| 246 | H | —(CH₂)₅— | | Me | 5-Me | O | 3-Ph-1,2,4-thiadiazol-5-yl | oil |
| 247 | H | Me | Me | Me | H | O | 5-CF₃-1,3,4-thiadiazol-2-yl | oil |
| 248 | H | Me | Me | Me | 5-Me | O | 6-(trimethylsilylethynyl)-2-pyridyl | oil |
| 249 | H | Me | Me | Me | 5-Me | O | 6-ethynyl-2-pyridyl | oil |
| 250 | H | Me | Me | Me | 5-Me | O | 2,4-diCl—phenyl | 96–7 |
| 251 | H | Me | Me | Me | 5-Me | O | 5-Prⁱ-2-Me—phenyl | oil |
| 252 | H | Me | Me | Me | 5-Me | O | 3-(4-Cl—phenyl)-1,2,4-thiadiazol-5-yl | 118–22 |
| 253 | H | Me | Me | Me | 5-Me | O | 3-(3-NO₂—phenyl)-1,2,4-thiadiazol-5-yl | 125–8 |
| 254 | Et | Me | Me | Me | 5-Me | O | 3-Ph-1,2,4-thiadiazol-5-yl | oil |
| 255 | Et | Me | Me | H | 5-Me | O | 3-Ph-1,2,4-thiadiazol-5-yl | oil |

TABLE 1-continued

| Cmp | R¹ | R² | R³ | R⁴ | (R⁵)ₘ | A | R⁶ | m.p./° C. |
|---|---|---|---|---|---|---|---|---|
| 256 | H | Me | Me | Me | 5-Me | O | 4-Prⁱ-3-Me—phenyl | oil |
| 257 | H | Me | Me | Me | H | O | 3-Buᵗ—phenyl | oil |
| 258 | H | Me | Me | Me | 5-Me | O | 9-oxo-fluoren-2-yl | oil |
| 259 | H | Me | Me | Me | 5-Me | O | 3-(3,5-diCF₃—phenyl)-1,2,4-thiadiazol-5-yl | 112–5 |
| 260 | H | Me | Me | Cl | H | O | 3-Buᵗ—phenyl | oil |
| 261 | H | Me | Me | Me | 5-Me | O | 4-benzyloxyphenyl | oil |
| 262 | H | Me | Me | Me | 5-Me | O | 6-(4-Cl—phenyl)-2-pyridyl | oil |
| 263 | H | Me | Me | Me | 5-Me | O | 4-HO—phenyl | oil |
| 264 | H | Me | Me | Me | 5-Me | O | 3-CF₃—benzyl | 75–7 |
| 265 | H | Me | Me | Me | 5-Me | O | 6-(3-CF₃—phenylthio)-pyrimdin-4-yl | oil |
| 266 | H | Me | Me | Me | 5-Me | O | 3-benzyloxyphenyl | oil |
| 267 | H | Me | Me | Me | 5-Me | —OCH₂— | cyclohexyl | oil |
| 268 | H | Me | Me | Me | 5-Me | —OCH₂CH₂O— | 4-Cl—phenyl | oil |
| 269 | H | Me | Me | Me | 5-Me | —OCH₂CH₂O— | 4-Buᵗ—phenyl | oil |
| 270 | H | Me | Me | Me | 5-Me | —O(CH₂)₄O— | phenyl | oil |
| 271 | H | Me | Me | Me | 5-Me | —O(CH₂)₄— | phthalimido | oil |
| 272 | H | Me | Me | Me | 5-Me | —O(CH₂)₅— | phenyl | oil |
| 273 | H | Me | Me | Me | 5-Me | —O(CH₂)₃O— | 4-Buᵗ—phenyl | oil |
| 274 | H | Me | Me | Me | 5-Me | —O(CH₂)₄O— | 4-Buᵗ—phenyl oil | oil |
| 275 | H | Me | Me | Me | 5-Me | —O(CH₂)₄O— | 2-Buᵗ—phenyl | oil |
| 276 | H | Me | Me | Me | 5-Me | —OCH₂— | 2-tetrahydropyranyl | oil |
| 277 | H | Me | Me | Me | 5-Me | —O(CH₂)₃O— | phenyl | oil |
| 278 | H | Me | Me | Me | 5-Me | —O(CH₂)₉O— | 2-tetrahydropyranyl | oil |
| 279 | H | Me | Me | Me | 5-Me | —OCH₂— | 2-(1-methoxy-carbonyl-2-methoxyvinyl)phenyl | oil |
| 280 | H | Me | Me | Me | 5-Me | —OCH₂CH₂— | 2-phenylethyl | oil |
| 281 | H | Pr | Me | Me | 5-Me | O | 3-Buᵗ—phenyl | oil |
| 282 | H | Bu | Me | Me | 5-Me | O | 3-Buᵗ—phenyl | oil |
| 283 | H | Prⁱ | Me | Me | 5-Me | O | 3-Buᵗ—phenyl | oil |
| 284 | H | allyl | Me | Me | 5-Me | O | 3-Buᵗ—phenyl | oil |
| 285 | H | Bu | Et | Me | 5-Me | O | 3-Buᵗ—phenyl | oil |
| 286 | H | Et | Et | Me | 5-Me | O | 3-Buᵗ—phenyl | oil |
| 287 | H | Me | Me | Me | 5-Me | O | 6-BuᵗS—pyrimidin-4-yl | oil |
| 288 | H | Me | Me | Me | 5-Me | O | 3,3-diMe-2-EtO-2,3-dihydrobenzfuran-5-yl | oil |
| 289 | H | Me | Me | Me | 5-Me | O | 6-cyHexS—pyrimidin-4-yl | oil |
| 290 | H | Me | Me | Me | 5-Me | —OCH₂— | 4-cyHexylmethyloxy—phenyl | oil |
| 291 | H | Me | Me | Me | 5-Me | O | 3-PrⁱO—phenyl | oil |
| 292 | H | Me | Me | Me | H | O | 2-(2-phenoxy—ethoxy)phenyl | oil |
| 293 | H | CN | H | H | 5-Me | O | 3-Ph-1,2,4-thiadiazol-5-yl | 152–4 |
| 294 | H | Me | Me | Cl | H | O | 3-CF₃—phenyl | oil |
| 295 | H | Me | Me | Me | 5-Me | O | 6-(2-phenylethyl-thio)pyrimidin-4-yl | oil |
| 296 | H | Me | Me | Me | 5-Me | O | 4-(3-CF₃—benzyloxy)phenyl | oil |
| 297 | H | Me | Me | CF₃ | H | O | 3-Buᵗ—phenyl | oil |
| 298 | H | Me | Me | Me | 5-Me | O | 4-(2-Cl—phenyl)thiazol-2-yl | oil |
| 299 | H | Me | Me | Me | 5-Me | O | 4-(3-Cl—phenyl)thiazol-2-yl | 122–5 |
| 300 | H | Me | Me | Me | 5-Me | O | 4-(4-CF₃—phenyl)hiazol-2-yl | 123–5 |
| 301 | H | Me | Me | Me | 5-Me | O | 3-(3-CF₃—benzyloxy)phenyl | oil |
| 302 | H | Me | Me | Me | 5-Me | O | 2-(4-Me—butoxy)phenyl | oil |
| 303 | H | Me | Me | Me | 5-Me | O | 4-PrⁱO—phenyl | oil |
| 304 | H | Me | Me | Me | 5-Me-6-NO₂ | O | 3-Buᵗ—phenyl | oil |
| 305 | H | Me | Me | Me | 5-Me | O | 2-(3-CF₃—benzyloxy)phenyl | oil |
| 306 | H | Me | Me | Me | H | O | 2-(3-CF₃—benzyloxy)phenyl | oil |
| 307 | H | CN | H | Me | 5-Me | O | 3-Cl—phenyl | 134–5 |
| 308 | H | CN | H | Me | 5-Me | O | 4-Prⁱ—phenyl | 159–60 |
| 309 | H | CN | H | Me | 5-Me | O | 3-MeO—phenyl | 104–8 |
| 310 | H | Et | Me | Me | 5-Me | O | 3-Cl—phenyl | oil |
| 311 | H | Et | Me | Me | 5-Me | O | 4-Prⁱ—phenyl | oil |
| 312 | H | Et | Me | Me | 5-Me | O | 3-MeO—phenyl | oil |

TABLE 1-continued

| Cmp | R$^1$ | R$^2$ | R$^3$ | R$^4$ | (R$^5$)$_m$ | A | R$^6$ | m.p./° C. |
|---|---|---|---|---|---|---|---|---|
| 313 | H | Et | Me | Me | 5-Me | O | 4-(tert-pentyl)phenyl | oil |
| 314 | H | Me | Me | Me | 5-Me | O | 3-(1-Me—undecyloxy)phenyl | oil |
| 315 | H | Me | Me | Me | 5-Me | O | 2-Pr$^i$O—phenyl oil | oil |
| 316 | H | Me | Me | Me | 5-Me | O | 3,5-diPr$^i$—phenyl | oil |
| 317 | H | Me | Me | Me | 5-Me | O | 3-MeO-5-Me—phenyl | oil |
| 318 | H | Me | Me | Me | 5-Me | O | 3,5-diCF$_3$—phenyl | oil |
| 319 | H | Me | Me | Me | 5-Me | O | 2-(1-Me—undecycloxy)phenyl | oil |
| 320 | H | Me | Me | Me | H | O | 2-(isopentoxy)phenyl | oil |
| 321 | H | Me | Me | Me | H | O | 2-Pr$^i$O—phenyl | oil |
| 322 | H | Me | Me | Me | 5-Me | O | 6-Cl—benzoxazol-2-yl | 118–20 |
| 323 | H | CN | H | Me | 5-Me | O | 3-PhO—phenyl | oil |
| 324 | H | CN | H | Me | 5-Me | O | 4-Bu$^t$—phenyl | oil |
| 325 | H | Et | Me | Me | 5-Me | O | 3-PhO—phenyl | oil |
| 326 | H | Et | Me | Me | 5-Me | O | 4-Bu$^t$—phenyl | oil |
| 327 | H | Me | Me | Me | 5-Me | O | 5-Cl—benzoxazol-2-yl | 190 |
| 328 | H | Me | Me | Me | 5-Me | O | 5-NO$_2$—benzoxazol-2-yl | oil |
| 329 | H | allyl | Me | Me | 5-Me | O | 3-CF$_3$—phenyl | oil |
| 330 | H | Pr | Me | Me | 5-Me | O | 3-CF$_3$—phenyl | oil |
| 331 | H | Bu | Me | Me | 5-Me | O | 3-CF$_3$—phenyl | oil |
| 332 | H | Me | Me | Me | 5-Me | O | 3-HO—phenyl | 155–7 |
| 333 | H | CN | H | Me | 5-Me | O | 3,5-diCl—phenyl | 199–201 |
| 334 | H | Me | Me | Me | 5-Me | O | 3-(3-Ph-1,2,4-thiadazol-5-yloxy)phenyl | oil |
| 335 | H | Et | Me | Me | 5-Me | O | 3,5-diCl—phenyl | oil |
| 336 | H | Me | Me | Me | 5-Me | O | 5-Br—benzthiazol-2-yl | oil |
| 337 | H | Me | Me | Me | 5-Me | O | 5-(4-CF$_3$—phenyl)benzthiazol-2-yl | 131–3 |
| 338 | H | Me | Me | Me | 5-Me | O | 5-Ph—benzthiazol-2-yl | 107–9 |
| 339 | H | Me | Me | Me | 5-Me | O | 5-(4-CF$_3$O—phenyl)-benzthiazol-2-yl | 138–40 |
| 340 | H | Me | Me | Me | 5-Me | O | 3-(isopentoxy)phenyl | oil |
| 341 | H | Me | Me | Me | 5-Me | O | 3-(cyclohexylmethoxy)phenyl | oil |
| 342 | H | Me | Me | Me | 5-Me | O | 3-(4-biphenylylmethoxy)-phenyl | oil |
| 343 | H | Me | Me | Me | 5-Me | O | 3-(propargyloxy)phenyl | oil |
| 344 | H | Me | Me | Me | 5-Me | O | 3-(allyloxy)phenyl | oil |
| 345 | H | Me | Me | Me | 5-Me | O | 3-(PhO—ethoxy)phenyl | oil |
| 346 | H | Me | Me | Me | 5-Me | O | 3-(2-thienyl)phenyl | oil |
| 347 | H | Me | Me | Me | 5-Me, 6-Br | O | 3-Bu$^t$—phenyl | oil |
| 348 | H | Me | Me | Me | 5-Me | O | 3-(cyclopropyl-methoxy)phenyl | oil |
| 349 | H | Me | Me | Me | 5-Me | O | 3-(phenacyloxy)-phenyl | oil |
| 350 | H | Me | Me | Me | 5-Me | O | 3-(methoxycarbonyl-methyl)phenyl | oil |
| 351 | H | Me | Me | Me | 5-Me | O | 4-(3,4-diCl—phenyl)thiazol-2-yl | 121–3 |
| 352 | H | Me | Me | Me | 5-Me | O | 3-(benzyloxycarbonyl-methoxy)phenyl | oil |
| 353 | H | Me | Me | Me | 5-Me | O | 3-(3-Cl-4-F—phenyl)phenyl | oil |
| 354 | H | Me | Me | Me | 5-Me | O | 3-(tetrahydrofuran-2-ylmethoxy)phenyl | oil |
| 355 | H | Me | Me | Me | 5-Me | O | 3-(tetrahydropyran-2-ylmethoxy)phenyl | oil |
| 356 | H | Me | Me | Me | 5-F | O | 3-Ph-1,2,4-thiadiazol-5-yl | 67–9 |
| 357 | H | Me | Me | Me | 5-Me | O | 4-(4-Cl—benzoyl)phenyl | oil |
| 358 | H | Me | Me | Me | 5-Me | O | 3-[1-(ethoxycarbonyl)-ethoxy]phenyl | oil |
| 359 | H | Me | Me | Me | 5-Me | O | 3-(2,2,2-trifluoroethoxy)phenyl | oil |
| 360 | H | Me | Me | Me | 5-Me | O | 3-(4-CN—butoxy)phenyl | oil |
| 361 | H | Me | Me | Me | 5-Me | O | 4-Cl-3-CF$_3$—phenyl | oil |
| 362 | H | Me | Me | Me | 5-Me | O | 5-CF$_3$—benzthiazol-2-yl | oil |

TABLE 1-continued

| Cmp | R¹ | R² | R³ | R⁴ | (R⁵)ₘ | A | R⁶ | m.p./° C. |
|---|---|---|---|---|---|---|---|---|
| 363 | H | Me | Me | Me | 5-F | O | 3-CF₃—phenyl | oil |
| 364 | H | Et | Me | Me | 5-Me | O | 4-Cl-3-CF₃—phenyl | oil |
| 365 | H | Me | Me | Me | 5-Me | O | 4-F-3-CF₃—phenyl | oil |
| 366 | H | Me | Me | Me | 5-Me | O | 3-iodo-phenyl | oil |
| 367 | H | Me | Me | Me | 5-Me | O | 3-acetoxyphenyl | oil |
| 368 | H | Me | Me | Me | 5-Me | O | 5-CF₃—benzthiazol-2-yl | oil |
| 369 | H | Me | Me | Me | 5-Me | O | 3-(4,6-diMe—pyrimidin-2-yloxy)phenyl | oil |
| 370 | H | Me | Me | Me | 5-Me | O | 3-Buᵗ—phenyl | oil |
| 371 | H | Me | Me | Me | 5-Me | O | 3-(1-benzoyl-1-methylethoxy)phenyl | oil |
| 372 | H | Me | Me | Me | 5-Me | O | 3-(1-ethoxycarbonyl-2-methylprop-1-yloxy)phenyl | oil |
| 373 | H | CN | Me | Me | 5-Me | O | 4-Cl-3-CF₃—phenyl | oil |
| 374 | H | Et | CN | Me | 5-Me | O | 4-Cl-3-CF₃—phenyl | oil |
| 375 | H | Ac | CN | Me | 5-Me | O | 4-Cl-3-CF₃—phenyl | oil |
| 376 | H | Me | Me | Me | 5-Me | O | 3-(1-acetylethoxy)-phenyl | oil |
| 377 | H | Me | Me | Me | 5-Me | O | 3-(1-ethylpropoxy)-phenyl | oil |
| 378 | H | Me | Me | Me | 5-Me | O | 3-cyclopentylphenyl | oil |
| 379 | H | Me | Me | Me | 5-Me | O | 3-(3,5-diCl-2-pyridyloxy)phenyl | oil |
| 380 | H | Me | Me | Me | 5-Me | O | 3-[ethoxycarbonyl-(N-methoxyimino)-methoxy]phenyl | oil |
| 381 | H | Me | Me | Me | 5-Me | O | 4-(2-CF₃—benzoyl)phenyl | oil |
| 382 | H | Me | Me | Me | 5-Me | O | 3-hexylphenyl | oil |
| 383 | H | Me | Me | Me | 5-Me | O | 5-Ph—thiazol-2-yl | oil |
| 384 | H | Me | Me | Me | 5-Me | O | 3-(2,2-dimethoxy-ethoxy)phenyl | oil |
| 385 | H | Me | Me | Me | 5-Me | O | 3-(2,2-diethoxyethoxy)-phenyl | oil |
| 386 | H | Me | Me | Me | 5-Me | O | 3-[2-(3-Buᵗ—phenoxy)-ethoxy]phenyl | oil |
| 387 | H | Me | Me | Me | 5-Me | O | 3-[2-(4-F—phenoxy)-ethoxy]phenyl | 102–4 |
| 388 | H | Me | Me | Me | 5-Me | O | 3-CF₃SO₂O—phenyl | oil |
| 389 | H | Me | Me | Me | 5-Me | O | 4-Br-3-Cl—phenyl | 86–8 |
| 390 | H | Me | Me | Me | 5-Me | O | 3-(2-Me-2-phenpropyl)-phenyl | oil |
| 391 | H | Me | Me | Me | 5-Me | O | 3-(1-HO-1-Me—ethyl)-phenyl | oil |
| 392 | H | Me | Me | Me | 5-Me | O | 3-(1-MeO-1-Me—ethyl)-phenyl | oil |
| 393 | H | Et | Me | Me | 5-Me | O | 4-F-3-CF₃—phenyl | oil |
| 394 | H | Me | Me | Me | 5-Me | O | 4-Me-3-CF₃—phenyl | oil |
| 395 | H | Et | Me | Me | 5-Me | O | 4-Me-3-CF₃—phenyl | oil |
| 396 | H | —(CH₂)₅— | | Me | 5-Me | O | 3-Buᵗ—phenyl | oil |
| 397 | H | H | CN | Me | Me | O | 3-CF₃-4-Cl—phenyl- | 111–4 |
| 398 | H | Me | Me | Me | Me | C=O | 3-CF₃—phenyl | oil |

Those compounds in Table 1 which do not have discrete melting points have the characteristic ¹H N.M.R. shown in Table 2 below.

TABLE 2

| Cmp | Data |
|---|---|
| 2 | 1.78 (s, 3H, N=CCH₃), 2.00 (s, 3H, ArCH₃), 2.18 (s, 3H, ArCH₃), 3.05 (s, 6H, N(CH₃)₂) |
| 3 | 2.15 (s, 3H, ArCH₃), 2.20 (s, 3H, ArCH₃), 3.00 (s, 6H, N(CH₃)₂), 3.95 (s, 2H, SCH₂) |
| 4 | 2.00 (s, 3H, ArCH₃), 2.20 (s, 3H, ArCH₃), 3.00 (s, 6H, N(CH₃)₂) |
| 5 | 1.70 (s, 3H, N=CCH₃), 1.90 (s, 3H, ArCH₃), 2.10 (s, 3H, ArCH₃), 3.00 (s, 6H, N(CH₃)₂), 3.90 (s, 2H, SCH₂) |
| 6 | 1.80 (s, 3H, N=CCH₃), 2.00 (s 3H, ArCH₃), 2.20 (s, 6H, N(CH₃)₂), 3.00 (s, 6H, N(CH₃)₂) |
| 7 | 2.10 (s, 3H, ArCH₃), 2.20 (s, 3H, ArCH₃), 3.00 (s, 6H, N(CH₃)₂) |
| 9 | 2.10 (s, 3H, ArCH₃), 2.20 (s, 3H, ArCH₃), 2.30 (s, 3H, ArCH₃), 3.00 (s, 6H, N(CH₃)₂) |
| 10 | 1.75 (s, 3H, N=CCH₃), 2.00 (s, 3H, ArCH₃), 2.20 (s, 3H, ArCH₃), 3.00 (s, 6H, N(CH₃)₂), 5.10 (s, 2H, ArCH₂ |
| 12 | 2.17 (s, 3H, ArCH₃), 2.22 (s, 3H, ArCH₃), 3.05 (s, 6H, N(CH₃)₂) |
| 13 | 2.25 (s, 3H, ArCH₃), 3.00 (s, 6H, N(CH₃)₂) |
| 14 | 3.00 (s, 6H, N(CH₃)₂) |
| 17 | 2.18 (s, 3H, ArCH₃), 2.22 (s, 3H, ArCH₃), 2.99 (s, 6H, N(CH₃)₂), 5.00 (s, 2H, ArCH₂) |

TABLE 2-continued

| Cmp | Data |
|---|---|
| 18 | 2.20 (s, 3H, ArCH$_3$), 3.00 (bs, 6H, N(CH$_3$)$_2$) |
| 19 | 2.10 (s, 3H, ArCH$_3$), 3.00 (s, 6H, N(CH$_3$)$_2$), |
| 20 | 2.15 (s, 6H, ArCH$_3$), 3.00 (s, 6H, N(CH$_3$)$_2$) |
| 21 | 1.15 (d, 6H, CH(CH$_3$)$_2$), 2.20 (s, 3H, ArCH$_3$), 3.00 (m, 7H, CH and N(CH$_3$)$_2$) |
| 22 | 2.15 (s, 3H, ArCH$_3$), 2.22 (s, 3H, ArCH$_3$), 3.04 (s, 6H, N(CH$_3$)$_2$) |
| 23 | 2.10 (s, 3H, ArCH$_3$), 2.22 (s, 3H, ArCH$_3$), 3.02 (s, 6H, N(CH$_3$)$_2$) |
| 24 | 2.10 (s, 3H, ArCH$_3$), 2.20 (s, 3H, ArCH$_3$), 3.00 (s, 6H, N(CH$_3$)$_2$) |
| 25 | 2.10 (s, 3H, ArCH$_3$), 2.20 (s, 3H, ArCH$_3$), 3.00 (s, 6H, N(CH$_3$)$_2$) |
| 26 | 2.14 (s, 3H, ArCH$_3$), 2.19 (s, 3H, ArCH$_3$), 3.00 (s, 6H, N(CH$_3$)$_2$, 3.82 (s, 3H, OCH$_3$), 3.96 (s, 3H, OCH$_3$) |
| 27 | 2.14 (s, 3H, ArCH$_3$), 2.18 (s, 3H, ArCH$_3$), 3.00 (s, 6H, N(CH$_3$)$_2$), 3.93 (s, 3H, OCH$_3$) |
| 28 | 2.13 (s, 3H, ArCH$_3$), 2.19 (s, 3H, ArCH$_3$), 3.00 (s, 6H, N(CH$_3$)$_2$) |
| 29 | 2.08 (s, 3H, ArCH$_3$), 2.22 (s, 3H, ArCH$_3$), 3.00 (s, 6H, N(CH$_3$)$_2$) |
| 31 | 2.07 (s, 3H, ArCH$_3$), 2.11 (s, 6H, ArCH$_3$), 2.36 (s, 3H, ArCH$_3$), 3.00 (s, 6H, N(CH$_3$)$_2$) |
| 32 | 2.08 (s, 3H, ArCH$_3$), 2.20 (s, 3H, ArCH$_3$), 3.01 (s, 6H, N(CH$_3$)$_2$) |
| 33 | 1.38 (t, 3H, CH$_2$CH$_3$), 2.09 (s, 3H, ArCH$_3$), 2.20 (s, 3H, ArCH$_3$), 3.03 (s, 6H, N(CH$_3$)$_2$), 4.35 (q, 2H, CH$_2$) |
| 34 | (s, 3H, ArCH$_3$), 2.19 (s, 3H, ArCH$_3$), 2.26 (s, 3H, ArCH$_3$), 3.00 (s, 6H, N(CH$_3$)$_2$) |
| 35 | 2.05 (s, 3H, ArCH$_3$), 2.20 (s, 3H, ArCH$_3$), 3.45–3.55 (br, 4H, CH$_2$), 3.75 (d, 4H, CH$_2$) |
| 37 | 1.20 (t, 6H, CH$_2$C$\underline{H}_3$), 2.10 (s, 3H, ArCH$_3$), 2.20 (s, 3H, ArCH$_3$), 3.30–3.50 (br, 4H, C$\underline{H}_2$CH$_3$) |
| 38 | 0.95 (t, 6H, CH$_2$C$\underline{H}_3$), 1.70 (br, 4H, CH$_3$C$\underline{H}_2$), 2.10 (s, 3H, ArCH$_3$), 2.20 (s, 3H, ArCH$_3$), 3.10–3.50 (br, 4H, NCH$_2$) |
| 39 | 1.00 (t, 6H, CH$_2$C$\underline{H}_3$), 1.35 (q, 4H, C$\underline{H}_2$CH$_3$), 1.60 (q, 4H, NCH$_2$C$\underline{H}_2$), 2.10 (s, 3H, ArCH$_3$), 2.20 (s, 3H, ArCH$_3$), 3.15–3.45 (br, 4H, NCH$_2$) |
| 40 | 1.3 (d, 12H, CCH$_3$), 2.10 (s, 3H, ArCH$_3$), 2.20 (s, 3H, ArCH$_3$), 3.6–4.9 (br, 2H, CH) |
| 42 | 2.10 (s, 3H, ArCH$_3$), 2.30 (s, 3H, ArCH$_3$), 3.55 (s, 3H, NCH$_3$) |
| 43 | 1.55–1.75 (m, 6H, C$\underline{H}_2$), 2.10 (s, 3H, ArCH$_3$), 2.20 (s, 3H, ArCH$_3$), 3.40 (br, 4H, NCH$_2$) |
| 45 | 1.20 (t, 3H, CH$_2$CH$_3$), 2.10 (s, 3H, ArCH$_3$), 2.20 (s, 3H, ArCH$_3$), 3.00 (s, 3H, NCH$_3$), 3.40 (br, 2H, NCH$_2$) |
| 50 | 2.10 (s, 3H, ArCH$_3$), 2.20 (s, 3H, ArCH$_3$), 3.00 (s, 6H, N(CH$_3$)$_2$) |
| 51 | 2.10 (s, 3H, ArCH$_3$), 2.20 (s, 3H, ArCH$_3$), 3.00 (s, 6H, N(CH$_3$)$_2$) |
| 52 | 2.18 (s, 6H, ArCH$_3$), 2.98 (s, 6H, N(CH$_3$)$_2$) |
| 53 | 2.00 (s, 3H, ArCH$_3$), 2.20 (s, 3H, ArCH$_3$), 3.00 (s, 6H, (NCH$_3$)$_2$) |
| 56 | 2.09 (s, 3H, ArCH$_3$), 2.19 (s, 3H, ArCH$_3$), 3.00 (s, 6H, N(CH$_3$)$_2$) and 3.77 (s, 3H, OCH$_3$) |
| 65 | 2.1 (s, 3H, ArCH$_3$), 2.2 (s, 3H, ArCH$_3$) and 3.0 (s, 6H, N(CH$_3$)$_2$) |
| 67 | 1.15 (d, 6H, CH(CH$_3$)$_2$), 2.10 (s, 3H, ArCH$_3$), 3.05 (s, 6H, N(CH$_3$)$_2$) and 3.43 (m, 1H, C$\underline{H}$(CH$_3$)$_2$) |
| 70 | 2.0 (s, 6H, ArCH$_3$O, 1.85 (s, 3H, CH$_3$), 1.90 (s, 3H, CH$_3$), 3.00 (s, 6H, N(CH$_3$)$_2$), 3.35 (s, 3H, NCH$_3$) |
| 71 | 2.05 (s, 3H, ArCH$_3$), 2.28 (s, 3H, ArCH$_3$) and 3.00 (s, 6H, N(CH$_3$)$_2$) |
| 74 | 2.06 (s, 3H, ArCH$_3$), 2.13 (s, 3H, ArCH$_3$), 3.00 (s, 6H, N(CH$_3$)$_2$) and 3.35 (s, 3H, CONCH$_3$) |
| 81 | 2.10 (s, 3H, ArCH$_3$), 2.20 (s, 3H, ArCH$_3$), 3.00 (s, 3H, N(CH$_3$)$_2$) |
| 83 | 2.21 (s, 3H, ArCH$_3$), 2.22 (s, 3H, ArCH$_3$), 3.02 (s, 6H, N(CH$_3$)$_2$) |
| 85 | 2.10 (s, 3H, ArCH$_3$), 2.19 (s, 3H, ArCH$_3$), 2.97 (s, 6H, N(CH$_3$)$_2$) |
| 90 | 2.16 (s, 3H, ArCH$_3$), 2.20 (s, 3H, ArCH$_3$), 3.01 (s, 6H, N(CH$_3$)$_2$) |
| 92 | 1.00 (t, 6H, (NCH$_2$CH$_3$)$_2$), 2.10 (s, 3H, ArCH$_3$), 2.20 (s, 3H, ArCH$_3$), 3.00 (s, 6H, N(CH$_3$)$_2$), 3.35 (m, 4H, N(C$\underline{H}_2$CH$_3$)$_2$) |
| 93 | 2.20 (s, 6H, ArCH$_3$), 3.00 (s, 6H, N(CH$_3$)$_2$) |
| 94 | 2.20 (s, 6H, ArCH$_3$), 3.00 (s, 6H, N(CH$_3$)$_2$) |
| 95 | 2.1 (s, 3H, ArCH$_3$), 2.20 (s, 3H, ArCH$_3$), 3.00 (s, 6H, N(CH$_3$)$_2$) |
| 99 | 1.30 (s, 9H, C(CH$_3$)$_3$), 2.30 (m, 6H, ArCH$_3$), |
| 100 | 1.20 (t, 3H, NCH$_2$CH$_3$), 1.30 (s, 9H, C(CH$_3$)$_3$), 2.10 (s, 3H, ArCH$_3$), 2.20 (s, 3H, ArCH$_3$), 3.0 (s, 3H, NCH$_3$), 3.40 (b, 2H, NC$\underline{H}_2$CH$_3$ |
| 104 | 2.12 (s, 3H, ArCH$_3$), 2.20 (s, 3H, ArCH$_3$), 2.37 (s, 3H, ArCH$_3$), 3.02 (s, 6H, N(CH$_3$)$_2$) |
| 105 | 1.30 (d, 6H, CHCH$_3$), 2.16 (s, 3H, ArCH$_3$), 2.20 (s, 3H, ArCH$_3$), 3.01 (s, 6H, N(CH$_3$)$_2$), 3.43 (m, 1H, C$\underline{H}$(CH$_3$)$_2$) |
| 108 | 1.30 (s, 3H, C(CH$_3$)$_3$), 1.95 (s, 3H, CCH$_3$), 2.15 (s, 3H, ArCH$_3$), 3.00 (s, 6H, N(CH$_3$)$_2$) |
| 109 | 1.30 (s, 9H, C(CH$_3$)$_3$), 2.20 (s, 3H, ArCH$_3$), 3.00 (s, 6H, N(CH$_3$)$_2$) |
| 110 | 1.00 (t, 3H, CH$_2$CH$_3$, 1.25 (s, 9H, C(CH$_3$)$_3$), 2.00 (s, 3H, ArCH$_3$), 2.10 (s, 3H, ArCH$_3$), 2.25 (q, 2H, C$\underline{H}_2$CH$_3$), 3.05 (s, 6H, N(CH$_3$)$_2$) |
| 113 | 1.31 (s, 9H, C(CH$_3$)$_3$), 2.19 (s, 3H, ArCH$_3$), 2.22 (s, 3H, ArCH$_3$), 3.03 (s, 6H, N(CH$_3$)$_2$), |
| 115 | 1.74 (s, 3H, pyrrCH$_3$), 2.00 (s, 3H, ArCH$_3$), 2.23 (s, 3H, ArCH$_3$), 3.01 (s, 6H, N(CH$_3$)$_2$) |
| 119 | 2.1 (s, 3H, ArCH$_3$), 2.2 (s, 3H, ArCH$_3$), 2.6 (s, 3H, SCH$_3$), 3.0 (s, 6H, N(CH$_3$)$_2$ |
| 121 | 2.15 (s, 3H, ArCH$_3$), 2.39 (s, 3H, ArCH$_3$), 2.99 (s, 6H, N(CH$_3$)$_2$), 3.42 (s, 3H, NCH$_3$) |
| 123 | 1.4 (s, 9H, C(CH$_3$)3) 2.2 (s, 3H, ArCH$_3$), 2.25 (s, 3H, ArCH$_3$), 3.0 (s, 6H, N(CH$_3$)$_2$) |
| 124 | 0.88 (t, 3H, CH$_2$CH$_3$), 1.27 (d, 3H, CHCH$_3$), 1.66 (m, 2H, CHC$\underline{H}_2$CH$_3$, 2,14 (s, 3H, ArCH$_3$), 2.20 (s, 3H, ArCH$_3$), 3.01 (s, 6H, N(CH$_3$)$_2$), 3.19 (m, 1H, C$\underline{H}$CH$_3$) |
| 125 | 2.10 (s, 3H, ArCH$_3$), 2.18 (s, 3H, ArCH$_3$), 3.00 (s, 6H, N(CH$_3$)$_2$) |
| 126 | 2.20–2.22 (m, 9H, ArCH$_3$, CH=CCH$_3$), 3.04 (S, 6H, N(CH$_3$)$_2$) |
| 128 | 2.26 (s, 3H, ArCH$_3$), 2.30 (s, 3H, ArCH$_3$), 3.00 (s, 6H, N(CH$_3$)$_2$), 4.07 (s, 2H, NCH$_2$) |
| 129 | 1.10 (t, 6H, NCH$_2$CH$_3$)$_2$), 2.12 (s, 3H, ArCH$_3$), 2.20 (s, 3H, ArCH$_3$), 3.00 (s, 6H, N(CH$_3$)$_2$), 3.22 (q, 4H, N(C$\underline{H}_2$CH$_3$)$_2$) |
| 130 | 0.82 (t, 3H, CHCH$_3$), 1.21 (d, 3H, CHCH$_3$), 1.57 (q, 2H, C$\underline{H}_2$CH$_3$), 2.10 (s, 3H, ArCH$_3$), 2.19 (s, 3H, ArCH$_3$), 2.54 (q, 1H, C$\underline{H}$CH$_3$), 3.01 (s, 6H, N(CH$_3$)$_2$) |
| 134 | 2.20 (s, 3H, ArCH$_3$), 2.23 (s, 3H, ArCH$_3$), 3.02 (s, 6H, N(CH$_3$)$_2$) |
| 135 | 2.08 (s, 3H, ArCH$_3$), 2.22 (s, 3H. ArCH$_3$), 3.04 (s, 6H, N(CH$_3$)$_2$) |
| 136 | 2.10 (s, 3H, ArCH$_3$), 2.20 (s, 3H, ArCH$_3$), 2.90–3.00 (m, 12H, 2xN(CH$_3$)$_2$) |
| 137 | 2.1 (s, 3H, ArCH$_3$), 2.2 (s, 3H, ArCH$_3$), 3.0 (s, 6H, N(CH$_3$)$_2$) |
| 138 | 2.2 (s, 3H, ArCH$_3$), 2.3 (s, 3H, ArCH$_3$), 3.1 (s, 6H, N(CH$_3$)$_2$) |
| 139 | 2.10 (s, 3H, ArCH$_3$), 2.20 (s, 3H, ArCH$_3$), 3.01 (s, 6H, N(CH$_3$)$_2$) |
| 140 | 1.35 (t, 3H, OCH$_2$CH$_3$), 2.05 (s, 3H, ArCH$_3$), 2.20 (s, 3H, ArCH$_3$) 2.28 (s, 3H, SCH$_3$), 3.00 (s, 6H, N(CH$_3$)$_2$), 4.35 (q, 2H, OC$\underline{H}_2$CH$_3$) |
| 141 | 2.20 (s, 3H, ArCH$_3$), 2.25 (s, 3H, ArCH$_3$), 3.05 (s, 6H, NCH$_3$) |
| 142 | 2.10 (s, 3H, ArCH$_3$), 2.20 (s, 3H, ArCH$_3$), 2.95 (s, 6H, N(CH$_3$)$_2$) |
| 143 | 1.85 (s, 3H, N=CCH$_3$), 2.05 (s, 3H, ArCH$_3$), 2.10 (s, 3H, ArCH$_3$), 3.05 (s, 6H, NCH$_3$) |
| 148 | 2.09 (s, 3H, ArCH$_3$), 2.26 (s, 3H, ArCH$_3$), 3.01 (s, 6H, N(CH$_3$)$_2$), |
| 149 | 1.20 (d, 6H, CH(CH$_3$)$_2$), 2.12 (s, 3H, ArCH$_3$), 2.20 (s, 3H, ArCH$_3$), 2.85 (m, 1H, C$\underline{H}$(CH$_3$)$_2$), 3.00 (s, 6H, N(CH$_3$)$_2$) |
| 150 | 2.09 (s, 3H, ArCH$_3$), 2.20 (s, 3H, ArCH$_3$), 2.57 (s, 3H, COCH$_3$), 3.03 (s, 6H, N(CH$_3$)$_2$) |
| 151 | 0.75 (s, 9H, C(CH$_3$)$_3$), 1.35 (s, 6H, C(CH$_3$)$_2$), 1.70 (s, 2H, CCH$_2$C), 2.10 (s, 3H, ArCH$_3$), 2.20 (s, 3H, ArCH$_3$), 3.00 (s, 6H, N(CH$_3$)$_2$) |
| 152 | 1.21 (d, 6H, CH(CH$_3$)$_2$), 2.10 (s, 3H, ArCH$_3$), 2.20 (s, 3H, ArCH$_3$), 2.83 (m, 1H, C$\underline{H}$(CH$_3$)$_2$), 3.00 (s, 6H, N(CH$_3$)$_2$) |
| 153 | 2.15 (s, 3H, ArCH$_3$), 2.3 (s, 3H, 3.0, ArCH$_3$), 3.00 (s, 6H, N(CH$_3$)$_2$) |
| 154 | 0.9 (m, 9H, CH$_3$(CH$_2$)3), 1.6 (m, 2H, CH$_2$), 2.05 (s, 3H, ArCH$_3$) 2.15 (s 3H, ArCH$_3$) 2.74 (m, 2H, ArCH$_2$) 3.0 (s, 6H, N(CH$_3$)$_2$) |
| 155 | 2.25 (s, 6H, ArCH$_3$), 2.55 (s, 6H, ArCH$_3$) 3.05 (s, 6H, N(CH$_3$)$_2$) |
| 156 | 2.0 (s, 3H, ArCH$_3$), 2.2 (s, 3H, ArCH$_3$), 3.0 (s, 6H, N(CH$_3$)$_2$) 3.8 (s, 2H, CH$_2$) |
| 157 | 1.95 (s, 3H, ArCH$_3$), 2.2 (s, 3H, ArCH$_3$), 3.0 (s, 6H, N(CH$_3$)$_2$) 3.85 (s, 2H, CH$_2$) |
| 158 | 1.95 (s, 3H, ArCH$_3$), 2.2 (s, 3H, ArCH$_3$), 3.0 (s, 6H, N(CH$_3$)$_2$), 3.85 (m, 5H, OCH$_3$, CH$_2$) |
| 159 | 2.3 (s, 6H, ArCH$_3$), 3.0 (s, 6H, N(CH$_3$)$_2$) |
| 160 | 2.2 (s, 6H, ArCH$_3$), 3.0 (s, 6H, N(CH$_3$)$_2$) |
| 161 | 1.2–1.9 (m, 10H, cyCH$_2$) 2.1 (s, 3H, ArCH$_3$), 2.2 (s, 3H, ArCH$_3$) 2.6 (m, 1H, CH) 3.0 (s, 6H, N(CH$_3$)$_2$) |
| 162 | 2.2 (s, 3H, ArCH$_3$), 2.3 (s, 3H, ArCH$_3$) 3.05 (s, 6H, N(CH$_3$)$_2$) |
| 163 | 2.2 (s, 3H, ArCH$_3$) 2.3 (s, 3H, ArCH$_3$) 3.05 (s, 6H, N(CH$_3$)$_2$) |
| 164 | 2.2 (s, 3H, ArCH$_3$), 2.3 (s, 3H, ArCH$_3$), 3.05 (s, 6H, N(CH$_3$)$_2$) |
| 165 | 2.15 (s, 3H, ArCH$_3$), 2.25 (s, 3H, ArCH$_3$), 2.5 (s, 3H, CH$_3$) 2.75 (s, 3H, CH$_3$) 3.0 (s, 6H, N(CH$_3$)$_2$) |
| 166 | 2.1 (s, 3H, ArCH$_3$), 2.25 (s, 3H, ArCH$_3$), 3.0 (s, 6H, N(CH$_3$)$_2$), 3.7 (s, 3H, CH$_3$) |
| 167 | 2.2 (s, 3H, ArCH$_3$), 2.25 (s, 3H, ArCH$_3$), 3.05 (s, 6H, N(CH$_3$)$_2$) |
| 168 | 2.15 (s, 3H, ArCH$_3$). 2.25 (s, 3H, ArCH$_3$) 3.0 (s, 6H, N(CH$_3$)$_2$, 4.15 (s, 3H, OCH$_3$) |
| 169 | 2.2 (s, 3H, ArCH$_3$) 2.25 (s, 3H, ArCH$_3$) 3.0 (s, 6H, N(CH$_3$)$_2$) |
| 170 | 0.70 (t, 3H, CH$_2$CH$_3$), 1.25 (s, 6H, C(CH$_3$)$_2$), 1.60 (q, 2H, C$\underline{H}_2$CH$_3$), 2.10 (s, 3H, ArCH$_3$), 2.20 (s, 3H, ArCH$_3$), 3.00 (s, 6H, NCH$_3$) |
| 171 | 1.20 (t, 3H, CH$_2$CH$_3$), 2.15 (s, 3H, ArCH$_3$), 2.20 (s, 3H, ArCH$_3$), 2.60 (q, 2H, C$\underline{H}_2$CH$_3$), 3.00 (s, 6H, N(CH$_3$)$_2$) |

TABLE 2-continued

| Cmp | Data |
|---|---|
| 172 | 0.70 (t, 3H, CH$_2$CH$_3$), 1.25 (s, 6H, CH$_3$), 1.60 (q, 2H, CH$_2$CH$_3$), 1.80 (s, 3H, N=CCH$_3$), 2.00 (s, 3H, ArCH$_3$), 2.10 (s, 3H, ArCH$_3$), 3.00 (s, 6H, N(CH$_3$)$_2$) |
| 173 | 2.09 (s, 3H, ArCH$_3$), 2.20 (s, 3H, ArCH$_3$), 2.30 (s, 3H, ArCH$_3$), 3.01 (s, 6H, N(CH$_3$)$_2$) |
| 174 | 2.10 (s, 3H, ArCH$_3$), 2.19 (s, 9H, ArCH$_3$), 3.01 (s, 6H, N(CH$_3$)$_2$) |
| 176 | 2.23 (s, 3H, ArCH$_3$), 2.35 (s, 3H, ArCH$_3$), 3.02 (s, 6H, N(CH$_3$)$_2$) |
| 177 | 2.22 (s, 3H, ArCH$_3$), 2.34 (s, 3H, ArCH$_3$), 3.01 (s, 6H, N(CH$_3$)$_2$), 6.74 (d, 1H, thiophH), 6.84 (d, 1H, thiophH) |
| 180 | 0.45–1.75 (m, 19H, C$_9$H$_{19}$), 2.10 (s, 3H, ArCH$_3$), 2.18 (s, 3H, ArCH$_3$), 3.00 (s, 6H, N(CH$_3$)$_2$) |
| 181 | 1.21 (t, 3H, CH$_2$CH$_3$), 2.10 (s, 3H, ArCH$_3$), 2.20 (s, 3H, ArCH$_3$), 2.60 (q, 2H, CH$_2$CH$_3$), 3.01 (s, 6H, N(CH$_3$)$_2$) |
| 182 | 2.15 (s, 3H, ArCH$_3$), 2.22 (s, 3H, ArCH$_3$), 3.04 (s, 6H, N(CH$_3$)$_2$) |
| 183 | 2.10 (s, 3H, ArCH$_3$), 2.20 (s, 3H, ArCH$_3$), 3.02 (s, 6H, N(CH$_3$)$_2$) |
| 184 | 2.10 (s, 3H, ArCH$_3$), 2.20 (s, 3H, ArCH$_3$), 3.01 (s, 6H, N(CH$_3$)$_2$), 2.40 (s, 3H, SCH$_3$) |
| 185 | 2.10 (s, 3H, ArCH$_3$), 2.20 (s, 3H, ArCH$_3$), 3.02 (s, 6H, N(CH$_3$)$_2$) |
| 186 | 1.60 (s, 6H, C(CH$_3$)$_2$), 2.00 (s, 3H, ArCH$_3$), 2.10 (s, 3H, ArCH$_3$), 2.95 (s, 6H, N(CH$_3$)$_2$) |
| 190 | 2.10 (s, 3H, ArCH$_3$), 2.20 (s, 3H, ArCH$_3$), 3.00 (s, 6H, N(CH$_3$)$_2$) |
| 191 | 1.00 (t, 6H, N(CH$_2$CH$_3$)$_2$), 1.76 (s, 3H, N=CCH$_3$), 1.97 (s, 3H, ArCH$_3$), 2.18 (s, 3H, ArCH$_3$), 3.00 (s, 6H, N(CH$_3$)$_2$), 3.35 (m, 4H, N(CH$_2$)$_2$) |
| 196 | 2.16 (s, 3H, ArCH$_3$), 2.19 (s, 3H, ArCH$_3$), 2.96 (s, 6H, N(CH$_3$)$_2$) |
| 197 | 2.20 (s, 3H, ArCH$_3$), 2.23 (s, 3H, ArCH$_3$), 3.02 (s, 6H, N(CH$_3$)$_2$) |
| 198 | 1.20 (d, 6H, CHCH$_3$)$_2$), 2.00 (s, 3H, ArCH$_3$), 2.05 (s, 3H, ArCH$_3$), 2.10 (s, 3H, ArCH$_3$), 2.95 (s, 6H, N(CH$_3$)$_2$), 3.30 (q, 1H, CH(CH$_3$)$_2$) |
| 199 | 1.25 (d, 3H, CHCH$_3$), 1.85 (s, 3H, =CCH$_3$), 2.00 (s, 3H, ArCH$_3$), 2.15 (s, 3H, ArCH$_3$), 2.20 (s, 3H, ArCH$_3$), 3.05 (s, 6H, N(CH$_3$)$_2$), 3.40 (q, 1H, CHCH$_3$) |
| 200 | 1.10 (t, 3H, CH$_2$CH$_3$), 2.05 (s, 3H, ArCH$_3$), 2.15 (s, 3H, ArCH$_3$), 2.60 (s, q, 2H, CH$_2$CH$_3$), 2.95 (s, 6H, N(CH$_3$)$_2$) |
| 201 | 1.15 (t, 3H, CH$_2$CH$_3$), 1.80 (s, 3H, =CCH$_3$), 1.95 (s, 3H, ArCH$_3$), 2.05 (s, 3H, ArCH$_3$), 2.65 (q, 2H, CH$_2$CH$_3$), 3.00 (s, 6H, N(CH$_3$)$_2$) |
| 202 | 2.10 (s, 3H, ArCH$_3$), 2.20 (s, 3H, ArCH$_3$), 2.233 (s, 3H, ArCH$_3$), 2.40 (s, 3H, SCH$_3$), 3.01 (s, 6H, N(CH$_3$)$_2$) |
| 203 | 2.10 (s, 3H, ArCH$_3$), 2.22 (s, 3H, ArCH$_3$), 3.02 (s, 6H, N(CH$_3$)$_2$) |
| 204 | 1.20 (t, 3H, CH$_2$CH$_3$), 2.08 (s, ArCH$_3$), 2.20 (s, ArCH$_3$), 2.92 (q, CH$_2$CH$_3$), 3.02 (s, 6H, N(CH$_3$)$_2$) |
| 207 | 2.30 (s, 3H, ArCH$_3$), 3.05 (s, 6H, N(CH$_3$)$_2$) |
| 208 | 1.20 (s, 6H, CH(CH$_3$)$_2$) 2.20 (s, 3H, ArCH$_3$) 3.05 (s, 6H, N(CH$_3$)$_2$), 3.30 (q, 1H, CH(CH$_3$)$_2$) |
| 209 | 1.85 (s, 3H, NCCH$_3$) 2.10 (s, 3H, ArCH$_3$) 3.10 (s, 6H, N(CH$_3$)$_2$) |
| 210 | 1.47 (s, 9H, C(CH$_3$)$_3$), 2.32 (s, 3H, ArCH$_3$), 3.04 (s, 6H, N(CH$_3$)$_2$) |
| 213 | 2.13 (s, 3H, ArCH$_3$), 2.20 (s, 3H, ArCH$_3$), 3.00 (s, 6H, N(CH$_3$)$_2$) |
| 214 | 2.2 (s, 3H, ArCH$_3$), 2.3 (s, 3H, ArCH$_3$), 3.0 (s, 6H, N(CH$_3$)$_2$), 5.2 (s, 1H, CHCN) |
| 215 | 2.16 (s, 3H, ArCH$_3$), 2.18 (s, 3H, ArCH$_3$), 2.97 (s, 6H, N(CH$_3$)$_2$) |
| 216 | 2.10–2.25 (s, 9H, ArCH$_3$), 3.00 (s, 6H, N(CH$_3$)$_2$) |
| 217 | 2.17 (s, 3H, ArCH$_3$), 2.18 (s, 3H, ArCH$_3$), 2.99 (s, 6H, N(CH$_3$)$_2$), 3.78 (s, 3H, OCH$_3$) |
| 219 | 2.10 (s, 3H, ArCH$_3$), 2.22 (s, 3H, ArCH$_3$), 3.02 (s, 6H, N(CH$_3$)$_2$) |
| 220 | 2.20 (s, 6H, ArCH$_3$), 3.01 (s, 6H, N(CH$_3$)$_2$), 5.18 (s, 2H, ArCH$_2$O) |
| 221 | 2.10 (s, 3H, ArCH$_3$), 2.19 (s, ArCH$_3$), 3.00 (s, 6H, N(CH$_3$)$_2$), 5.92 (s, 2H, OCH$_2$O) |
| 222 | 2.10 (s, 3H, ArCH$_3$), 2.20 (s, 3H, ArCH$_3$), 2.27 (s, 6H, ArCH$_3$), 3.01 (s, 6H, N(CH$_3$)$_2$) |
| 223 | 2.10 (s, 3H, ArCH$_3$), 2.20 (s, 3H, ArCH$_3$), 3.01 (s, 6H, N(CH$_3$)$_2$), 3.73 (s, 6H, OCH$_3$) |
| 224 | 2.10 (s, 3H, ArCH$_3$), 2.25 (s, 3H, ArCH$_3$), 3.00 (s, 6H, N(CH$_3$)$_2$) |
| 225 | 1.25 (m, 3H, NCH$_2$CH$_3$), 2.20 (s, 3H, ArCH$_3$), 2.25 (s, 3H, ArCH$_3$), 2.35 (m, 2H, NCH$_2$CH$_3$), 3.00 (s, 3H, NCH$_3$) |
| 227 | 2.35 (m, 6H, Ar(CH$_3$)$_2$) |
| 230 | 1.22 (d, 6H, CH(CH$_3$)$_2$), 1.82 (s, 3H, N=CCH$_3$), 2.00 (s, 3H, ArCH$_3$), 2.10 (s, 3H, ArCH$_3$), 3.03 (s, 6H, N(CH$_3$)$_2$), 3.30 (q, 1H, CH(CH$_3$)$_2$) |
| 231 | 2.1 (s, 3H, ArCH$_3$), 2.15 (s, 3H, ArCH$_3$), 2.9 (s, 6H, N(CH$_3$)$_2$) 3.7 (s, 3H, OCH$_3$), 5.1 (s, 1H, CHCO$_2$CH$_3$) |
| 232 | 1.30 (t, 3H, NCH$_2$CH$_3$), 2.30 (m, 8H, Ar(CH$_3$)$_2$) + NCH$_2$CH$_3$), 3.45(br, 1H, NH) |
| 233 | 1.47 (s, 9H, C(CH$_3$)$_3$), 1.79 (s, 3H, N=CCH$_3$), 2.15 (s, 3H, ArH), 3.06 (s, 6H, N(CH$_3$)$_2$) |
| 235 | 2.12 (s, 3H, ArCH$_3$), 2.20 (s, 3H, ArCH$_3$), 2.50 (m, 1H, CH$_2$CCH), 3.00 (s, 6H, N(CH$_3$)$_2$), 4.60 (d, 2H, CH$_2$CCH) |
| 236 | 2.10 (s, 3H, ArCH$_3$) 2.20 (s, 3H, ArCH$_3$) 3.00 (s, 6H, N(CH$_3$)$_2$) |
| 237 | 1.90 (s, 3H, NCCH$_3$), 2.30 (s, 3H, ArCH$_3$), 3.10 (s, 6H, N(CH$_3$)$_2$) |
| 238 | 1.75 (s, 3H, N=CCH$_3$), 1.95 (s, 3H, ArCH$_3$), 2.02 (s, ArCH$_3$), 3.00 (s, 6H, N(CH$_3$)$_2$) |
| 239 | 1.15 (t, 3H, CH$_2$CH$_3$), 1.75 (s, 3H, N=CCH$_3$), 1.95 (s, 3H, ArCH$_3$), 2.05 (s, ArCH$_3$), 2.54 (q, 2H, CH$_2$CH$_3$), 3.00 (s, 6H, N(CH$_3$)$_2$) |
| 240 | 1.75 (s, 3H, N=CCH$_3$), 1.95 (s, 3H, ArCH$_3$), 2.05 (s, ArCH$_3$), 3.00 (s, 6H, N(CH$_3$)$_2$) |
| 241 | 1.75 (s, 3H, N=CCH$_3$), 1.95 (s, 3H, ArCH$_3$), 2.02 (s, ArCH$_3$), 3.00 (s, 6H, N(CH$_3$)$_2$) |
| 242 | 1.80 (s, 3H, N=CCH$_3$), 1.95 (s, 3HArCH$_3$), 2.02 (s, 3H, ArCH$_3$), 2.40 (s, 3H, SCH$_3$), 3.00 (s, 6H, N(CH$_3$)$_2$) |
| 243 | 1.75 (s, 3H, N=CCH$_3$), 1.95 (s, 3H, ArCH$_3$), 2.00 (s, ArCH$_3$), 3.00 (s, 6H, N(CH$_3$)$_2$) |
| 244 | 1.75 (s, 3H, N=CCH$_3$), 1.95 (s, 3H, ArCH$_3$), 2.00 (s, ArCH$_3$), 3.00 (s, 6H, N(CH$_3$)$_2$) |
| 245 | 1.15 (t, 3H, CH$_2$CH$_3$), 1.78 (s, 3H, N=CCH$_3$), 1.93 (s, 3H, ArCH$_3$), 1.99 (s, ArCH$_3$), 2.88 (s, 2H, CH$_2$CH$_3$), 3.00 (s, 6H, N(CH$_3$)$_2$) |
| 246 | 1.70 (m, 6H, CH$_2$CH$_2$CH$_2$), 2.20 (s, 3H, ArCH$_3$), 2.25 (s, 3H, ArCH$_3$), 3.50 (m, 4H, CH$_2$NCH$_2$) |
| 247 | 2.3 (s, 3H, ArCH$_3$), 3.04 (s, 6H, N(CH$_3$)$_2$) |
| 248 | 0.20 (s, 9H, Si(CH$_3$)$_3$), 2.05 (s, 3H, ArCH$_3$), 2.15 (s, 3H, ArCH$_3$), 2.95 (s, 6H, N(CH$_3$)$_2$) |
| 249 | 2.10 (s, 3H, ArCH$_3$), 2.20 (s, 3H, ArCH$_3$), 3.00 (s, 6H, N(CH$_3$)$_2$) 3.1 (s, 1H, CCH) |
| 251 | 1.15 (d, 6H, CH(CH$_3$)$_2$), 2.15 (s, 3H, ArCH$_3$), 2.20 (s, 3H, ArCH$_3$), 2.30 (s, 3H, ArCH$_3$), 3.00 (s, 6H, N(CH$_3$)$_2$) 3.30 (q, 1H, CH(CH$_3$)$_2$) |
| 254 | 1.00 (t, 3H, CH$_2$CH$_3$), 2.10 (s, 3H, ArCH$_3$), 2.20, (s, 3H, ArCH$_3$), 2.25 (q, 2H, CH$_2$CH$_3$), 3.05 (s, 6H, N(CH$_3$)$_2$) |
| 255 | 1.05 (t, 3H, CH$_2$CH$_3$), 2.20 (s, 3H, ArCH$_3$), 2.30 (m, 2H, CH$_2$CH$_3$), 3.00 (s, 6H, N(CH$_3$)$_2$) |
| 256 | 1.10 (d, 6H, CH(CH$_3$)$_2$), 2.05 (s, 3H, ArCH$_3$), 2.10 (s, 3H, ArCH$_3$), 2.20 (s, 3H, ArCH$_3$), 2.95 (s, 6H, NCH$_3$) 3.30 (q, 1H, CH(CH$_3$)$_2$) |
| 257 | 0.85 (s, 9H, C(CH$_3$)$_3$), 3.00 (s, 6H, N(CH$_3$)$_2$) |
| 268 | 2.10 (s, 3H, ArCH$_3$), 2.21 (s, 3H, ArCH$_3$), 3.01 (s, 6H, N(CH$_3$)$_2$) |
| 260 | 1.00 (s, 9H, C(CH$_3$)$_3$), 3.05 (S. 6H, N(CH$_3$)$_2$) |
| 261 | 2.15 (s, 3H, ArCH$_3$), 2.20 (s, 3H, ArCH$_3$), 3.00 (s, 6H, N(CH$_3$)$_2$), 5.00 (s, 2H, OCH$_2$Ph) |
| 262 | 2.15 (s, 3H, ArCH$_3$), 2.25 (s, 3H, ArCH$_3$), 3.00 (s, 6H, N(CH$_3$)$_2$) |
| 263 | 2.10 (s, 3H, ArCH$_3$), 2.18 (s, 3H, ArCH$_3$), 3.03(s, 6H, 2N(CH$_3$)$_2$) |
| 265 | 2.15 (s, 3H, ArCH$_3$), 2.10 (s, 3H, ArCH$_3$), 3.00 (s, 6H, N(CH$_3$)$_2$) |
| 266 | 2.15 (s, 3H, ArCH$_3$), 2.10 (s, 3H. ArCH$_3$), 3.00 (s, 6H, N(CH$_3$)$_2$), 5.00 (s, 2H, CH$_2$) |
| 267 | 0.9–1.3 (m, 5H), 1.6–1.8 (m ,6H), 2.1 (s 3H), 2.15 (s, 3H), 3.6 (d, 2H), 2.95 (d, 6H) |
| 268 | 2.1 (s, 3H, ArCH$_3$), 2.2 (s, 3H, ArCH$_3$), 2.9 (s, 6H, N(CH$_3$)$_2$), 4.2 (m, 4H, O(CH$_2$)$_2$O) |
| 269 | 1.2 (s, 9H, C(CH$_3$)$_3$), 2.1 (s, 3H, ArCH$_3$) 2.15 (s, 3H, ArCH$_3$), 2.9 (s, 6H, N(CH$_3$)$_2$) 4.1–4.25 (br, 4H, O(CH$_2$)$_2$O) |
| 270 | 1.85–2.0 (m, 4H, CH$_2$CH$_2$) 2.1 (s, 3H, ArCH$_3$), 2.15 (s, 3H, ArCH$_3$), 2.9 (s, 6H, N(CH$_3$)$_2$), 3.8–4.0 (m, 4H, OCH$_2$, OCH$_2$) |
| 271 | 1.65–1.9 (m, 4H, (CH$_2$)$_2$, 2.1 (s, 3H, ArCH$_3$), 2.2 (s, 3H, ArCH$_3$), 2.9 (s, 6H, N(CH$_3$)$_2$), 3.65–3.9 (m, 4H, OCH$_2$, NCH$_2$) |
| 272 | 1.4–1.8 (m, 6H, (CH$_2$)$_3$), 2.1 (s, 3H, ArCH$_3$), 2.2 (s, 3H, ArCH$_3$), 2.9 (s, 6H, N(CH$_3$)$_2$), 3.8 (m, 4H, OCH$_2$, ArCH$_2$) |
| 273 | 1.2 (s, 9H, C(CH$_3$)$_3$), 1.90 (m, 2H, CH$_2$), 2.1 (s, 3H, ArCH$_3$), 2.2 (s, 3H, ArCH$_3$), 2.9 (s, 6H, N(CH$_3$)$_2$), 3.95–4.1 (m, 4H, (CH$_2$)$_3$) |
| 274 | 1.1–1.2 (m, 2H, CH$_2$), 1.3 (s, 9H, C(CH$_3$)$_3$), 1.9–2.0 (m, 2H, CH$_2$), 2.1 (s, 3H, ArCH$_3$), 2.2 (s, 3H, ArCH$_3$), 2.9 (s, 6H, N(CH$_3$)$_2$), 3.9–4.0 (m, 4H, OCH$_2$, OCH$_2$) |
| 275 | 1.25 (s, 9H, C(CH$_3$)$_3$), 1.9 (brs, 4H, (CH$_2$)$_2$), 2.1 (s, 3H, ArCH$_3$), 2.2 (s, 3H, ArCH$_3$), 2.9 (s, 6H, N(CH$_3$)$_2$), 3.8–4.0 (br.d, 4H, O(CH$_2$), OCH$_2$) |
| 276 | 1.35–1.8 (m, 6H, (CH$_2$)$_3$), 2.1 (d, 6H, Ar(CH$_3$)$_2$), 2.9 (s, 6H, N(CH$_3$)$_2$), 3.45 (m, 1H, CH) 3.6–4.0 (m, 4H, OCH$_2$, OCH$_2$) |
| 277 | 2.1 (s, 3H, ArCH$_3$), 2.2 (s, 3H, ArCH$_3$), 2.2 (s, 2H, CH$_2$), 2.9 (s, 6H, N(CH$_3$)$_2$), 4.05 (m, 2H, CH$_2$), 4.1 (m, 2H, CH$_2$) |
| 278 | 1.2–1.8 (m, 20H, (CH$_2$)$_{10}$), 2.05 (s, 3H, ArCH$_3$), 2.2 (s, 3H, ArCH$_3$), 2.9 (s, 6H, N(CH$_3$)$_2$), 3.3 (m, 1H, CH), 3.45 (m, 1H, CH), 3.7 (m, 1H, CH), 3.8–3.9 (m, 3H, CH + CH$_2$), 4.5 (m, 1H, CH) |

TABLE 2-continued

| Cmp | Data |
|---|---|
| 279 | 2.15 (d, 6H, (ArCH$_3$)$_2$), 2.9 (s, 6H, N(CH$_3$)$_2$), 3.6 (s, 3H, OCH$_3$), 3.75 (s, 3H, COOCH$_3$), 4.8 (s, 2H, CH$_2$) |
| 280 | 2.05 (s, 3H, ArCH$_3$), 2.15 (s, 3H, ArCH$_3$), 2.9 (s, 6H, N(CH$_3$)$_2$), 3.0 (m, 2H, CH$_2$), 4.05 (m, 2H, CH$_2$) |
| 281 | 0.95 (t, 3H, CH$_2$CH$_3$), 1.30 (s, 9H, CCH$_3$), 1.65 (q, 2H, C$\underline{H}$$_2$CH$_3$), 2.20 (s, 3H, ArCH$_3$), 2.25 (s, 3H, ArCH$_3$), 3.05 (s, 3H, NCH$_3$), 3.30 (m, 2H, NCH$_2$) |
| 282 | 0.90 (t, 3H, CH$_2$CH$_3$), 1.20 (s, 9H, CCH$_3$), 1.30 (m, 2HCH$_2$CH$_2$), 1.50 (m, 2H, CH$_2$CH$_2$), 2.05 (s, 3H, ArCH$_3$), 2.10 (s, 3H, ArCH$_3$), 2.90 (s, 3H, NCH$_3$), 3.20 (m, 2H, NCH$_2$) |
| 283 | 1.25 (d, 6H, CH(CH$_3$)$_2$), 1.30 (s, 9H, C(CH$_3$)$_3$), 2.15 (s, 3H, ArCH$_3$), 2.20 (s, 3H, ArCH$_3$), 2.90 (s, 3H, N(CH$_3$)$_2$), 3.70 (m, 1H, C$\underline{H}$(CH$_3$)$_2$) |
| 284 | 1.30 (s, 9H, C(CH$_3$)$_3$), 2.20 (s, 3H, ArCH$_3$), 2.25 (s, 3H, ArCH$_3$), 3.00 (s, 3H, NCH$_3$), 3.95 (m, 2H, NCH$_2$), 5.25 (d, 2H, CH=C$\underline{H}$$_2$), 5.90 (m, 1H, C$\underline{H}$=CH$_2$) |
| 285 | 1.00 (t, 3H, CH$_2$CH$_3$), 1.25 (t, 3H, CH$_2$CH$_3$), 1.30 (s, 9H, C(CH$_3$)$_3$), 1.40 (q, 2H, C$\underline{H}$$_2$CH$_3$), 1.65 (m, 2H, CH$_2$CH$_2$), 2.20 (s, 3H, ArCH$_3$), 2.25 (s, 3H, ArCH$_3$), 3.40 (m, 4H, NCH$_2$, NCH$_2$) |
| 286 | 1.15 (t, 6H, (CH$_2$CH$_3$)$_2$), 1.20 (s, 9H, C(CH$_3$)$_3$), 2.05 (s, 3H, ArCH$_3$), 2.15 (s, 3H, ArCH$_3$), 3.35 (m, 4H, N(C$\underline{H}$$_2$CH$_3$)$_2$) |
| 287 | 1.50 (s, 9H, C(CH$_3$)$_3$), 2.00 (s, 3H, ArCH$_3$) 2.20 (s, 3H, ArCH$_3$), 2.95 (s, 6H, N(CH$_3$)$_2$) |
| 288 | 1.21 (m, 9H, C$\underline{H}$$_2$CH$_3$, C(CH$_3$)$_3$), 2.15 (d, 6H, ArCH$_3$), 3.00 (s, 6H, N(CH$_3$)$_2$), 3.61 (m, 1H, C$\underline{H}$$_2$CH$_3$), 3.05 (s, 6H, N(CH$_3$)$_2$), 3.92 (m, 1H, C$\underline{H}$$_2$CH$_3$) |
| 289 | 1.20–1.80 (m, 10H, C$_5$H$_{10}$), 2.05 (s, 3H, ArCH$_3$), 2.20 (s, 3H, ArCH$_3$), 3.00 (s, 6H, N(CH$_3$)$_2$), 3.90 (m, 1H, SCH) |
| 290 | 0.80–2.00 (m, 11H, C$_6$H$_{11}$), 2.15 (s, 3H, ArCH$_3$), 2.18 (s, 3H, ArCH$_3$), 3.00 (s, 6H, N(CH$_3$)$_2$), 3.70 (d, 2H, OCH$_2$C$_6$H$_{11}$) |
| 291 | 1.30 (d, 6H, CH(CH$_3$)$_2$), 2.10 (s, 3H, ArCH$_3$), 2.20 (s, 3H, ArCH$_3$), 3.00 (s, 6H, N(CH$_3$)$_2$), 4.45 (m, 1H, C$\underline{H}$(CH$_3$)$_2$) |
| 292 | 2.22 (s, 3H, ArCH$_3$), 3.00 (s, 6H, N(CH$_3$)$_2$), 4.20 (t, 2H, OCH$_2$CH$_2$O), 4.35 (t, 2H, OCH$_2$CH$_2$) |
| 294 | 3.00 (s, 6H, N(CH$_3$)$_2$) |
| 295 | 2.00 (m, 6H, (ArCH$_3$)$_2$), 2.95 (m, 6H, N(CH$_3$)$_2$), 3.30 (m, 2H, ArCH$_2$CH$_2$), 4.05 (m, 2H, ArCH$_2$CH$_2$) |
| 296 | 2.10 (s, 3H, ArCH$_3$), 2.20 (s, 3H, ArCH$_3$), 3.00 (s, 6H, N(CH$_3$)$_2$), 5.05 (s, 2H, ArCH$_2$O) |
| 297 | 1.25 (s, 9H, C(CH$_3$)$_3$), 3.00 (s, 6H, N(CH$_3$)$_2$) |
| 298 | 2.10 (s, 3H, ArCH$_3$), 2.15 (s, 3H, ArCH$_3$), 3.05 (s, 6H, N(CH$_3$)$_2$) |
| 301 | 2.10 (s, 3H, ArCH$_3$), 2.20 (s, 3H, ArCH$_3$), 3.00 (s, 6H, N(CH$_3$)$_2$), 5.05 (s, 2H, ArCH$_2$O) |
| 302 | 0.90 (d, 6H, CH(CH$_3$)$_2$), 1.70 (m, 2H, C$\underline{H}$$_2$CH(CH$_3$)$_2$), 1.78 (m, 1H, C$\underline{H}$(CH$_3$)$_2$), 2.15 (s, 6H, Ar(CH$_3$)$_2$), 3.00 (s, 6H, N(CH$_3$)$_2$), 4.03 (t, 2H, OC$\underline{H}$$_2$CH$_2$) |
| 303 | 1.33 (d, 6H, CH(CH$_3$)$_2$), 2.15 (s, 3H, ArCH$_3$), 2.20 (s, 3H, ArCH$_3$), 3.00 (s, 6H, N(CH$_3$)$_2$), 4.42 (m, 1H, CH(CH$_3$)$_2$) |
| 304 | 1.00 (s, 9H, C(CH$_3$)$_3$), 2.10 (s, 3H, ArCH$_3$), 2.15 (s, 3H, ArCH$_3$) 3.15 (s, 6H, N(CH$_3$)$_2$) |
| 305 | 2.20 (s, 6H, Ar(CH$_3$)$_2$), 3.00 (s, 6H, N(CH$_3$)$_2$), 5.20 (s, 2H, ArCH$_2$O) |
| 306 | 2.22 (s, 3H, ArCH$_3$), 3.00 (s, 6H, N(CH$_3$)$_2$), 5.15 (s, 2H, ArCH$_2$O) |
| 310 | 1.20 (t, 3H, CH$_2$CH$_3$), 2.10 (s, 3H, ArCH$_3$), 2.25 (s, 3H, ArCH$_3$), 3.00 (s, 3H, NCH$_3$), 3.40 (m, 2H, C$\underline{H}$$_2$CH$_3$) |
| 311 | 1.25 (m, 9H, CH$_2$CH$_3$ + CH(CH$_3$)$_2$), 2.15 (s, 3H, ArCH$_3$), 2.25 (s, 3H, ArCH$_3$), 2.90 (q, 1H, C$\underline{H}$(CH$_3$)$_2$), 3.05 (s, 3H, NCH$_3$), 3.40 (m, 2H, C$\underline{H}$$_2$CH$_3$) |
| 312 | 1.25 (t, 3H, CH$_2$CH$_3$), 2.10 (s, 3H, ArCH$_3$), 2.20 (s, 3H, ArCH$_3$), 3.00 (s, 3H, NCH$_3$), 3.40 (m, 2H, C$\underline{H}$$_2$CH$_3$), 3.75 (s, 3H, OCH$_3$) |
| 313 | 0.70 (t, 3H, CH$_2$CH$_3$), 1.25 (t, 3H, C$\underline{H}$$_2$CH$_3$), 1.30 (s, 6H, C(CH$_3$)$_2$), 1.65 (q, 2H, C$\underline{H}$$_2$CH$_3$), 2.15 (s, 3H, ArCH$_3$), 2.20 (s, 3H, ArCH$_3$), 3.00 (s, 3H, NCH$_3$), 3.40 (b, 2H, NCH$_2$) |
| 314 | 0.70–1.70 (m, 24H, C$_{10}$H$_{21}$ + CHCH$_3$), 2.02 (s, 3H, ArCH$_3$), 2.10 (s, 3H, ArCH$_3$), 2.95 (s, 6H, N(CH$_3$)$_2$), 4.20 (m, 1H, OCH(CH$_3$)C) |
| 315 | 1.30 (d, 6H, CH(CH$_3$)$_2$), 2.18 (s, 6H, Ar(CH$_3$)$_2$), 3.00 (s, 6H, N(CH$_3$)$_2$), 4.55 (m, 1H, C$\underline{H}$(CH$_3$)$_2$) |
| 316 | 1.10 (d, 12H, CH(CH$_3$)$_2$), 2.00 (s, 3H, ArCH$_3$), 2.10 (s, 3H, ArCH$_3$), 3.00 (s, 6H, N(CH$_3$)$_2$) |
| 317 | 2.10 (s, 3H, ArCH$_3$), 2.19 (s, 3H, ArCH$_3$), 2.26 (s, 3H, ArCH$_3$), 3.01 (s, 6H, N(CH$_3$)$_2$), 3.47 (s, 3H, OCH$_3$) |
| 318 | 2.10 (s, 3H, ArCH$_3$) 2.19 (s, 3H, ArCH$_3$), 3.00 (s, 6H, N(CH$_3$)$_2$) |
| 319 | 0.75–1.85 (m, 24H, C$_{10}$H$_{21}$ + CHCH$_3$), 2.18 (s, 6H, Ar(CH$_3$)$_2$), 3.00 (s, 6H, N(CH$_3$)$_2$), 4.38 (m, 1H, C$_{10}$H$_{21}$CHCH$_3$) |
| 320 | 0.90 (d, 6H, CH(CH$_3$)$_2$), 1.60 (t, 2H, OCH$_2$C$\underline{H}$$_2$CH), 1.70 (m 1HC$\underline{H}$(CH$_3$)$_2$), 2.20 (s, 3H, ArCH$_3$), 3.00 (s, 6H, N(CH$_3$)$_2$), 4.00 (t, 2H, OC$\underline{H}$$_2$CH$_2$) |
| 321 | 1.30 (d, 6H, CH(CH$_3$)$_2$), 2.25 (s, 3H, ArCH$_3$), 3.00 (s, 6H, N(CH$_3$)$_2$), 4.50 (m, 1H, C$\underline{H}$(CH$_3$)$_2$) |
| 323 | 2.20 (m, 6H, ArCH$_3$), 8.60–8.35 (m, 1H, NH) |
| 324 | 1.30 (s, 9H, C(CH$_3$)$_3$), 2.25 (m, 6H, ArCH$_3$), 8.30–8.60 (m, 1H, NH) |
| 325 | 1.25 (t, 3H, CH$_2$CH$_3$), 2.15 (s, 3H, ArCH$_3$), 2.25 (s, 3H, ArCH$_3$), 3.00 (s, 3H, NCH$_3$), 3.40 (m, 2H, C$\underline{H}$$_2$CH$_3$) |
| 326 | 1.30 (s, 9H, C(CH$_3$)$_3$)), 1.25 (t, 3H, CH$_2$CH$_3$), 2.15 (s, 3H, ArCH$_3$), 2.25 (s, 3H, ArCH$_3$), 3.00 (s, 3H, NCH$_3$), 3.40 (m, 2H, NC$\underline{H}$$_2$CH$_3$) |
| 328 | 2.20 (s, 3H, ArCH$_3$), 2.24 (s, 3H, ArCH$_3$), 3.02 (s, 6H, N(CH$_3$)$_2$) |
| 329 | 2.00 (s, 3H, ArCH$_3$), 2.15 (s, 3H, ArCH$_3$), 2.95 (s, 3H, NCH$_3$), 3.85 (m, 2H, NCH$_2$), 5.15 (d, 2H, CHC$\underline{H}$$_2$), 5.80 (m, 1H, C$\underline{H}$CH$_2$) |
| 330 | 1.20 (d, 3H, CH(CH$_3$)$_2$), 2.00 (s, 3H, ArCH$_3$), 2.15 (s, 3H, ArCH$_3$), 2.85 (s, 3H, NCH$_3$), 3.60 (m, 1H, C$\underline{H}$CH$_3$) |
| 331 | 0.90 (t, 3H, CH$_2$CH$_3$), 1.30 (m, 2H, CH$_2$CH$_2$), 1.55 (m, 2H, CH$_2$CH$_2$), 2.00 (s, 3H, ArCH$_3$), 2.15 (s, 3H, ArCH$_3$), 2.95 (s, 3H, NCH$_3$), 3.20 (m, 2H, NCH$_2$) |
| 334 | 2.10 (s, 3H, ArCH$_3$), 2.20 (s, 3H, ArCH$_3$), 3.00 (s, 6H, N(CH$_3$)$_2$) |
| 335 | 1.25 (t, 3H, CH$_2$CH$_3$), 2.10 (s, 3H, ArCH$_3$), 2.25 (s, 3H, ArCH$_3$), 3.00 (s, 3H, NCH$_3$), 3.40 (m, 2H, C$\underline{H}$$_2$CH$_3$) |
| 336 | 2.10 (s, 3H, ArCH$_3$), 2.20 (s, 3H, ArCH$_3$),3.00 (s, 6H, N(CH$_3$)$_2$) |
| 340 | 0.93 (d, 6H, CH(CH$_3$)$_2$), 1.60 (t, 2H, OCH$_2$C$\underline{H}$$_2$CH), 1.80 (m, 1H, C$\underline{H}$(CH$_3$)$_2$), 2.10 (s, 3H, ArCH$_3$), 2.20 (s, 3H, ArCH$_3$), 3.00 (s, 6H, N(CH$_3$)$_2$), 3.90 (t, 2H, OC$\underline{H}$$_2$CH$_2$) |
| 341 | 0.70–1.85 (m, 11H, C$_6$H$_{11}$), 2.05 (s, 3H, ArCH$_3$), 2.13 (s, 3H, ArCH$_3$), 2.92 (s, 6H, N(CH$_3$)$_2$), 3.60 (d, 2H, OCH$_2$Ar) |
| 342 | 2.15 (s, 3H, ArCH$_3$), 2.23 (s, 3H, ArCH$_3$), 3.00 (s, 6H, N(CH$_3$)$_2$), 5.00 (s, 2H, OCH$_2$Ar) |
| 343 | 2.10 (s, 3H, ArCH$_3$), 2.20 (s, 3H, ArCH$_3$), 2.50 (d, 1H, CH$_2$CC$\underline{H}$), 3.00 (s, 6H, N(CH$_3$)$_2$), 4.60 (d, 2H, OC$\underline{H}$$_2$CCH) |
| 344 | 2.12 (s, 3H, ArCH$_3$), 2.22 (s, 3H, ArCH$_3$), 3.00 (s, 6H, N(CH$_3$)$_2$), 4.45 (d, 2H, OCH$_2$CHC$\underline{H}$$_2$), 5.22–5.42 (m, 2H, OCH$_2$CHCH$_2$), 6.00 (m, 1H, OCH$_2$C$\underline{H}$CH$_2$) |
| 345 | 2.15 (s, 3H, ArCH$_3$), 2.20 (s, 3H, ArCH$_3$), 3.00 (s, 6H, N(CH$_3$)$_2$), 4.25 (brs, 4H, ArOCH$_2$CH$_2$O) |
| 346 | 2.15 (s, 3H, ArCH$_3$), 2.20 (s, 3H, ArCH$_3$), 3.30 (s, 6H, N(CH$_3$)$_2$) |
| 347 | 1.25 (s, 9H, C(CH$_3$)$_3$), 2.10 (s, 3H, ArCH$_3$), 2.30 (s, 3H, ArCH$_3$), 3.05 (b, 6H, N(CH$_3$)$_2$) |
| 348 | 0.30 (m, 2H, cyCH$_2$), 0.60 (m, 2H, cyCH$_2$), 1.20 (m, 1H, cyCH), 2.10 (s, 3H, ArCH$_3$), 2.20 (s, 3H, ArCH$_3$), 3.00 (s, 6H, N(CH$_3$)$_2$), 3.72 (d, 2H, OCH$_2$C$_3$H$_5$) |
| 349 | 2.10 (s, 3H, ArCH$_3$), 2.20 (s, 3H, ArCH$_3$), 3.00 (s, 6H, N(CH$_3$)$_2$), 5.20 (s, 2H, COCH$_2$O) |
| 350 | 2.07 (s, 3H, ArCH$_3$), 2.20 (s, 3H, ArCH$_3$), 3.75 (s, 3H, OCH$_3$), 4.52 (s, 2H, COCH$_2$O) |
| 352 | 2.10 (s, 3H, ArCH$_3$), 2.20 (s, 3H, ArCH$_3$), 3.00 (s, 6H, N(CH$_3$)$_2$), 4.60 (s, 2H, COCH$_2$O), 5.20 (s, 2H, PhCH$_2$O) |
| 353 | 2.15 (s, 3H, ArCH$_3$), 2.20 (s, 3H, ArCH$_3$), 3.30 (s, 6H, N(CH$_3$)$_2$) |
| 354 | 1.60–2.30 (m, 4H, THF), 2.10 (s, 3H, ArCH$_3$), 2.20 (s, 3H, ArCH$_3$), 3.00 (s, 6H, N(CH$_3$)$_2$), 3.70–4.00 (m, 4H, THF + OCH$_2$) 4.20 (m, 1H, THF) |
| 355 | 1.20–1.95 (m, 6H, THP), 2.10 (s, 3H, ArCH$_3$), 2.20 (s, 3H, ArCH$_3$), 3.00 (s, 6H, N(CH$_3$)$_2$), 3.40–4.10 (m, 5H, THP + OCH$_2$) |
| 357 | 2.10 (s, 3H, ArCH$_3$), 2.20 (s, 3H, ArCH$_3$), 3.00 (s, 6H, N(CH$_3$)$_2$) |
| 358 | 1.10 (t, 3H, OCH$_2$CH$_3$), 1.60 (d, 3H, CHCH$_3$), 2.10 (s, 3H, ArCH$_3$), 2.20 (s, 3H, ArCH$_3$), 3.00 (s, 6H, N(CH$_3$)$_2$), 4.20 (q, 2H, OC$\underline{H}$$_2$CH$_3$), 4.60 (q, 1H, C$\underline{H}$CH$_3$) |
| 359 | 2.10 (s, 3H, ArCH$_3$), 2.20 (s, 3H, ArCH$_3$), 3.00 (s, 6H, N(CH$_3$)$_2$), 4.25 (q, 2H, OCH$_2$CF$_3$) |
| 360 | 2.10 (s, 3H, ArCH$_3$), 2.20 (s, 3H, ArCH$_3$), 2.40 (m, 4H, OCH$_2$C$\underline{H}$$_2$CH$_2$), 3.00 (s, 6H, N(CH$_3$)$_2$), 3.40 (t, 2H, CH$_2$C$\underline{H}$$_2$CN) 3.90 (t, 2H, OC$\underline{H}$$_2$(CH$_2$)$_3$) |
| 361 | 2.05 (s, 3H, ArCH$_3$), 2.20 (s, 3H, ArCH$_3$), 3.00 (s, 6H, N(CH$_3$)$_2$) |
| 362 | 1.00 (s, 9H, C(CH$_3$)$_3$), 2.00 (s, 6H, ArCH$_3$), 3.00 (s, 6H, N(CH$_3$)$_2$) |
| 363 | 2.20 (s, 3H, ArCH$_3$), 3.00 (s, 6H, N(CH$_3$)$_2$) |
| 364 | 1.2 (t, 3H, NCH$_2$CH$_3$) 2.05 (s, 3H, ArCH$_3$), 2.2 (s, 3H, ArCH$_3$), 3 (s, 3H, NCH$_3$), 3.35 (br, 2H, NC$\underline{H}$$_2$CH$_3$) |
| 365 | 2.1 (s, ArCH$_3$), 2.2 (s, 3H, ArCH$_3$), 3.0 (s, 6H, N(CH$_3$)$_2$) |
| 366 | 2.1 (s, 3H, ArCH$_3$), 2.2 (s, 3H, ArCH$_3$), 3.0 (s, 6H, N(CH$_3$)$_2$) |

TABLE 2-continued

| Cmp | Data |
|---|---|
| 367 | 2.00 (s, 3H, CH$_3$CO), 2.10 (s, 3H, ArCH$_3$), 2.20 (s, 3H, ArCH$_3$), 2.98 (s, 6H, N(CH$_3$)$_2$) |
| 368 | 2.00 (s, 6H, ArCH$_3$), 3.00 (s, 6H, N(CH$_3$)$_2$) |
| 369 | 2.10 (s, 3H, ArCH$_3$), 2.20 (s, 3H, ArCH$_3$), 2.40 (s, 6H, Het(CH$_3$)$_2$), 3.00 (s, 6H, N(CH$_3$)$_2$) |
| 370 | 0.90 (d, 6H, CH$_2$CH(CH$_3$)$_2$), 1.80 (m, 1H, CH$_2$CH(CH$_3$)$_2$), 2.10 (s, 3H, ArCH$_3$), 2.20 (s, 3H, ArCH$_3$), 2.40 (d, 2H, CH$_2$CH(CH$_3$)$_2$), 3.00 (s, 6H, N(CH$_3$)$_2$) |
| 371 | 1.60 (s, 6H, C(CH$_3$)$_2$), 1.95 (s, 3H, ArCH$_3$), 2.10 (s, 3H, ArCH$_3$), 2.95 (s, 6H, N(CH$_3$)$_2$) |
| 372 | 1.05 (t, 6H, CH(CH$_3$)$_2$), 1.25 (t, 3H, OCH$_2$CH$_3$), 2.10 (s, 3H, ArCH$_3$), 2.20 (s, 3H, ArCH$_3$), 2.23 (m, 1H, CH(CH$_3$)$_2$), 3.00 (s, 6H, N(CH$_3$)$_2$), 4.20 (q, 2H, OCH$_2$CH$_3$) |
| 373 | 2.1 (s, 3H, ArCH$_3$), 2.2 (s, 3H, ArCH$_3$), 3.35 (s, 3H, NCH$_3$) |
| 374 | 1.45 (t, 3H, NCH$_2$CH$_3$), 2.15 (s, 3H, ArCH$_3$), 2.2 (s, 3H, ArCH$_3$), 3.8 (q, 2H, NCH$_2$CH$_3$) |
| 375 | 2.15 (s, ArCH$_3$), 2.25 (s, ArCH$_3$), 2.6 (s, 3H, NC(O)CH$_3$) |
| 376 | 1.45 (d, 3H, CHCH$_3$), 2.10 (s, 3H, ArCH$_3$), 2.20 (s, 3H, ArCH$_3$), 2.22 (s, 3H, COCH$_3$), 3.00 (s, 6H, N(CH$_3$)$_2$), 4.55 (q, 1H, OCHCH$_3$) |
| 377 | 0.93 (m, 6H, (CHCH$_2$CH$_3$)$_2$), 1.60 (m, 4H, (CHCH$_2$CH$_3$)$_2$), 2.10 (s, 3H, ArCH$_3$), 2.20 (s, 3H, ArCH$_3$), 3.00 (s, 6H, N(CH$_3$)$_2$), 4.00 (m, 1H, OCH) |
| 378 | 1.5–2.9 (m, 9H, cyp), 2.10 (s, 3H. ArCH$_3$), 2.20 (s, 3H, ArCH$_3$), 3.30 (s, 6H, N(CH$_3$)$_2$) |
| 379 | 2.10 (s, 3H, ArCH$_3$), 2.20 (s, 3H, ArCH$_3$), 3.00 (s, 6H. N(CH$_3$)$_2$) |
| 380 | 1.22 (t, 3H, OCH$_2$CH$_3$), 2.10 (s, 3H, ArCH$_3$), 2.20 (s, 3H, ArCH$_3$), 3.00 (s, 6H, N(CH$_3$)$_2$), 4.00 (s, 3H, OCH$_3$), 4.25 (q, 2H, OCH$_2$CH$_3$) |
| 381 | 2.05 (s, 3H, ArCH$_3$), 2.20 (s, 3H, ArCH$_3$), 3.00 (s, 6H, N(CH$_3$)$_2$) |
| 382 | 0.85 (t, 3H, CH$_2$CH$_3$), 1.25 (m, 6H, CH$_2$CH$_2$), 1.55 (m, 2H, ArCH$_2$CH$_2$), 2.05 (s, 3H, ArCH$_3$), 2.20 (s, 3H, ArCH$_3$), 2.50 (t, 2H, CH$_2$CH$_3$), 3.00 (s, 6H, NCH$_3$) |
| 383 | 2.00 (s, 6H, ArCH$_3$), 3.00 (s, 6H, N(CH$_3$)$_2$) |
| 384 | 2.10 (s, 3H, ArCH$_3$), 2.20 (s, 3H, ArCH$_3$), 3.00 (s, 6H, N(CH$_3$)$_2$), 3.45 (s, 6H, (OCH$_3$)$_2$), 3.93 (d, 2H, OCH$_2$), 4.68 (t, 1H, (CH$_3$O)$_2$CHCH$_2$) |
| 385 | 1.23 (t, 6H, (CH$_3$CH$_2$O)$_2$), 2.10 (s, 3H, ArCH$_3$), 2.20 (s, 3H, ArCH$_3$), 3.00 (s, 6H, N(CH$_3$)$_2$), 3.55–3.80 (m, 4H, (CH$_3$CH$_2$O)$_2$), 3.95 (d, 2H, OCH$_2$), 4.78 (t, 1H, (CH$_3$CH$_2$O)$_2$CH) |
| 386 | 1.32 (s, 9H, C(CH$_3$)$_3$), 2.13 (s, 3H, ArCH$_3$), 2.20 (s, 3H, ArCH$_3$), 3.00 (s, 6H, N(CH$_3$)$_2$), 4.30 (m, 4H, OCH$_2$CH$_2$O) |
| 388 | 2.10 (s, 3H, ArCH$_3$), 2.20 (s, 3H, ArCH$_3$), 3.00 (s, 6H, N(CH$_3$)$_2$) |
| 390 | 1.30 (s, 6H, PhC(CH$_3$)$_2$) 2.05 (s, 3H, ArCH$_3$), 2.20 (s, 3H, ArCH$_3$), 2.80 (s, 2H, PhCCH$_2$), 3.05 (s, 6H, N(CH$_3$)$_2$) |
| 391 | 1.55 (s, 6H, C(CH$_3$)$_2$), 2.10 (s, 3H, ArCH$_3$), 2.20 (s, 3H, ArCH$_3$), 3.05 (s, 6H, N(CH$_3$)$_2$) |
| 392 | 1.50 (s, 6H, C(CH$_3$)$_2$), 2.10 (s, 3H, ArCH$_3$), 2.20 (s, 3H, ArCH$_3$), 3.00 (s, 6H, N(CH$_3$)$_2$), 3.05 (s, 3H, OCH$_3$) |
| 393 | 1.25 (t, 3H, CH$_2$CH$_3$), 2.10 (s, 3H, ArCH$_3$), 2.25 (s, 3H, ArCH$_3$), 3.00(s, 3H, NCH$_3$) 3.40 (b, 2H, CH$_2$CH$_3$) |
| 394 | 2.00 (s, 3H, ArCH$_3$), 2,10 (s, 3H, ArCH$_3$), 2.20 (s, 3H, ArCH$_3$), 3.00 (s, 6H, N(CH$_3$)$_2$) |
| 395 | 1.20 (t, 3H, CH$_2$CH$_3$), 2.10 (s, 3H, ArCH$_3$), 2.20 (s, 3H, ArCH$_3$), 2.40 (s, 3H, ArCH$_3$), 3.00 (s, 3H, N(CH$_3$), 3.40 (br, 2H, NCH$_2$) |
| 396 | 1.30 (s, 9H, C(CH$_3$)$_3$), 1.90 (m, 4H, CH$_2$CH$_2$), 2.15 (s, 3H, ArCH$_3$), 2.25 (s, 3H, ArCH$_3$), 3.5 (m, 4H, CH$_2$NCH$_2$) |
| 397 | 2.10 (s, 3H, ArCH$_3$), 2.20 (s, 3H, ArCH$_3$) 3.00 (s, 6H, N(CH$_3$)$_2$) |

The following compounds of formula Ib (see Table 3), i.e. compounds of general formula I where R$^1$ is hydrogen, R$^3$ is methyl, R$^4$ is methyl, R$^5$ is methyl substituted at the 5-position of the phenyl ring, —A—R$^6$ is para to the amidine moiety and is 3-Bu$^t$-phenoxy, may be prepared by methods analogous to those of Examples 1 to 17 Where the moiety depicted on the right side of linkage A is attached to R$^6$.

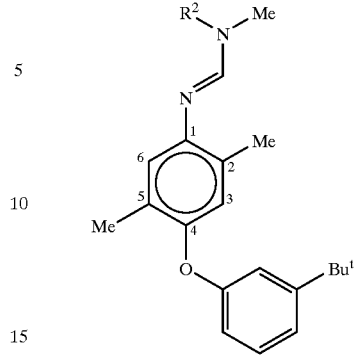

(Ib)

TABLE 3

| Cmp | R$^2$ | m.p./° C. |
|---|---|---|
| 501 | 1-Me-piperidin-4-yl | oil |
| 502 | 2-dimethylaminoethyl | oil |
| 503 | ethoxycarbonylmethyl | oil |
| 504 | propargyl | oil |
| 505 | 2,2-dimethoxyethyl | oil |
| 506 | 2-hydroxyethyl | oil |
| 507 | cyclopropyl | oil |
| 508 | cyclohexyl | oil |

Those compounds in Table 3 which do not have discrete melting points have the characteristic $^1$H N.M.R shown in Table 4 below.

TABLE 4

| Cmp | Data |
|---|---|
| 501 | 1.25 (s, 9H, C(CH$_3$)$_3$), 1.70–2.05 (m, 8H, cyCH$_2$), 2.10 (s, 3H, ArCH$_3$), 2.15 (s, 3H, ArCH$_3$), 2.30 (s, 3H, NCH$_3$), 2.90 (s, 3H, NCH$_3$) |
| 502 | 1.20 (s, 9H, C(CH$_3$)$_3$), 2.10 (s, 3H, ArCH$_3$), 2.20 (s, 3H, ArCH$_3$), 2.25 (s, 6H, CH$_2$N(CH$_3$)$_2$), 2.45 (m, 2H, NCH$_2$), 3.00 (s, 3H, NCH$_3$), 3.40 (m, 2H, NCH$_2$) |
| 503 | 1.00 (t, 3H, CH$_2$CH$_3$), 1.30 (s, 9H, C(CH$_3$)$_3$), 2.15 (s, 3H, ArCH$_3$), 2.20 (s, 3H, ArCH$_3$) 3.10 (s, 3H, NCH$_3$), 4.15 (s, 2H, NCH$_2$), 4.25 (q, 2H, CH$_2$CH$_3$) |
| 504 | 1.30 (s, 9H, C(CH$_3$)$_3$), 2.15 (s, 3H, ArCH$_3$), 2.20 (s, 2H, ArCH$_3$), 2.30 (s, 1H, CHC), 3.10 (s, 3H, NCH$_3$), 4.20 (s, 2H, NCH$_2$) |
| 505 | 1.30 (s, 9H, C(CH$_3$)$_3$), 2.20 (s, 3H, ArCH$_3$), 2.25 (s, 3H, ArCH$_3$), 3.15 (s, 3H, NCH$_3$), 3.50 (s, 6H, OCH$_3$), 3.60 9(m, 2H, NCH$_2$), 4.60 (m, 1H, CH) |
| 506 | 1.30 (s, 9H, C(CH$_3$)$_3$), 2.10 (s, 3H, ArCH$_3$), 2.20 (s, 3H, ArCH$_3$), 3.05 (s, 3H, NCH$_3$), 3.55 (s, 2H, OCH$_2$), 3.80 (s, 2H, NCH$_2$), 5.95 (m, 1H, OH) |
| 507 | 1.30 (s, 9H, C(CH$_3$)$_3$), 0.60 (s, 2H, cyCH$_2$), 0.70 (s, 2H, cyCH$_2$), 2.10 (s, 3H, ArCH$_3$), 2.20 (s, 3H, ArCH$_3$) |
| 508 | 0.85–1.90 (m, 10H, cyCH$_2$), 1.30 (s, 9H, C(CH$_3$)$_3$), 2.15 (s, 3H, CH$_3$), 2.20 (s, 3H, ArCH$_3$), 3.00 (s, 3H, NCH$_3$) |

EXAMPLE 18
N,N-Dimethyl-N'-[4-(3-trifluoromethyl % henoxy)-2,5-xylyl]formamidine sulfate salt
(Compound 602)

To a solution of the compound 1 (see Table 1) (0.3 g) in ethanol (0.3 ml) was added dropwise concentrated sulfuric acid (0.098 g). The mixture was filtered and the resulting solid was washed with diethyl ether to give the title compound as a solid, m.p. 178–80° C.

The following compounds of formula X (see Table 4), i.e. salts of general formula I where —A—R$^6$ is para to the amidine moiety, R$^1$ is hydrogen, R$^4$ is methyl, An is an anion and u is 1 or 2 depending on the valency of the anion, may be prepared by methods analogous to Example 18.

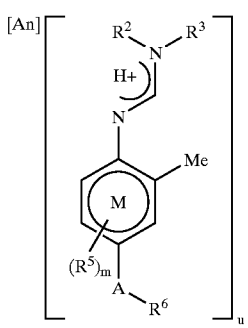

(X)

TABLE 5

| Cmp | Pos$^n$ of -A-R$^6$ | A | R6 | Data (m.p./° C. or 1H N.M.R) |
|---|---|---|---|---|
| 700 | 5 | —OCH$_2$— | 3-CF$_3$-phenyl | 2.00 (s, 3H, ArCH$_3$), 3.00 (s, 6H, N(CH$_3$)$_2$), 5.05 (s, 2H, ArCH$_3$) |
| 701 | 5 | —OCH$_2$— | 4-Bu$^t$-phenyl | 85–7 ° C. |
| 702 | 3 | —O— | 3-CF$_3$-phenyl | 2.10 (s, 3H, ArCH$_3$), 3.00 (s, 6H, N(CH$_3$)$_2$) |

TABLE 4

| Cmp | R$^2$ | R$^3$ | (R$^5$)$_m$ | A | R$^6$ | An$^-$ | m.p./° C. |
|---|---|---|---|---|---|---|---|
| 600 | Me | Me | 5-Me | —OCH$_2$— | 3-CF$_3$-phenyl | sulfate | 215–7 |
| 601 | Me | Me | 5-Me, 6-Br | O | 3-CF$_3$-phenyl | sulfate | 114–8 |
| 602 | Me | Me | 5-Me | O | 3-CF$_3$-phenyl | sulfate | 178–80 |
| 603 | Me | Me | 5-Me | O | 3-CF$_3$-phenyl | chloride | 152–4 |
| 604 | Me | Me | 5-Me | O | 3-CF$_3$-phenyl | p-toluenesulfonate | 133–5 |
| 605 | Me | Me | 5-Me | O | 3-CF$_3$-phenyl | saccharinate | oil |
| 606 | Me | Me | 5-Me | O | 3-CF$_3$-phenyl | trifluoroacetate | 141–3 |
| 607 | Me | Me | 5-Me | O | 3-CF$_3$-phenyl | methanesulfonate | 151–3 |
| 608 | Me | Me | 5-Me | O | 3-CF$_3$-phenyl | oxalate | 184–6 |
| 609 | Me | Me | 5-Me | O | 3-CF$_3$-phenyl | camphorsulfonate | oil |
| 610 | —(CH$_2$)$_4$— | | 5-Me | O | 3-CF$_3$-phenyl | chloride | 159–63 |
| 611 | Me | Me | 5-Me | O | 3-Ph-1,2,4-thiadiazol-5-yl | chloride | 80 |

Those compounds in Table 4 which do not have discrete melting points have the following characteristic $^1$H N.M.R. data in CDCl$_3$.

Compound 605

$^1$H N.M.R. δ(ppm) 2.15 (s, 3H, ArCH$_3$), 2.25 (s, 3H, ArCH$_3$), 3.20 (s, 3H, N(CH$_3$)), 3.25 (s, 3H, N(CH$_3$)), 10.20–10.80 (br, 1H, NH)

Compound 609

$^1$H N.M.R. δ(ppm) 0.75 (s, 3H, CCH$_3$), 1.05 (s, 3H, CCH$_3$), 1.25 (d, 2H, CH$_2$), 1.75–1.95 (m, 3H), 2.15 (s, 3H, ArCH$_3$), 2.20 (m, 1H, CH), 2.25 (s, 3H, ArCH$_3$), 2.35 (d, 1H, CH), 2.60 (t, 1H, CH), 2.85 (d, 1H, CH), 3.20 (s, 3H, N(CH$_3$), 3.30 (s, 3H, N(CH$_3$).

The following compounds of formula Ic (see Table 5), i.e. compounds of general formula I where R$^1$ and R$^5$ are hydrogen, R$^2$, R$^3$ and R$^4$ are methyl, may be prepared by methods analogous to those of Examples 1 to 17. Where the moiety depicted on the right side of linkage A is attached to R$^6$.

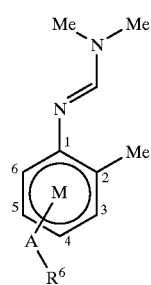

(Ic)

Test Examples

Compounds were assessed for activity against one or more of the following:

*Phytophthora infestans*: late tomato blight
*Plasmopara viticola*: vine downy mildew
*Erysiphe graminis* f. sp. *tritici*: wheat powdery mildew
*Pyricularia oryzae*: rice blast
*Leptosphaeria nodorum*: glume blotch Aqueous solutions or dispersions of the compounds at the desired concentration, including a wetting agent, were applied by spray or by drenching the stem base of the test plants, as appropriate. After a given time, plants or plant parts were inoculated with appropriate test pathogens before or after application of the compounds as appropriate, and kept under controlled environmental conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified.

*Phytophthora infestans*
7, 8, 28, 30, 36, 46, and 271.
*Plasmopara viticola*
149, 331, 373 and 364.
*Erysiphe graminis* f. sp. *Tritici*
1–5, 7–9, 11–13, 15–24, 26, 2841, 43, 45, 46, 48, 51, 52, 55, 56, 58, 59, 61, 62, 65, 68, 76, 84, 86, 90, 100, 101, 104–106, 109, 112, 113, 120, 123, 124, 130, 135, 138, 139, 140, 141, 143, 146, 149, 160, 166, 171, 173–175, 183, 187–190, 193–196, 200, 203–205, 207–209, 213, 215–217, 223, 225, 228, 231, 232, 234, 237, 246, 250, 252, 253, 256, 258, 259, 261, 262, 264, 266–272, 277, 279, 281, 282, 284, 286–288, 290, 291, 295, 298, 299, 301, 303, 310–312, 318, 325, 326, 330, 331, 335, 346, 347, 349, 351, 353, 355–357, 359, 361, 364, 365–368, 370–372, 374, 376–379, 392, 396, 398, 502, 504, 600, 601, 610 and 611.

*Pyricularia oryzae*

7, 17, 20, 21, 23, 26–28, 30, 32, 34, 36, 38, 41, 43, 45, 51, 54, 55, 59, 63, 94, 140, 143, 146, 163, 225, 325, 352, 353, 360, 368, 600 and 611.

*Leptosphaeria nodorum*

1, 2, 5, 7, 8, 15, 27, 29, 35, 37, 41, 43, 45, 48, 56, 59, 61, 72, 100, 130, 160, 170, 181, 194, 208, 214, 235, 246, 283, 284, 290, 303, 310, 311, 312, 325, 326, 351, 364, 369, 378 and 392

What is claimed is:

1. A compound of formula I and salts thereof

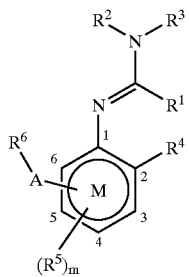

(I)

wherein $R^1$ is hydrogen, optionally substituted alkyl, optionally substituted alkenyl, optionally substituted alkynyl, optionally substituted carbocyclyl and optionally substituted heterocyclyl;

each of $R^2$ and $R^3$, which may be the same or different, is any group defined for $R^1$, or together with the nitrogen to which they are attached form a ring, which may be substituted;

$R^4$ is selected from the group consisting of alkyl, alkenyl, alkynyl, carbocyclyl and heterocyclyl, each of which may be substituted;

m is 1;

$R^5$ is any group defined for $R^4$ attached to the 5-position of the benzene ring M;

$R^6$ is optionally substituted carbo- or heterocyclyl; and

A is selected from the group consisting of a direct bond, —O—, —S—, —NR$^9$—, —CHR$^7$—, and —O—CHR$^7$—;

where $R^9$ is selected from the group consisting of alkyl, alkenyl and alkynyl, each of which may be substituted by a member of the group consisting of alkoxy, haloalkoxy, alkylthio, halogen and optionally substituted phenyl;

where $R^7$ is selected from the group consisting of alkyl, alkenyl and alkynyl, which may be substituted by a member of the group consisting of alkoxy, haloalkoxy, alkylthio, halogen and phenyl optionally substituted by a member of the group consisting of alkyl, haloalkyl, alkoxy, haloalkoxy and alkylthio;

where —A—R$^6$ is in the 4-position of the benzene ring M and the moiety depicted on the right side of linkage A is attached to R$^6$, or —A—R$^6$ and R$^5$ together with benzene ring M form an optionally substituted fused ring system.

2. The compound of claim 1, wherein $R^1$ is alkyl or hydrogen;

each of $R^2$ and $R^3$, which may be the same or different, is selected from the group consisting of hydrogen, alkyl, alkenyl and carbocyclyl;

$R^4$ is alkyl or alkenyl, m is 1;

$R^5$ is any group defined for $R^4$ attached to the 5-position of the benzene right M;

$R^6$ is optionally substituted carbo- or heterocyclyl; and

A is selected from the group consisting of a direct bond, —O—, —S—, and NR$^9$—, where $R^9$ is selected from the group consisting of —CHR$^7$—, —O—CHR$^7$—, optionally substituted alkyl, optionally substituted alkenyl and optionally substituted alkynyl, where said substitution group is selected from the group consisting of alkoxy, haloalkoxy, alkylthio, halogen and optionally substituted phenyl;

where $R^7$ is selected from the group consisting of hydroxy, halogen, cyano, acyl, alkoxy, haloalkoxy, alkylthio, optionally substituted alkyl, optionally substituted alkenyl, and optionally substituted alkynyl, where said substitution group is selected from the group consisting of alkoxy, haloalkoxy, alkylthio, halogen and phenyl optionally substituted by a member of the group selected from alkyl, haloalkyl, alkoxy, haloalkoxy and alkylthio; and where —A—R$^6$ is in the 4-position of the benzene ring M and the moiety depicted on the right side of linkage A is attached to R$^6$;

or —A—R$^6$ and R$^5$ together with benzene ring M form an optionally substituted fused ring system.

3. The compound of claim 2 wherein $R^1$ is hydrogen;

$R^2$ and $R^3$, which may be the same or different, are alkyl or alkenyl;

$R^4$ is alkyl;

m is 1;

$R^5$ is any group defined for $R^4$ attached to the 5-position of the benzene ring M;

$R^6$ is optionally substituted carbo- or heterocyclyl; and

A is —O—;

where —A—R$^6$ is in the 4-position of the benzene ring M and the moiety depicted on the right side of linkage A is attached to R$^6$.

4. The compound of claim 1, which is selected from the group consisting of:

N'-[4-(3-tert-butylphenoxy)-2,5-dimethylphenyl]-N,N-dimethylimidoformamide,

N'-[4-(3-tert-butylphenoxy)-2,5-dimethylphenyl]-N-ethyl-N-methylimidoformamide,

N-allyl-N'-[4-(3-tert-butylphenoxy)-2,5-dimethylphenyl]-N-methylimidoformamide,

N'-(4-{[4-(2-chlorophenyl)-1,3-thiazol-2-yl]oxy}-2,5-dimethylphenyl)-N,N-dimethylimidoformamide, N'-[2,5-dimethyl-4-(3-phenoxyphenoxy)phenyl]-N-ethyl-N-methylimidoformamide, N'-{4-[4-chloro-3-(trifluoromethyl)phenoxy]-2,5-dimethylphenyl}-N,N-dimethylimidoformamide, N'-{4-[4-chloro-3-(trifluoromethyl)phenoxy]-2,5-dimethylphenyl}—N-ethyl-N-methylimidoformamide, N'-{4-[3-(1-methoxy-1-methylethyl)phenoxy]-2,5-dimethylphenyl}-N,N-dimethylimidoformamide, and N-ethyl-N'-{4-[4-fluoro-3-(trifluoromethyl)phenoxy]-2,5-dimethylphenyl}—N-methylimidoformamide.

5. A fungicidal composition comprising at least one compound as claimed in claim 1, in admixture with an agriculturally acceptable diluent or carrier.

6. A method of combating fungi at a locus infested or liable to be infested therewith, which comprises applying to the locus a compound of formula I or a salt thereof wherein $R^1$ is hydrogen, optionally substituted alkyl, optionally substituted alkenyl, optionally substituted alkynyl, optionally substituted carbocyclyl and optionally substituted heterocyclyl;

each of $R^2$ and $R^3$, which may be the same or different, is any group defined for $R^1$, or together with the nitrogen to which they are attached form a ring, which may be substituted;

$R^4$ is selected from the group consisting of alkyl, alkenyl, alkynyl, carbocyclyl and heterocyclyl, each of which may be substituted;

m is 1;

$R^5$ is any group defined for $R^4$ attached to the 5-position of the benzene ring M;

$R^6$ is optionally substituted carbo- or heterocyclyl; and

A is selected from the group consisting of a direct bond, —O—, —S—, —$NR^9$—, —$CHR^7$—, and —O—$CHR^7$—;

where $R^9$ is selected from the group consisting of alkyl, alkenyl and alkynyl, each of which may be substituted by a member of the group consisting of alkoxy, haloalkoxy, alkylthio, halogen and optionally substituted phenyl;

where $R^7$ is selected from the group consisting of alkyl, alkenyl and alkynyl, which may be substituted by a member of the group consisting of alkoxy, haloalkoxy, alkylthio, halogen and phenyl optionally substituted by a member of the group consisting of alkyl, haloalkyl, alkoxy, haloalkoxy and alkylthio;

where —A—$R^6$ is in the 4-position of the benzene ring M and the moiety depicted on the right side of linkage A is attached to $R^6$, or —A—$R^6$ and $R^5$ together with benzene ring M form an optionally substituted fused ring system.

7. The method of claim 6, wherein $R^1$ is selected from the group consisting of alkyl, alkenyl and alkynyl, each of which may be substituted by a member of the group consisting of alkoxy, haloalkoxy, alkylthio, halogen and optionally substituted phenyl.

8. The method of claim 6, wherein $R^1$ is hydrogen.

9. The method of claim 6, wherein $R^1$ is $C_1$–$C_{10}$ alkyl.

10. The method of claim 6, wherein each of $R^2$ and $R^3$, which may be the same or different, is selected from the group consisting of alkyl, alkenyl and alkynyl, each of which may be substituted by a member of the group consisting of alkoxy, haloalkoxy, alkylthio, halogen, and optionally substituted phenyl.

11. The method of claim 6, wherein each of $R^2$ and $R^3$, which may be the same or different, is $C_1$–$C_{10}$ alkyl or hydrogen.

12. The method of claim 6, wherein $R^4$ is selected from the group consisting of alkyl, alkenyl and alkynyl, each of which may be substituted by a member of the group consisting of alkoxy, haloalkoxy, alkylthio, halogen and optionally substituted phenyl.

13. The method of claim 6, wherein $R^4$ is $C_1$–$C_{10}$ alkyl or halogen.

14. The method of claim 6, wherein $R^5$ is selected from the group consisting of alkyl, alkenyl and alkynyl, each of which may be substituted by a member of the group consisting of alkoxy, haloalkoxy, alkylthio, halogen and optionally substituted phenyl.

15. The method of claim 6, wherein, when present, $R^7$ is selected from the group consisting of alkyl, alkenyl, and alkynyl, each of which may be substituted by a member of the group consisting of alkoxy, haloalkoxy, alkylthio, halogen, and phenyl optionally substituted by a member selected from the group consisting of alkyl, haloalkyl, alkoxy, haloalkoxy, and alkylthio.

16. The method of claim 6, wherein, when present, $R^7$ is selected from the group consisting of hydroxy, halogen, cyano, acyl, alkoxy, haloalkoxy, alkylthio and hydrogen.

17. The method of claim 6, wherein $R^6$ is optionally substituted phenyl or optionally substituted aromatic heterocyclyl.

18. The method of claim 6, wherein $R^6$ is substituted by one or more substituents, which may be the same or different, and selected from the group consisting of alkyl, alkenyl, alkynyl, carbo- and heterocyclyl, each of which may be substituted.

19. The method of claim 6, wherein $R^6$ is substituted by one or more substituents, which may be the same or different, and selected from the group consisting of hydroxy, mercapto, azido, nitro, halogen, cyano, acyl, optionally substituted amino, cyanato, thiocyanato, —$SF_5$, —$OR^a$; —$SR^a$ and —$Si(R^a)_3$, where $R^a$ is selected from the group consisting of alkyl, alkenyl, alkynyl, carbocyclyl and heterocyclyl, each of which may be substituted.

20. The method of claim 6, wherein $R^6$ is substituted by one or more substituents, which may be the same or different, and selected from the group consisting of hydroxy, halogen, cyano, acyl, amino, alkylamino, dialkylamino, alkyl, haloalkyl, $R^a$O-alkyl, acyloxyalkyl, cyano-oxyalkyl, alkoxy, haloalkoxy, alkylthio, carbocyclyl, and benzyl, where $R^a$ is selected from the group consisting of alkyl, alkenyl, alkynyl, carbocyclyl and heterocyclyl, each of which may be substituted.

21. The method of claim 20, wherein said $R^6$ is substituted by carbocyclyl, which is optionally substituted by a member selected from the group consisting of alkyl, haloalkyl, alkoxy, haloalkoxy and alkylthio.

22. The method of claim 20, wherein said $R^6$ is substituted by benzyl, which is optionally substituted by a member selected from the group consisting of alkyl, haloalkyl, alkoxy, haloalkoxy and alkylthio.

* * * * *